United States Patent
Woosley et al.

(10) Patent No.: US 10,774,336 B2
(45) Date of Patent: Sep. 15, 2020

(54) INCREASED PROTEIN EXPRESSION IN PLANTS

(71) Applicant: Dow AgroSciences LLC, Indianapolis, IN (US)

(72) Inventors: Aaron Woosley, Fishers, IN (US); Sarah Worden, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 221 days.

(21) Appl. No.: 14/599,374

(22) Filed: Jan. 16, 2015

(65) Prior Publication Data

US 2015/0203857 A1 Jul. 23, 2015

Related U.S. Application Data

(60) Provisional application No. 61/928,852, filed on Jan. 17, 2014.

(51) Int. Cl.
*C12N 15/82* (2006.01)
*A23L 7/10* (2016.01)
*A01N 37/46* (2006.01)

(52) U.S. Cl.
CPC ......... *C12N 15/8216* (2013.01); *A01N 37/46* (2013.01); *A23L 7/198* (2016.08); *C12N 15/8286* (2013.01); *Y02A 40/162* (2018.01)

(58) Field of Classification Search
CPC .......................... A23L 1/1041; C12N 15/8216
USPC .................................................. 800/302, 279
See application file for complete search history.

(56) References Cited

U.S. PATENT DOCUMENTS

| | | | |
|---|---|---|---|
| 5,500,365 A | 3/1996 | Fischhoff et al. | |
| 6,720,488 B2 | 4/2004 | Koziel et al. | |
| 7,741,118 B1 † | 6/2010 | Fischhoff | |
| 8,309,516 B2 | 11/2012 | Hart et al. | |
| 9,427,003 B2 * | 8/2016 | Larrinua | A23D 9/00 |
| 2003/0046726 A1 | 3/2003 | Koziel et al. | |
| 2012/0266335 A1 | 10/2012 | Larrinua et al. | |

FOREIGN PATENT DOCUMENTS

| | | |
|---|---|---|
| EP | 0431829 A1 † | 6/1991 |
| WO | 2012/142371 A1 † | 10/2012 |
| WO | 201213119 | 10/2012 |
| WO | 2012142371 | 10/2012 |

OTHER PUBLICATIONS

Kawabe et al., "Patterns of codon usage in three dicot and four monocot plant species", Genes Genet. Syst., 2003, 78:343-352.†
Murray et al., "Codon usage in plant genes", Nucl. Acids Research, 1989, 17:477-498.†
GenBank Sequences from Corn and Soybean submitted prior to Jan. 17, 2014.‡

\* cited by examiner
† cited by third party

*Primary Examiner* — Li Zheng
(74) *Attorney, Agent, or Firm* — Robert C. Lampe, III; Magleby, Cataxinos & Greenwood

(57) ABSTRACT

This disclosure concerns synthetic polynucleotides encoding a polypeptide of interest that are particularly well-suited for expression in target plants.

43 Claims, 10 Drawing Sheets

Specification includes a Sequence Listing.

INCREASED PROTEIN EXPRESSION IN PLANTS

CROSS-REFERENCE TO RELATED APPLICATION

This application claims priority to Provisional Patent Application Ser. No. 61/928,852 filed Jan. 17, 2014, the disclosure of which is hereby incorporated herein in its entirety by this reference.

FIELD OF THE DISCLOSURE

The present disclosure relates to methods and compositions for improving the expression of polynucleotides in a plant cell. In some embodiments, a protein encoding region of a polynucleotide is modified to reflect codon usage bias from a host organism while simultaneously preserving certain polyadenylation sequences in the native gene.

BACKGROUND

The genetic code consists of three-nucleotide units ("codons"). There are 64 possible codons, each specifying one of twenty amino acids, or an end to transcription (i.e., "STOP codons"). Therefore, at least some codons are redundant. In the coding system used by the vast majority of organisms, two amino acids are encoded by a single codon, whereas all other amino acids are encoded by two, three, four, or six codons, with three STOP codons. For amino acids with two, three, or four codons, the codons differ from each other at the third nucleotide position. For the three that have six codons, they have one block of four codons that follows this pattern, and one additional set of two that also differ from each other in the third position. For the two amino acids represented by six codons (Arg and Leu), they are each represented by a block different from the other by a change in the second nucleotide position. The codon representation of serine (Ser) is unusual, in that the two blocks of codons are very similar. For amino acids represented by two codons, the third position is either a purine (A, G) or pyrimidine (C, T) in both cases.

The degeneracy of the genetic code provides an opportunity to construct an alternative polynucleotide that encodes the polypeptide product of a reference polynucleotide. For example, codon degeneracy allows one to make synthetic DNA sequences that encode a protein of interest using codons that differ from those used in the original DNA coding sequence. For a particular amino acid, a given organism does not use the possible codons equally. Organisms each have a bias in codon usage. The pattern of bias in codon usage is distinct for an organism and its close relatives throughout the genome. For example, in *Streptomyces* spp., frequent codons generally include G or C in the third nucleotide position. Rare codons generally include A or T in the third position. In other organisms, A or T is preferred in the third position. Within a particular species, there can be distinct categories of genes with their own codon bias. In *E. coli*, for example, there are roughly three classes of genes, each with a distinctive codon usage signature. One class is rich in important proteins that are abundantly expressed; the second class includes proteins that are expressed at relatively low levels; and the third class includes proteins likely to have been recently acquired from other species.

To achieve desired expression levels of heterologous proteins in transgenic plants, it has been found beneficial to alter the native (sometimes referred to as wild-type or original) DNA coding sequence in various ways, for example, so that the codon usage more closely matches the codon usage of the host plant species, and/or so the G+C content of the coding sequence more closely matches the G+C level typically found in coding sequences of the host plant species, and/or so that certain sequences that destabilize mRNA are removed. For example, the expression of *Bacillus thuringiensis* (Bt) crystal protein insect toxins in plants has been improved using one or more of these approaches. See, e.g., U.S. Pat. Nos. 5,380,301; 5,625,136; 6,218,188; 6,340,593; 6,673,990; and 7,741,118.

In most synthetic gene design strategies, the process attempts to match the codon composition of a synthetic gene to the codon compositions of genes of a host in which the synthetic gene will be expressed. See, e.g., U.S. Patent Publication No. US 2007/0292918 A1. Such strategies may in some situations lead to increased expression of the synthetic gene in the host. For example, codon optimization in yeast may significantly improve the translation of heterologous gene transcripts due to minimizing the effects of, e.g., limiting aminoacyl-tRNAs and transcription termination at AT-rich sequences. See, e.g., Daly and Hearn (2004) J. Mol. Recognition. 18:119-38.

However, despite general agreement in the art over the need for some sort of codon optimization, practitioners disagree over the general strategy that should be employed for optimization. One strategy that is preferred by some is to maximize the use of frequent codons in the expression host species during the design of heterologous genes. A second strategy preferred by others is to place maximum value on the context of particular codons, and therefore to maximize the use of codon pairs that occur frequently in the expression host. A third strategy is to make the codon usage of the new coding sequence in the new species resemble the codon usage of the reference coding sequence in the species of origin. This third strategy places high value on the recognition of possible requirements for rare codons to ensure proper secondary structure of transcript RNA molecules. Additionally, simply using the same frequently-occurring codon repeatedly in a heterologous sequence is expected to eventually have the same effect as selecting a rare codon; e.g., overuse of the corresponding tRNA will limit the availability of the tRNA. A person attempting to optimize the codons of a gene sequence for expression in a host organism must balance these strategies and their underlying concerns in order to arrive at a particular methodology.

The process of optimizing the nucleotide sequence coding for a heterologously expressed protein can be an important step for improving expression yields. However, several potential problems limit the usefulness of optimization for the expression of particular genes. For example, the secondary structure of an optimized transcript may limit translation of the transcript. Griswold et al. (2003) Protein Expression and Purification 27:134-42. Additionally, there are a number of sequence motifs that are desirably avoided in synthetic sequences for heterologous expression, including class I and II transcriptional termination sites in *E. coli* for a gene under the control of a T7 promoter; Shine-Dalgarno-like sequences; potential splice signals; sequences that promote ribosomal frameshifts and pauses; and polyadenylation signals. Welch et al. (2010) J. R. Soc. Interface 6:S467-76. In particular, the understanding in the art is that polyadenylation signal sequences should be reduced to enable enhanced expression of synthetic genes in plants. U.S. Pat. No. 7,741,118.

BRIEF SUMMARY OF THE DISCLOSURE

Contrary to the understanding in the art (See, e.g., U.S. Pat. No. 7,741,118), we have recently found that a reduction in the number of the polyadenylation signal sequences (e.g., AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA) is neither necessary nor sufficient to enable enhanced expression of synthetic genes in plants. Embodiments herein make practical use of the surprising and unexpected result that preservation of these polyadenylation sequences in a synthetic coding sequence with respect to their occurrence in a native sequence may be utilized in a gene optimization process to increase heterologous protein expression.

Embodiments herein include synthetic nucleic acids encoding at least one polypeptide of interest. In embodiments, a synthetic nucleic acid encoding at least one polypeptide of interest is designed according to the constraints of specific gene design parameters that generally increase the expression of the polypeptide of interest from the nucleic acid in a host (e.g., a plant cell, plant tissue, and plant). Synthetic nucleic acid sequences may be designed from a reference nucleic acid sequence, for example, to optimize heterologous expression of the nucleic acid sequence in the host organism.

In some embodiments, a synthetic nucleic acid encoding a polypeptide of interest has been engineered for expression of the heterologous polypeptide in a host cell, wherein the polypeptide is produced in a non-genetically engineered cell in a species other than that of the host cell, and is encoded by a reference polynucleotide therein. In some embodiments, the synthetic nucleic acid is codon-optimized for expression in the host cell, for example, by altering the nucleotide sequence of the reference polynucleotide to have substantially all of the codons therein be preferred (e.g., most-preferred) codons in the host organism. In some embodiments, further analysis and engineering may be performed upon a codon-optimized synthetic nucleic acid, for example, to confirm the absence of undesired nucleic acid motifs (e.g., nucleic acid motifs forming undesirable secondary structure in an RNA molecule transcribed therefrom), confirm the absence of restriction enzyme recognition sites, and/or assure codon and sequence diversity.

In some embodiments, a synthetic nucleic acid encoding a polypeptide of interest comprises a coding sequence that is codon-optimized for expression in a heterologous cell, and at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, wherein the at least one polyadenylation sequence is in the corresponding location of the coding sequence as in a reference polynucleotide. In particular embodiments, the synthetic nucleic acid comprises the same number of the foregoing polyadenylation sequences as occur in the reference polynucleotide. In particular embodiments, the synthetic nucleic acid comprises the same number of the foregoing polyadenylation sequences as occur in the reference polynucleotide, and the polyadenylation sequences are each in their corresponding locations of the coding sequence as in the reference polynucleotide.

Some embodiments include methods of making a synthetic nucleic acid encoding a polypeptide of interest, wherein the methods comprise providing the amino acid sequence of a polypeptide of interest that is encoded by a reference polynucleotide in a non-genetically engineered cell that comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, and producing a synthetic nucleic acid encoding the polypeptide of interest that contains at least one of the polyadenylation sequences is in the corresponding location of the coding sequence of the synthetic nucleic acid as in the reference polynucleotide. In particular embodiments, the synthetic nucleic acid is produced so that it comprises the same number of the foregoing polyadenylation sequences as occur in the reference polynucleotide, and the polyadenylation sequences are each in their corresponding locations of the coding sequence of the synthetic nucleic acid as in the reference polynucleotide.

Other embodiments include vectors (e.g., plant transformation vectors) comprising at least one of the foregoing synthetic nucleic acids. Particular embodiments include vectors comprising a transcription unit comprising a synthetic nucleic acid encoding a polypeptide of interest comprises a coding sequence that is codon-optimized for expression in a heterologous cell, and at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, wherein the at least one polyadenylation sequence is in the corresponding location of the coding sequence as in a reference polynucleotide. In some examples, such a vector may comprise, for example and without limitation: a 5' non-translated sequence (e.g., comprising a plant promoter); a synthetic DNA sequence; and a 3' non-translated region (e.g., comprising a transcription termination signal).

Particular embodiments include methods of generating a plant, plant part, plant organ, plant seed, and/or plant cell that expresses a polypeptide of interest (e.g., a heterologous polypeptide of interest). Methods according to particular embodiments comprise: transforming a plant, plant part, plant organ, plant seed, and/or plant cell with at least one synthetic nucleic acid encoding a polypeptide of interest comprises a coding sequence that is codon-optimized for expression in a heterologous cell, and at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, wherein the at least one polyadenylation sequence is in the corresponding location of the coding sequence as in a reference polynucleotide; and expressing the nucleic acid so as to produce the polypeptide of interest encoded thereby. In examples, a plant, plant part, plant organ, plant seed, and/or plant cell transformed with the foregoing synthetic nucleic acids may express the polypeptide of interest in a greater amount than a plant, plant part, plant organ, plant seed, and/or plant cell of the same species transformed with the reference polynucleotide.

Some embodiments include a plant, plant part, plant organ, plant seed, and/or plant cell comprising a synthetic nucleic acid encoding a polypeptide of interest comprises a coding sequence that is codon-optimized for expression in a heterologous cell, and at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, wherein the at least one polyadenylation sequence is in the corresponding location of the coding sequence as in a reference polynucleotide encoding the native polypeptide of interest in a non-genetically modified organism.

Other embodiments include methods of obtaining a desirable expression phenotype in a plant. Methods according to some embodiments include transforming a plant, plant part, plant organ, plant seed, and/or plant cell with at least one synthetic nucleic acid encoding a polypeptide of interest comprises a coding sequence that is codon-optimized for expression in a heterologous cell, and at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, wherein the at least one polyadenylation sequence is in the corresponding location of the coding sequence as in a reference polynucleotide, and wherein the polypeptide of interest is expressed in the part, plant organ, plant seed, and/or plant cell, thereby conferring or enhancing a phenotype thereof. Examples of phenotypes that may be obtained or enhanced in particular embodiments include, for example and without limitation: pest resistance and/or control; herbicide tolerance; modified oil characteristics; and stress tolerance.

For example, methods in some embodiments include controlling pests in a plant, grain, and/or seeds, by expressing at least one synthetic polynucleotide in a plant cell, wherein the synthetic polynucleotide encodes an insect toxin (e.g., a *Bacillus thuringiensis* Cry protein); controlling pests in meal or flour by providing meal or flour from grain obtained from a transgenic plant expressing an insect toxin from a synthetic polynucleotide; increasing herbicide tolerance in a plant by expressing at least one synthetic polynucleotide in the plant, wherein the synthetic polynucleotide encodes an herbicide tolerance polypeptide (e.g., the aryloxyalkanoate dioxygenase (AAD1); phosphinothricin acetyltransferase; and 5-enolpyruvylshikimate-3-phosphate synthase); modifying oil profiles in a plant by expressing at least one synthetic polynucleotide in the plant, wherein the synthetic polynucleotide encodes a polypeptide for modifying oil profiles in plants (e.g., fatty acid desaturase); and increasing stress tolerance (e.g., water and/or heat stress tolerance) in a plant by expressing a synthetic polynucleotide in the plant, wherein the synthetic polynucleotide encodes the product of a stress tolerance gene (e.g., the stress associated protein (SAP1) and/or 1-Cys peroxiredoxin (Per1) proteins). Particular embodiments include methods for introducing a reporter gene into a plant by expressing a synthetic polynucleotide in the plant, wherein the synthetic polynucleotide encodes a transformation marker protein (e.g., GFP and/or beta-glucuronidase).

Also included in some embodiments is a composition (e.g., a commodity product) produced from transgenic plants or parts or materials thereof containing a synthetic nucleic acid encoding a polypeptide of interest comprises a coding sequence that is codon-optimized for expression in a heterologous cell, and at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, wherein the at least one polyadenylation sequence is in the corresponding location of the coding sequence as in a reference polynucleotide. In particular embodiments, the composition is a commodity product selected from a group comprising meal, flour, protein concentrate, and oil.

The foregoing and other features will become more apparent from the following detailed description of several embodiments, which proceeds with reference to the accompanying figures.

SEQUENCE LISTING

Figure 1:
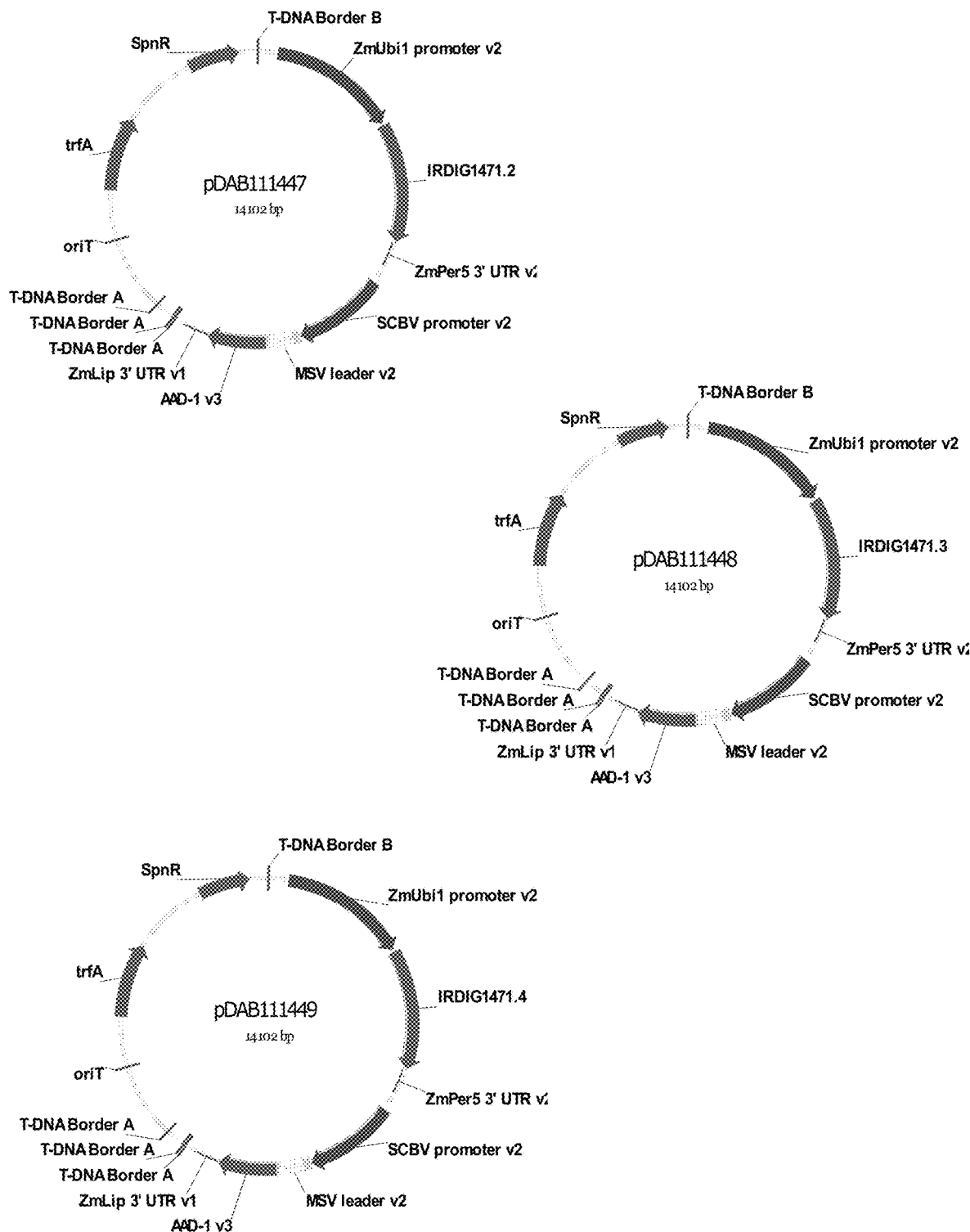
FIG. 1 includes depictions of three exemplary binary plasmids that were used for Cry1Ab corn transformation. All of the plasmids are identical, with the exception of the cry1Ab polynucleotide.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NO:1 shows a polynucleotide sequence, referred to in some places herein as IRDIG.1471.2:

ATGGATAACAACCCGAACATCAACGAGTGCATCCCGTACAACTGCCTGAG
CAACCCGGAGGTGGAGGTGCTGGGCGGCGAGAGGATCGAGACCGGCTACA
CCCCGATCGACATCAGCCTGTCCCTGACCCAGTTCCTGCTGTCCGAGTTC
GTGCCTGGCGCTGGCTTCGTGCTGGGACTCGTGGATATAATCTGGGGAAT
CTTTGGCCCGTCCCAGTGGGACGCCTTCCTGGTGCAGATCGAGCAGCTAA
TTAACCAAAGGATCGAGGAGTTCGCGAGGAACCAAGCCATTTCGAGGCTG
GAGGGCCTGTCCAACCTGTACCAAATCTACGCGGAGAGCTTCCGCGAGTG
GGAGGCGGACCCGACCAACCCGGCCCTGAGGGAGGAGATGAGGATACAGT
TCAACGACATGAACTCCGCGCTGACCACCGCCATCCCGCTGTTCGCCGTG
CAGAACTACCAAGTGCCGCTGCTGTCCGTGTACGTGCAAGCCGCGAACCT
GCACCTGAGCGTGCTGAGGGACGTGAGCGTCTTTGGCCAGAGGTGGGGCT
TCGACGCGGCGACCATCAACAGCAGATACAACGACCTGACCAGACTGATC
GGCAACTACACCGACTACGCCGTGAGGTGGTACAACACCGGCCTGGAGAG
GGTGTGGGGCCCGGACTCAAGGGACTGGGTGAGATACAATCAATTCAGAA
GGGAATTAACCCTGACCGTGCTGGACATCGTGGCCCTGTTCCCGAACTAC
GACTCAAGGAGATACCCGATCAGAACCGTGTCCCAATTAACCAGAGAAAT
CTACACCAACCCGGTGCTGGAGAACTTCGACGGCAGCTTCAGAGGCAGCG
CCCAAGGCATCGAGAGGAGCATCAGATCCCCGCACCTGATGGACATCCTG
AACTCCATCACCATCTACACCGACGCGCACAGAGGCTACTACTACTGGAG
CGGCCACCAAATAATGGCCTCCCCGGTGGGCTTCTCCGGCCCGGAGTTCA
CCTTCCCGCTGTACGGCACAATGGGCAACGCGGCCCCGCAGCAGAGGATC
GTGGCGCAGCTGGGCCAAGGCGTGTACAGAACCCTCAGCTCCACCCTGTA
CAGAAGGCCGTTCAACATCGGCATCAATAATCAACAGCTGAGCGTGCTGG
ACGGCACCGAGTTCGCATACGGCACCTCCTCCAACCTGCCGAGCGCCGTG
TACAGAAAGTCCGGCACCGTGGACTCCCTGGATGAAATCCCGCCGCAGAA
CAACAACGTGCCGCCGAGGCAAGGCTTCAGCCACAGACTGAGCCACGTGA
GCATGTTCAGATCCGGCTTCTCAAACTCCAGCGTGAGCATCATCAGAGCG
CCGATGTTCAGCTGGATACATAGGAGCGCGGAGTTCAATAATATAATCCC
CAGCTCTCAGATCACCCAGATCCCGCTGACCAAGTCCACCAACCTGGGCT
CCGGCACCAGCGTGGTGAAGGGACCGGGCTTTACCGGCGGCGACATCCTG
AGGAGGACCTCCCCGGGCCAAATCTCCACCCTGAGGGTGAACATCACCGC
CCCGCTGAGCCAGAGATACAGAGTGAGGATCAGATACGCGTCCACCACCA
ACCTTCAGTTCCATACATCCATCGACGGGAGGCCGATTAATCAAGGCAAC
TTCTCCGCGACCATGTCCAGCGGCTCCAACCCTCCAGAGCGGCAGCTTCAG
AACCGTGGGCTTCACCACCCCGTTCAACTTCTCAAACGGCAGCAGCGTGT
TCACCCTGAGCGCCCACGTGTTCAACTCCGGCAACGAGGTGTACATCGAC
AGAATCGAGTTCGTGCCGGCAGAAGTGACCTTCGAGGCCGAGTACGACCT
GGAGAGGTGA

SEQ ID NO:2 shows a polynucleotide sequence, referred to in some places herein as IRDIG.1471.3:

ATGGACAACAACCCTAACATCAATGAGTGCATACCATACAACTGTCTTAG
CAACCCAGAAGTTGAGGTTCTGGGTGGGAGAGGATAGAGACTGGATACA
CTCCAATAGACATTTCGCTGTCACTGACGCAATTCCTTCTGTCTGAGTTC
GTTCCTGGTGCTGGATTCGTGCTGGGCTTGGTGGATATAATTTGGGGAAT
CTTTGGACCGTCCCAGTGGGATGCCTTTCTTGTTCAGATTGAGCAGCTAA
TTAACCAAAGAATTGAGGAGTTTGCACGCAACCAAGCCATATCCAGACTT
GAAGGCCTTTCGAACTTGTATCAAATCTACGCAGAGAGCTTCAGAGAGTG
GGAGGCAGACCCGACGAATCCAGCCCTCAGAGAGGAGATGAGGATTCAGT
TCAACGACATGAACTCAGCACTGACTACTGCCATTCCCCTCTTTGCCGTC
CAGAACTATCAAGTGCCACTGCTGTCCGTCTACGTTCAAGCAGCGAATCT
GCACCTCAGCGTCTTGAGAGACGTCTCGGTCTTTGGCCAGCGCTGGGGTT
TTGATGCAGCGACGATCAATAGCAGATACAATGACCTCACAAGGCTGATT
GGAAACTACACCGATTACGCAGTTCGCTGGTACAATACGGGTCTCGAACG
GGTCTGGGGACCCGACTCACGCGACTGGGTCAGATACAATCAATTCAGAC
GCGAATTAACTTTGACCGTTCTGGACATAGTCGCACTCTTTCCGAACTAC
GACAGCAGAAGATATCCGATTAGGACGGTTTCCCAATTAACCAGAGAAAT
CTATACCAATCCCGTGCTCGAAAACTTTGACGGCAGCTTTAGGGGAAGCG
CTCAAGGCATTGAGAGGAGCATCAGATCCCCACATCTCATGGACATTCTG
AACTCAATCACGATCTACACTGATGCACATAGGGGTTACTACTATTGGAG
CGGTCATCAAATAATGGCCTCGCCAGTGGGGTTTTCGGGTCCGGAGTTTA
CATTCCCACTGTACGGACAATGGGAAATGCAGCACCGCAACAGCGGATC
GTTGCTCAGCTGGGTCAAGGGGTGTACAGAACGCTCTCATCGACGCTGTA

-continued

TCGGAGACCCTTCAACATAGGCATCAATAATCAACAACTCTCAGTCTTGG
ACGGCACCGAGTTCGCGTATGGGACATCCTCCAACCTCCCGTCTGCCGTG
TATCGCAAGTCCGGAACAGTCGATTCGCTGGATGAAATTCCTCCACAGAA
CAACAACGTGCCTCCAAGACAAGGCTTCTCTCACAGATTGAGCCATGTGA
GCATGTTCCGCTCTGGCTTCTCCAACTCCTCAGTGTCGATCATTAGGGCA
CCGATGTTCTCTTGGATACATCGGAGCGCAGAGTTCAATAATATAATCCC
GTCAAGCCAGATCACGCAGATCCCACTGACCAAGTCCACCAATCTCGGCT
CTGGGACAAGCGTTGTGAAGGGTCCTGGCTTCACTGGTGGGGATATCCTG
CGGAGGACTTCTCCTGGCCAGATTTCAACCCTCAGAGTCAACATCACCGC
ACCCCTTTCACAGCGCTATCGGGTTCGCATACGCTACGCTTCCACGACCA
ATCTGCAATTCCATACATCCATCGACGGGAGGCCTATTAATCAAGGCAAC
TTCTCAGCGACTATGTCCTCGGGTTCTAACCTTCAGTCTGGCAGCTTCAG
AACGGTGGGGTTCACCACTCCATTCAACTTCTCGAACGGGTCAAGCGTGT
TCACCTTGAGCGCTCACGTGTTCAATTCCGGAAACGAAGTGTACATCGAC
CGCATAGAGTTCGTGCCAGCAGAAGTTACATTCGAAGCCGAGTACGATCT
TGAGAGGTGA

SEQ ID NO:3 shows a polynucleotide sequence, referred to in some places herein as IRDIG.1471.4:

ATGGATAACAACCCGAACATCAATGAGTGCATCCCGTATAACTGTCTCAG
TAACCCTGAAGTGGAGGTCTTAGGTGGCGAACGCATCGAAACTGGTTACA
CCCCAATCGACATTAGCTTGTCGTTGACGCAGTTCCTCTTGTCCGAGTTC
GTGCCCGGTGCGGGTTTCGTGCTGGGGCTAGTTGATATAATCTGGGGAAT
CTTTGGTCCCTCTCAGTGGGACGCCTTTCTTGTGCAAATTGAGCAGCTAA
TTAACCAAAGAATAGAAGAGTTCGCGAGGAACCAAGCCATTTCCAGACTG
GAGGGACTAAGCAACCTTTATCAAATCTACGCGGAGTCTTTTAGGGAGTG
GGAGGCAGATCCTACGAACCCGGCACTGCGCAAGAGATGCGTATTCAGT
TCAACGACATGAACAGTGCCCTTACAACCGCTATTCCCCTTTTCGCAGTT
CAAAATTACCAAGTTCCCCTTCTCTCAGTGTACGTTCAAGCCGCAAATTT
ACACCTAAGCGTTCTCCGCGATGTGTCAGTGTTCGGCCAGAGGTGGGGAT
TTGATGCCGCCACTATCAATAGTCGTTATAATGATCTGACGAGGCTTATC
GGCAACTATACCGACTATGCTGTCCGCTGGTACAATACGGGATTAGAGCG
GGTCTGGGGTCCGGATTCCCGAGACTGGGTGCGCTACAATCAATTCCGCC
GCGAATTAACCCTCACTGTCCTCGACATCGTGGCGCTGTTCCCGAACTAC
GACAGTAGGAGATACCCAATCCGCACAGTTTCCCAATTAACGCGGGAAAT
TTACACCAACCCAGTCCTGGAGAATTTTGACGGGAGCTTCCGAGGCTCGG
CTCAAGGCATAGAACGCAGCATTAGGTCGCCACACTTGATGGATATCCTT
AACAGCATCACCATCTACACGGATGCCCATAGGGGTTACTACTACTGGTC
GGGGCATCAAATAATGGCTTCTCCTGTCGGGTTTTCGGGGCCAGAGTTCA
CCTTCCCGCTCTACGGCACTATGGGAAATGCCGCGCCACAACAACGTATC
GTCGCTCAACTAGGTCAAGGCGTGTACCGGACACTGTCGTCCACTCTCTA

-continued

TCGGCGGCCTTTCAATATAGGGATCAATAATCAACAGTTGTCTGTGCTGG
ACGGGACAGAGTTTGCTTACGGAACCTCAAGCAACTTGCCATCCGCTGTA
TACAGAAAAGCGGCACGGTGGACTCGCTGGATGAAATCCCGCCCCAGAA
TAACAACGTGCCCCCTCGGCAAGGCTTCAGTCATCGACTGAGCCACGTTA
GCATGTTCCGTTCGGGCTTCAGCAACTCCTCCGTAAGTATCATAAGAGCA
CCTATGTTCAGCTGGATACATCGTTCCGCCGAGTTCAATAATATAATTCC
CTCCTCTCAAATCACACAGATCCCTCTGACAAAGTCTACTAATCTTGGCT
CTGGGACTTCTGTCGTTAAGGGGCCTGGCTTTACGGGCGGCGATATTCTG
CGGAGAACTTCACCTGGCCAGATTTCCACCCTGCGCGTGAATATCACCGC
GCCATTGTCACAACGTTACCGCGTGCGGATTCGCTACGCTTCTACCACAA
ACCTCCAGTTCCATACATCTATTGACGGCAGACCCATTAATCAAGGGAAT
TTCTCCGCCACGATGTCGTCCGGCTCCAATCTCCAGTCCGGAAGTTTCCG
CACCGTAGGTTTTACTACCCCGTTCAACTTTTCAAACGGCTCAAGTGTGT
TTACGCTGTCCGCTCATGTGTTCAACTCTGGCAATGAGGTTTACATCGAC
CGGATTGAGTTCGTCCCGGCAGAAGTCACCTTCGAAGCCGAGTACGATCT
TGAGAGGTGA

SEQ ID NO:4 shows a polynucleotide sequence, referred to in some places herein as IRDIG.586.34:

ATGGAGAATAATATCCAGAATCAATGCGTGCCGTACAACTGCCTGAATAA
TCCGGAGGTGGAGATATTAAACGAGGAGAGGAGCACCGGGAGGCTGCCGC
TGGACATCTCCCTGTCCCTGACCCGCTTCCTGCTGTCCGAGTTCGTCCCG
GGCGTGGGCGTGGCGTTCGGCCTGTTCGACCTGATCTGGGGCTTCATCAC
CCCGAGCGACTGGAGCCTGTTCCTGCTTCAGATCGAGCAGCTGATCGAGC
AGAGGATCGAGACCCTGGAGAGGAACCGCGCGATCACCACCCTGAGGGGC
CTGGCGGACAGCTATGAAATCTACATCGAGGCGCTGAGGGAGTGGGAGGC
CAACCCGAATAATGCTCAATTAAGGGAGGACGTGAGGATACGCTTCGCGA
ATACAGACGACGCGCTGATCACCGCAATCAATAATTTCACCCTGACCTCC
TTCGAGATCCCGCTGCTGAGCGTGTACGTCCAAGCGGCGAACCTGCACCT
GTCCCTGCTGAGGGACGCCGTGAGCTTTGGCCAAGGCTGGGGCCTGGACA
TCGCGACCGTGAATAATCACTACAACAGATTAATCAACCTGATCCACCGC
TACACCAAGCACTGCCTGGACACCTACAATCAAGGCCTGGAGAACCTGAG
GGGCACCAACACCCGCCAGTGGGCGAGGTTCAACCAGTTTAGGAGGGACC
TGACCCTGACCGTGCTGGACATCGTGGCCCTGTTCCCGAACTACGACGTG
AGGACCTACCCGATCCAGACCAGCTCCCAATTAACCCGCGAAATCTACAC
CTCCAGCGTGATCGAGGACAGCCCGGTGTCCGCGAACATCCCGAACGGCT
TCAACCGCGCGGAGTTCGGCGTGAGGCCGCCGCACCTGATGGACTTCATG
AACAGCCTGTTCGTGACCGCCGAGACCGTGAGGTCCCAGACCGTGTGGGG
AGGCCACCTGGTGTCCTCACGCAACACCGCCGGCAACCGCATCAACTTCC
CGTCCTACGGCGTGTTCAACCCGGGCGGCGCCATCTGGATCGCCGACGAG
GACCCGAGGCCGTTCTACCGCACCCTGAGCGACCCGGTGTTCGTGAGGGG

-continued

CGGCTTTGGCAACCCGCACTACGTGCTGGGCCTGAGGGGCGTGGCCTTCC

AGCAGACCGGCACCAACCACACCCGCACCTTCCGCAACAGCGGCACCATC

GACAGCCTGGATGAAATCCCGCCGCAAGACAACTCCGGCGCCCCGTGGAA

CGACTACAGCCACGTATTAAACCACGTGACCTTCGTGAGGTGGCCGGGCG

AAATCTCCGGCAGCGACAGCTGGAGGGCACCGATGTTCTCCTGGACCCAT

CGGTCCGCGACCCCGACCAATACAATCGACCCGGAGAGGATCACCCAGAT

CCCGCTGGTGAAGGCGCACACCCTTCAGAGCGGCACCACCGTGGTGAGGG

GACCGGGCTTCACCGGAGGCGACATCCTGAGGAGGACCTCGGGAGGACCG

TTCGCGTATACTATCGTGAATATAAACGGCCAGCTGCCGCAGCGCTACCG

GGCACGCATCCGCTACGCCAGCACCACCAACCTGAGGATCTACGTGACCG

TGGCGGGGAGAGGATCTTCGCGGGCCAGTTCAACAAGACAATGGACACC

GGAGACCCGCTGACCTTCCAGAGCTTCTCCTACGCCACCATTAATACAGC

GTTCACCTTCCCGATGAGCCAGTCCTCATTCACCGTGGGCGCCGACACCT

TCTCCAGCGGCAACGAGGTGTACATCGACCGCTTCGAGCTGATCCCAGTG

ACCGCCACCCTCGAGTGA

SEQ ID NO:5 shows a polynucleotide sequence, referred to in some places herein as IRDIG.586.35:

ATGGAGAATAATATCCAGAATCAATGCGTGCCGTACAACTGCCTGAATAA

TCCGGAGGTGGAGATATTAAACGAGGAGAGGAGCACCGGGAGGCTGCCGC

TGGACATCTCCCTGTCCCTGACCCGCTTCCTGCTGTCCGAGTTCGTCCCT

GGCGTGGGCGTGGCGTTCGGCCTGTTCGACCTGATCTGGGGCTTCATCAC

CCCGAGCGACTGGAGCCTGTTCCTGCTTCAGATCGAGCAGCTGATCGAGC

AGAGGATCGAGACCCTGGAGAGGAACAGAGCGATCACCACCCTGAGAGGC

CTGGCGGACAGCTATGAAATCTACATCGAGGCGCTGAGGGAGTGGGAGGC

CAACCCGAATAATGCTCAATTAAGGGAGGACGTGAGGATACGCTTCGCGA

ATACAGACGACGCGCTGATCACCGCAATCAATAATTTCACCCTGACCTCC

TTCGAGATCCCGCTGCTGAGCGTGTACGTCCAAGCTGCGAACCTGCACCT

GTCCCTGCTGAGGGACGCCGTGAGCTTTGGCAAGGCTGGGGTCTGGACA

TCGCGACCGTGAATAATCACTACAACAGATTAATCAACCTGATCCACCGC

TACACCAAGCACTGCCTGGACACCTACAATCAAGGCCTGGAGAACCTGAG

GGGCACCAACACAAGGCAGTGGGCGAGGTTCAACCAGTTTAGGAGGGACC

TGACCCTGACCGTGCTGGACATCGTGGCCCTGTTCCCGAACTACGACGTG

AGGACCTACCCGATCCAGACCAGCTCCCAATTAACACGCGAAATCTACAC

CTCCAGCGTGATCGAGGACTCTCCGGTGTCCGCGAACATCCCGAACGGCT

TCAACAGAGCGGAGTTCGGCGTGAGGCCACCGCACCTGATGGACTTCATG

AACAGCCTGTTCGTGACTGCCGAGACCGTGAGGTCCCAGACCGTGTGGGG

AGGCCACCTGGTGTCCTCACGCAACACCGCTGGCAACCGCATCAACTTCC

CGTCCTACGGCGTGTTCAACCCTGGTGGAGCCATCTGGATCGCCGACGAG

GACCCGAGGCCGTTCTACCGCACCCTGAGCGACCCGGTGTTCGTGAGGGG

TGGCTTTGGCAACCCGCACTACGTGCTGGGCCTGAGAGGCGTGGCCTTCC

AGCAGACCGGCACCAACCACACCCGCACCTTCCGCAACAGCGGCACCATC

GACAGCCTGGATGAAATCCCACCGCAAGACAACTCCGGTGCTCCGTGGAA

CGACTACAGCCACGTATTAAACCACGTGACCTTCGTGAGGTGGCCTGGCG

AAATCTCCGGCAGCGACAGCTGGAGGGCACCGATGTTCTCCTGGACCCAT

CGGTCCGCGACCCCGACCAATACAATCGACCCGGAGAGGATCACCCAGAT

CCCGCTGGTGAAGGCGCACACCCTTCAGAGCGGCACCACCGTGGTGAGGG

GACCTGGCTTCACCGGAGGCGACATCCTGAGGAGGACCTCGGGAGGACCG

TTCGCGTATACTATCGTGAATATAAACGGCCAGCTGCCGCAGCGCTACAG

AGCACGCATCCGCTACGCCAGCACCACCAACCTGAGGATCTACGTGACCG

TGGCTGGGGAGAGGATCTTCGCTGGCCAGTTCAACAAGACAATGGACACC

GGAGACCCGCTGACCTTCCAGAGCTTCTCCTACGCCACCATTAATACAGC

GTTCACCTTCCCGATGAGCCAGTCCTCATTCACCGTGGGTGCCGACACCT

TCTCCAGCGGCAACGAGGTGTACATCGACCGCTTCGAGCTGATCCCAGTG

ACCGCCACCCTCGAGTGA

SEQ ID NO:6 shows a polynucleotide sequence, referred to in some places herein as IRDIG.586.36:

ATGGAGAATAATATCCAGAATCAATGCGTGCCGTACAACTGCCTCAATAA

TCCGGAGGTGGAGATATTAAACGAGGAGCGCAGCACCGGCCGCCTCCCGC

TCGACATCTCCCTCTCCCTCACCCGCTTCCTCCTCTCCGAGTTCGTGCCG

GGCGTGGGCGTGGCCTTCGGCCTCTTCGACCTCATCTGGGGCTTCATCAC

CCCGTCCGACTGGTCCCTCTTCCTCCTCCAGATCGAGCAGCTCATCGAGC

AGCGCATCGAGACCCTCGAGCGCAACCGCGCCATCACCACCCTCCGCGGC

CTCGCCGACTCCTATGAAATCTACATCGAGGCCCTCCGCGAGTGGGAGGC

CAACCCGAATAATGCCCAATTAAGGGAGGACGTGCGCATCCGCTTCGCCA

ATACAGACGACGCCCTCATCACCGCAATCAATAATTTCACCCTCACCTCC

TTCGAGATCCCGCTCCTCTCCGTGTACGTGCAGGCCGCCAACCTCCACCT

CTCCCTCCTCCGCGACGCCGTGTCCTTCGGCCAGGGCTGGGGCCTCGACA

TCGCCACCGTGAATAATCACTACAACAGATTAATCAACCTCATCCACCGC

TACACCAAGCACTGCCTCGACACCTACAATCAAGGCCTCGAGAACCTCCG

CGGCACCAACACCCGCCAGTGGGCCCGCTTCAACCAGTTCCGCCGCGACC

TCACCCTCACCGTGCTCGACATCGTGGCCCTCTTCCCGAACTACGACGTG

CGCACCTACCCGATCCAGACCTCCTCCCAATTAACCCGCGAGATCTACAC

CTCCTCCGTGATCGAGGACTCCCCGGTGTCCGCCAACATCCCGAACGGCT

TCAACCGCGCCGAGTTCGGCGTGCGCCCGCCGCACCTCATGGACTTCATG

AACTCCCTCTTCGTGACCGCCGAGACCGTGCGCTCCCAGACCGTGTGGGG

CGGCCACCTCGTGTCCTCCCGCAACACCGCCGGCAACCGCATCAACTTCC

CGTCCTACGGCGTGTTCAACCCGGGCGGCGCCATCTGGATCGCCGACGAG

GACCCGCGCCCGTTCTACCGCACCCTCTCCGACCCGGTGTTCGTGCGCGG

CGGCTTCGGCAACCCGCACTACGTGCTCGGCCTCCGCGGCGTGGCCTTCC

AGCAGACCGGCACCAACCACACCCGCACCTTCCGCAACTCCGGCACCATC

-continued

```
GACTCCCTCGATGAAATCCCGCCGCAGGACAACTCCGGCGCCCCGTGGAA
CGACTACTCCCACGTATTAAACCACGTGACCTTCGTGCGCTGGCCGGGCG
AGATCTCCGGCTCCGACTCCTGGCGCGCGCCGATGTTCTCCTGGACCCAC
CGCTCCGCCACCCCGACCAATACAATCGACCCGGAGCGCATCACCCAGAT
CCCGCTCGTGAAGGCCCACACCCTCCAGTCCGGCACCACCGTGGTGCGCG
GCCCGGGCTTCACCGGCGGCGACATCCTCCGCCGCACCTCCGGCGGCCCG
TTCGCCTATACTATCGTGAATATAAACGGCCAGCTCCCGCAGAGGTACAG
GGCCCGCATCCGCTACGCCTCCACCACCAACCTCCGCATCTACGTGACCG
TGGCCGGCGAGCGCATCTTCGCCGGCCAGTTCAACAAGACGATGGACACC
GGCGACCCGCTCACCTTCCAGTCCTTCTCCTACGCCACCATTAATACAGC
CTTCACCTTCCCGATGTCCCAGTCCTCCTTCACCGTGGGCGCCGACACCT
TCTCCTCAGGCAACGAGGTCTACATCGACCGCTTCGAGCTGATCCCCGTG
ACCGCCACCCTCGAGTGA
```

SEQ ID NO:7 shows a polynucleotide sequence, referred to in some places herein as IRDIG.586.37:

```
ATGGAGAATAATATCCAGAATCAATGCGTGCCGTACAACTGCCTCAATAA
TCCGGAGGTGGAGATATTAAACGAGGAGCGCAGCACCGGACGCCTCCCGC
TCGACATCTCCCTCTCCCTCACCCGCTTCCTCCTCTCCGAGTTCGTGCCT
GGCGTGGGCGTGGCTTTCGGCCTCTTCGACCTCATCTGGGGCTTCATCAC
CCCGTCCGACTGGTCCCTCTTCCTCCTCCAGATCGAGCAGCTCATCGAGC
AGCGCATCGAGACCCTGGAGCGCAACAGAGCCATCACCACCCTCAGAGGC
CTCGCCGACTCCTATGAAATCTACATCGAGGCCCTCCGCGAGTGGGAGGC
CAACCCGAATAATGCCCAATTAAGGGAGGACGTCCGCATCCGCTTCGCCA
ATACAGACGACGCCCTCATCACCGCAATCAATAATTTCACCCTCACCTCC
TTCGAGATCCCGCTCCTCTCCGTGTACGTGCAAGCAGCCAACCTCCACCT
CTCCCTCCTCCGCGACGCCGTGTCGTTCGGCCAAGGCTGGGGTCTCGACA
TCGCCACCGTGAATAATCACTACAACAGATTAATCAACCTCATCCACCGC
TACACCAAGCACTGCCTCGACACCTACAATCAAGGCCTGGAGAACCTCAG
AGGCACCAACACACGCCAGTGGGCACGCTTCAACCAGTTCCGCAGAGACC
TCACCCTCACCGTGCTCGACATCGTGGCCCTCTTCCCGAACTACGACGTC
CGCACCTACCCGATCCAGACCTCCTCCCAATTAACACGCGAAATCTACAC
CTCCTCCGTGATCGAGGACTCTCCGGTGTCCGCCAACATCCCGAACGGCT
TCAACAGAGCCGAGTTCGGCGTGAGGCCACCGCACCTCATGGACTTCATG
AACTCCCTCTTCGTGACAGCCGAGACCGTGCGCTCCCAGACCGTGTGGGG
TGGCCACCTCGTGTCCTCCAGAAACACCGCTGGCAACCGCATCAACTTCC
CGTCCTACGGCGTGTTCAACCCTGGCGGAGCCATCTGGATCGCCGACGAG
GACCCGAGGCCGTTCTACCGCACGCTCTCCGACCCGGTGTTCGTGAGGGG
AGGGTTCGGCAACCCGCACTACGTGCTCGGCCTCAGAGGCGTGGCCTTCC
AGCAGACCGGCACCAACCACACCCGCACCTTCCGCAACTCCGGCACCATC
GACTCCCTCGATGAAATCCCCACCGCAAGACAACTCCGGAGCACCGTGGAA
CGACTACTCCCACGTATTAAACCACGTGACCTTCGTGCGCTGGCCTGGCG
AAATCTCCGGCTCCGACTCCTGGAGGGCACCGATGTTCTCCTGGACCCAC
CGCTCCGCCACCCCGACCAATACAATCGACCCGGAGCGCATCACCCAGAT
CCCGCTCGTGAAGGCCCACACCCTCCAGTCCGGCACCACCGTGGTGAGAG
GCCCTGGCTTCACTGGTGGCGACATCCTCAGACGCACCTCTGGCGGACCG
TTCGCCTATACTATCGTGAATATAAACGGCCAGCTCCCGCAGAGATACAG
AGCACGCATCCGCTACGCCTCCACCACCAACCTCCGCATCTACGTGACCG
TGGCTGGGGAGCGCATCTTCGCTGGCCAGTTCAACAAGACGATGGACACT
GGCGACCCGCTCACCTTCCAGTCCTTCTCCTACGCCACCATTAATACAGC
CTTCACCTTCCCGATGTCCCAGTCCTCCTTCACCGTGGGAGCCGACACCT
TCTCATCCGGCAACGAGGTCTACATCGACCGCTTCGAGCTGATCCCCGTG
ACCGCCACCCTCGAGTGA
```

SEQ ID NO:8 shows a polynucleotide sequence, referred to in some places herein as IRDIG.586.38:

```
ATGGAGAATAATATACAGAATCAATGCGTCCCCTACAACTGCCTCAATAA
TCCTGAAGTAGAGATATTAAACGAAGAGAGGTCGACTGGCAGATTGCCGT
TAGACATCTCCCTGTCCCTTACACGTTTCCTGTTGTCTGAGTTTGTTCCA
GGTGTGGGAGTTGCGTTTGGCCTCTTCGACCTCATCTGGGGCTTCATCAC
TCCATCTGATTGGAGCCTCTTTCTTCTCCAGATTGAACAGTTGATTGAAC
AAAGGATTGAGACCTTGGAAAGGAATCGGGCCATCACTACCCTTCGTGGC
TTAGCAGACAGCTATGAAATCTACATTGAAGCACTAAGAGAGTGGGAAGC
CAATCCTAATAATGCCCAATTAAGAGAAGATGTGCGTATACGCTTTGCTA
ATACAGATGATGCTTTGATCACAGCAATCAATAATTTCACCCTTACCAGC
TTCGAGATCCCTCTTCTCTCGGTCTATGTTCAAGCTGCTAACCTGCACTT
GTCACTACTGCGCGACGCTGTGTCGTTTGGGCAAGGTTGGGGACTGGACA
TAGCTACTGTCAATAATCACTACAACAGATTAATCAATCTGATTCATCGA
TACACGAAACATTGTTTGGATACCTACAATCAAGGATTGGAGAACCTGAG
AGGTACTAACACTCGCCAATGGGCCAGGTTCAATCAGTTCAGGAGAGACC
TTACACTTACTGTGTTAGACATAGTTGCTCTCTTTCCGAACTACGATGTT
CGTACCTATCCGATTCAAACGTCATCCCAATTAACAAGGGAGATCTACAC
CAGTTCAGTCATTGAAGACTCTCCAGTTTCTGCGAACATACCCAATGGTT
TCAACAGGGCTGAGTTTGGAGTCAGACCACCCCATCTCATGGACTTCATG
AACTCTTTGTTTGTGACTGCAGAGACTGTTAGATCCCAAACTGTGTGGGG
AGGACACTTAGTTAGCTCACGCAACACGGCTGGCAATCGTATCAACTTTC
CTAGTTACGGGGTCTTCAATCCCGGGGCGCCATCTGGATTGCAGATGAA
GATCCACGTCCTTTCTATCGGACCTTGTCAGATCCTGTCTTCGTCCGAGG
AGGCTTTGGCAATCCTCACTATGTACTCGGTCTTAGGGGAGTGGCCTTTC
AACAAACTGGTACGAATCACACCCGCACATTCAGGAACTCCGGGACCATT
GACTCTCTAGATGAAATACCCTCAAGACAACAGCGGCGCACCTTGGAA
TGACTACTCCCATGTATTAAATCATGTTACCTTTGTGCGCTGGCCAGGTG
```

AGATCTCAGGTTCCGACTCATGGAGAGCACCAATGTTCTCTTGGACGCAT

CGTAGCGCTACCCCCACAAATACAATTGATCCAGAGAGAATCACTCAGAT

TCCCTTGGTGAAGGCACACACACTTCAGTCAGGAACTACAGTTGTAAGAG

GGCCGGGGTTCACGGGAGGAGACATTCTTCGACGCACTAGTGGAGGACCA

TTCGCGTATACTATTGTCAATATAAATGGGCAACTTCCCCAAAGGTATCG

TGCCAGGATACGCTATGCCTCTACTACCAATCTAAGAATCTACGTTACGG

TTGCAGGTGAACGGATCTTTGCTGGTCAGTTCAACAAGACAATGGATACC

GGTGATCCACTTACATTCCAATCTTTCTCCTACGCCACGATTAATACAGC

GTTCACCTTTCCAATGAGCCAGAGCAGTTTCACAGTAGGTGCTGATACCT

TCAGTTCAGGCAACGAAGTGTACATTGACAGGTTTGAGTTGATTCCAGTT

ACTGCCACACTCGAGTGA

SEQ ID NO:9 shows a polynucleotide sequence, referred to in some places herein as IRDIG.586.39:

ATGGAGAATAATATACAGAATCAATGCGTCCCCTACAACTGCCTCAATAA

TCCTGAAGTCGAGATATTAAACGAAGAGAGGTCCACTGGCAGATTGCCGT

TGGACATCTCCCTGTCCCTTACACGCTTCCTGTTGTCTGAGTTTGTTCCT

GGTGTGGGAGTTGCGTTTGGCCTCTTCGACCTCATCTGGGGATTCATCAC

TCCATCTGATTGGAGCCTCTTTCTTCTCCAGATTGAACAGTTGATTGAAC

AAAGGATTGAGACCTTGGAAAGGAATAGAGCCATCACTACCCTTAGAGGC

CTCGCAGACAGCTATGAAATCTACATTGAAGCACTCAGAGAGTGGGAAGC

CAATCCCAATAATGCCCAATTAAGAGAAGATGTGCGGATACGCTTTGCTA

ATACAGATGATGCTTTGATCACAGCAATCAATAATTTCACCCTTACCAGC

TTCGAGATCCCTCTTCTCTCGGTCTATGTTCAAGCTGCTAACCTGCACTT

GTCACTCCTGCGCGACGCTGTGTCGTTTGGGCAAGGTTGGGGACTGGACA

TAGCTACTGTCAATAATCACTACAACAGATTAATCAATCTGATTCATCGC

TACACGAAACACTGCTTGGATACCTACAATCAAGGATTGGAGAACCTGAG

AGGCACTAACACTCGCCAATGGGCGAGGTTCAATCAGTTTAGGAGAGACC

TTACACTTACTGTGCTCGACATAGTTGCTCTCTTTCCGAACTACGATGTT

CGCACCTATCCGATTCAAACGTCATCCCAATTAACAAGGGAGATTTACAC

CAGCTCAGTCATTGAGGACTCTCCAGTTTCTGCGAACATACCCAATGGTT

TCAACAGAGCTGAGTTTGGAGTCAGACCACCCCATCTCATGGACTTCATG

AACTCTCTCTTTGTGACTGCCGAGACTGTTAGATCCCAAACTGTGTGGGG

AGGACACCTCGTTAGCTCACGCAACACGGCTGGCAATCGCATCAACTTTC

CTTCCTACGGGTGTTCAATCCTGGAGGTGCCATCTGGATTGCAGATGAA

GATCCACGCCCTTTCTATCGGACCTTGTCAGATCCTGTGTTCGTCAGAGG

AGGCTTTGGCAATCCTCACTATGTCCTCGGTCTTAGGGGAGTGGCCTTTC

AACAAACTGGCACGAATCACACCCGCACATTCCGCAACTCCGGGACCATT

GACTCCCTTGATGAAATACCACCTCAAGACAACTCCGGTGCGCCTTGGAA

TGACTACTCCCATGTATTAAATCATGTTACCTTTGTGCGCTGGCCTGGTG

AAATCTCCGGTTCCGACTCATGGAGAGCACCAATGTTCTCTTGGACGCAT

CGCAGCGCTACCCCCACAAATACAATCGATCCAGAGAGAATCACTCAGAT

TCCCTTGGTGAAGGCACACACACTTCAGTCGGGAACTACAGTTGTCAGAG

GACCTGGGTTCACGGGAGGAGACATTCTTAGGCGCACCAGCGGAGGACCA

TTCGCGTATACTATTGTCAATATAAATGGGCAACTTCCCCAACGCTATAG

AGCGAGGATACGCTATGCCTCTACTACCAATCTTAGAATCTACGTTACGG

TCGCTGGTGAACGGATCTTTGCTGGTCAGTTCAACAAGACAATGGATACT

GGTGATCCACTTACATTCCAATCTTTCTCCTACGCCACGATTAATACAGC

GTTCACCTTTCCAATGAGCCAGAGCAGCTTCACAGTCGGTGCTGATACCT

TCTCATCTGGCAACGAAGTGTACATTGACCGCTTTGAGTTGATTCCAGTT

ACTGCCACACTGGAGTAA

SEQ ID NO:10 shows a polynucleotide sequence, referred to in some places herein as IRDIG.586.40:

ATGGAGAATAATATCCAGAATCAATGCGTGCCTTACAATTGTCTCAATAA

TCCCGAGGTGGAGATATTAAACGAGGAGAGATCCACTGGCAGACTGCCAC

TCGACATATCCTTGTCCCTTACCCGTTTCCTTTTGAGCGAATTTGTTCCT

GGTGTGGGAGTGGCTTTCGGACTGTTCGATCTGATATGGGGCTTTATCAC

TCCTTCTGATTGGAGCCTCTTCCTTCTCCAGATTGAGCAATTGATTGAGC

AGAGAATAGAAACCTTGGAAAGGAACCGTGCAATCACGACCTTGCGCGGT

CTCGCCGATAGCTATGAAATCTACATTGAAGCACTGAGGGAGTGGGAGGC

CAACCCCAATAATGCTCAATTAAGGGAAGATGTGCGTATTCGTTTTGCTA

ATACAGACGACGCTCTCATCACAGCAATCAATAATTTCACACTTACATCC

TTTGAAATCCCGCTTTTGAGCGTGTACGTTCAAGCCGCCAATCTCCACCT

CTCACTTCTGAGGGACGCTGTCTCCTTTGGGCAAGGTTGGGGACTGGATA

TCGCTACTGTGAATAATCACTACAATAGATTAATCAACCTGATTCATAGA

TATACGAAGCACTGCTTGGACACATACAATCAAGGACTGGAGAACCTTAG

GGGAACTAACACTAGGCAGTGGGCAAGGTTCAACCAGTTCAGACGTGATC

TCACACTTACTGTGCTGGATATCGTTGCTCTCTTTCCGAACTACGATGTT

CGCACCTACCCAATCCAGACGTCATCCCAATTAACAAGGGAAATCTACAC

CTCCTCAGTGATTGAGGACTCTCCCGTTTCTGCTAACATACCTAACGGCT

TCAACCGCGCCGAGTTCGGAGTTAGACCGCCCCACCTTATGGACTTTATG

AATAGCTTGTTCGTGACTGCTGAGACTGTTAGAAGCCAAACTGTGTGGGG

CGGCCACTTGGTCAGCTCACGCAACACGGCTGGCAACCGTATCAACTTCC

CGTCTTACGGGGTCTTTAACCCTGGTGGCGCCATTTGGATTGCAGACGAG

GACCCACGTCCTTTTTACCGCACCCTGTCAGATCCGGTTTTCGTCAGAGG

CGGATTTGGGAATCCTCATTATGTCCTGGGCCTTAGGGGAGTGGCTTTCC

AACAGACTGGCACCAACCACACCCGTACGTTTCGCAATAGCGGGACCATA

GATTCTCTTGATGAAATCCCACCTCAAGATAACAGCGGCGCACCTTGGAA

CGATTATTCCCACGTATTAAATCACGTTACGTTCGTCCGCTGGCCGGGTG

AGATCAGCGGCAGCGATTCATGGAGAGCACCAATGTTCTCTTGGACGCAC

CGTTCAGCCACCCCCTACAAATACAATTGACCCGGAGAGGATTACTCAAAT

CCCATTGGTCAAAGCACATACACTTCAGTCTGGGACCACCGTGGTCAGAG

GGCCTGGGTTCACGGGAGGAGACATTCTTAGGCGCACATCCGGAGGACCC

TTCGCTTATACTATCGTTAATATAAATGGGCAGCTCCCCCAGCGCTATCG

TGCCAGAATCCGTTACGCCTCTACTACAAATCTCAGAATCTACGTGACGG

TTGCCGGTGAGCGCATCTTTGCTGGTCAGTTTAACAAGACGATGGATACT

GGCGACCCACTGACATTCCAATCTTTCTCATACGCAACTATTAATACAGC

TTTCACATTCCCAATGAGCCAGTCATCTTTCACCGTCGGTGCTGATACCT

TCAGCTCTGGCAACGAAGTCTATATCGACAGATTTGAGTTGATTCCAGTT

ACTGCAACGCTCGAGTGA

SEQ ID NO:11 shows a polynucleotide sequence, referred to in some places herein as IRDIG.586.41:

ATGGAGAATAATATCCAGAATCAATGCGTGCCTTACAACTGTCTCAATAA

TCCCGAGGTGGAGATATTAAACGAGGAGAGATCCACTGGCAGACTGCCAC

TCGACATATCCTTGTCCCTTACCCGCTTCCTTTTGAGCGAATTTGTTCCT

GGTGTGGGAGTGGCTTTCGGACTGTTCGATCTGATATGGGCTTTATCAC

TCCTTCTGATTGGAGCCTCTTCCTTCTCCAGATTGAGCAGTTGATTGAGC

AGAGAATAGAAACCTTGGAAAGGAATCGGGCAATCACGACCTTGAGGGGT

CTCGCCGATAGCTATGAAATCTACATTGAAGCACTGAGGGAGTGGGAGGC

CAACCCCAATAATGCTCAATTAAGGGAAGATGTGCGGATTCGCTTTGCTA

ATACAGACGACGCTCTCATCACAGCAATCAATAATTTCACACTTACATCC

TTTGAAATCCCGCTTTTGAGCGTGTACGTTCAAGCAGCCAATCTCCACCT

CTCACTTCTGAGGGACGCTGTCTCCTTTGGGCAAGGTTGGGGACTGGATA

TCGCTACTGTGAATAATCACTACAATAGATTAATCAACCTGATTCATAGA

TATACGAAGCACTGCTTGGACACATACAATCAAGGACTGGAGAACCTTAG

GGGAACTAACACTAGGCAGTGGGCAAGGTTCAACCAGTTCAGACGCGATC

TCACACTTACTGTGCTGGATATCGTTGCTCTCTTTCCGAACTACGATGTT

CGCACCTACCCAATCCAGACGTCATCCCAATTAACAAGGGAAATCTACAC

CTCCTCAGTGATTGAGGACTCTCCCGTTTCTGCTAACATACCTAACGGCT

TCAACAGAGCCGAGTTCGGAGTTAGACCACCCCACCTTATGGACTTTATG

AATAGCTTGTTCGTGACTGCTGAGACTGTTAGAAGCCAAACTGTGTGGGG

TGGCCACTTGGTCAGCTCACGCAACACGGCTGGCAACCGCATCAACTTCC

CGTCTTACGGGGTCTTTAACCCTGGTGGAGCCATTTGGATTGCAGACGAG

GACCCACGCCCTTTTTACCGCACCCTGTCAGATCCGGTTTTCGTCAGAGG

CGGATTTGGGAATCCTCATTATGTCCTGGGCCTTAGGGGAGTGGCTTTCC

AACAGACTGGCACCAACCACACCCGCACGTTTCGCAATAGCGGGACCATA

GATTCTCTTGATGAAATCCCACCTCAAGATAACAGCGGAGCACCTTGGAA

CGATTATTCCCACGTATTAAATCACGTTACGTTCGTCCGCTGGCCTGGTG

AGATCAGCGGCAGCGATTCATGGAGAGCACCAATGTTCTCTTGGACGCAC

CGCTCAGCCACCCCTACAAATACAATCGACCCGGAGAGGATTACTCAAAT

CCCATTGGTCAAAGCACATACACTTCAGTCTGGGACCACCGTGGTCAGAG

GGCCTGGGTTCACGGGAGGAGACATTCTTAGGCGCACATCCGGAGGACCC

TTCGCTTATACTATCGTTAATATAAATGGGCAGCTCCCCCAGCGCTATAG

AGCCAGAATCCGCTACGCCTCTACTACAAATCTCAGAATCTACGTGACGG

TTGCCGGTGAGCGCATCTTTGCTGGTCAGTTTAACAAGACGATGGATACT

GGCGACCCACTGACATTCCAATCTTTCTCATACGCAACTATTAATACAGC

TTTCACATTCCCAATGAGCCAGTCATCTTTCACCGTCGGTGCTGATACCT

TCAGCTCTGGCAACGAAGTCTATATCGACAGATTTGAGTTGATTCCAGTT

ACTGCAACGCTCGAGTGA

SEQ ID NO:12 shows a polynucleotide sequence, referred to in some places herein as IRDIG.586.42:

ATGGAGAATAATATCCAGAATCAATGTGTCCCATACAACTGCCTCAATAA

TCCTGAAGTTGAGATATTAAACGAAGAGAGGAGCACTGGACGCCTTCCCC

TTGACATCTCCCTCTCCCTCACAAGGTTCCTCTTGTCTGAGTTTGTTCCT

GGTGTGGGTGTGGCCTTTGGCCTCTTTGACCTCATCTGGGGATTCATCAC

CCCATCTGATTGGAGCCTCTTCCTTCTCCAGATTGAACAGTTGATTGAGC

AGAGGATTGAGACCCTTGAAAGGAACAGAGCCATCACCACACTTAGAGGC

CTTGCTGACAGCTATGAAATCTACATTGAAGCACTGAGGGAGTGGGAAGC

CAATCCCAATAATGCTCAATTAAGGGAAGATGTGAGGATTCGCTTTGCCA

ATACAGATGACGCTTTGATCACAGCAATCAATAATTTCACCCTCACCAGC

TTTGAGATCCCTTTGCTCTCAGTCTATGTTCAAGCTGCAAACCTCCACTT

GAGCTTGCTTAGGGATGCTGTGTCGTTCGGACAAGGTTGGGGACTTGACA

TAGCCACTGTCAATAATCACTACAACAGATTAATCAACTTGATTCATCGC

TACACCAAACATTGCTTGGACACCTACAATCAAGGATTGGAGAACCTCAG

AGGCACCAACACTCGCCAATGGGCAAGGTTCAACCAGTTTAGAAGGGATC

TCACACTCACTGTGCTTGACATAGTTGCTCTCTTCCCCAACTATGATGTT

CGCACCTACCCAATTCAAACCAGCTCCCAATTAACAAGGGAAATCTACAC

CTCCTCAGTCATTGAGGACAGCCCAGTTTCTGCCAACATACCCAATGGTT

TCAATAGGGCTGAGTTTGGTGTCAGACCACCCCATCTCATGGACTTCATG

AACTCCTTGTTCGTGACTGCCGAGACTGTTAGGTCCCAAACTGTGTGGGG

AGGCCACCTTGTTAGCTCCCGCAACACCGCTGGCAACCGCATCAACTTCC

CATCCTATGGGTTTTCAATCCTGGTGGAGCCATCTGGATTGCAGATGAG

GACCCAAGGCCTTTCTACAGAACCTTGTCAGATCCTGTCTTTGTCAGAGG

AGGCTTTGGCAATCCACACTATGTTCTTGGTTTGAGGGGAGTGGCTTTTC

AGCAGACTGGCACCAATCACACCCGCACATTCAGAAACAGCGGCACCATT

GACAGCTTGATGAAATCCCACCTCAAGACAACAGCGGAGCACCCTGGAA

CGACTACTCCCATGTATTAAATCATGTCACCTTTGTGCGCTGGCCTGGTG

AGATCAGCGGTTCAGATTCTTGGAGAGCACCAATGTTCTCATGGACCCAT

CGCTCTGCCACACCCACAAATACAATAGATCCAGAGAGAATCACCCAGAT

TCCCTTGGTGAAGGCACACACACTTCAGTCTGGAACCACAGTTGTCAGAG

GGCCTGGGTTCACTGGTGGAGACATTCTCAGACGCACCTCTGGAGGGCCA

-continued

TTTGCTTATACTATTGTCAATATAAATGGGCAACTTCCCCAACGCTACAG

AGCCAGAATCCGCTATGCTTCCACCACTAACTTGAGAATCTATGTCACAG

TTGCTGGTGAAAGGATCTTTGCTGGTCAGTTCAACAAGACAATGGACACT

GGTGATCCATTGACATTCCAGTCATTCTCCTATGCCACCATTAATACAGC

CTTCACCTTTCCAATGAGCCAGTCCAGCTTCACAGTGGGTGCAGATACCT

TCAGCTCCGGCAATGAGGTGTACATTGACCGCTTTGAGTTGATTCCAGTG

ACTGCCACACTCGAGTGA

SEQ ID NO:13 shows a polynucleotide sequence, referred to in some places herein as IRDIG.586.43:

ATGGAGAATAATATCCAGAATCAATGCGTGCCCTACAACTGTCTGAATAA

TCCGGAGGTGGAGATATTAAACGAAGAGCGCTCAACGGGGAGGCTCCCGC

TGGACATATCCCTGTCGCTTACCCGGTTCCTCTTGTCCGAGTTCGTTCCG

GGTGTGGGCGTGGCGTTCGGACTCTTTGATCTCATCTGGGGCTTCATAAC

CCCCTCTGATTGGAGCCTGTTCCTCCTCCAGATCGAGCAGCTGATCGAGC

AGAGGATAGAGACATTGGAGAGGAACCGGGCAATCACCACGCTTAGGGGA

CTCGCAGATAGCTATGAAATCTACATTGAAGCCCTGCGCGAGTGGGAAGC

CAACCCGAATAATGCACAATTAAGGGAGGATGTGAGGATTCGCTTTGCCA

ATACAGACGACGCTCTGATAACGGCAATCAATAATTTCACACTTACCAGC

TTTGAGATCCCCCTTCTGTCGGTCTATGTTCAAGCTGCGAACCTGCACCT

GTCACTGCTCAGAGACGCTGTCTCGTTCGGCCAAGGCTGGGGACTGGACA

TCGCTACCGTGAATAATCATTACAACAGATTAATCAACCTTATTCACAGA

TACACGAAACATTGCTTGGACACATACAATCAAGGGCTGGAAAACCTGAG

GGGCACTAACACTCGCCAGTGGGCCAGATTCAACCAGTTTCGGAGGGATC

TCACCCTTACTGTGCTTGATATCGTCGCCCTTTTCCCGAACTACGATGTT

CGGACCTACCCAATTCAGACGTCATCCCAATTAACAAGGGAAATCTACAC

CAGCTCCGTCATTGAAGATTCTCCAGTTTCCGCTAACATCCCTAACGGTT

TCAACCGCGCAGAGTTCGGCGTGAGGCCACCCCATCTCATGGACTTCATG

AACTCTTTGTTCGTCACTGCCGAGACCGTTAGAAGCCAGACGGTGTGGGG

CGGACACCTCGTGTCCTCACGCAACACTGCTGGCAACCGGATCAACTTCC

CCTCCTACGGGGTTTTCAACCCTGGTGGAGCCATCTGGATTGCGGACGAG

GACCCACGCCCTTTCTACCGGACCTTGTCAGACCCTGTCTTTGTCAGAGG

AGGGTTCGGCAACCCGCATTATGTCCTGGGCCTCAGAGGCGTCGCGTTTC

AGCAGACCGGCACGAACCACACCCGGACGTTCCGGAACAGCGGGACCATC

GACTCCCTGGATGAAATCCCACCGCAAGACAACAGCGGCGCTCCCTGGAA

CGACTACAGCCATGTATTAAACCACGTGACCTTTGTCCGCTGGCCTGGTG

AGATTTCGGGCAGCGACTCATGGAGGGCACCCATGTTCTCTTGGACGCAC

CGCTCGGCCACCCCTACCAATACAATCGATCGGAGAGGATTACTCAGAT

CCCGCTCGTGAAGGCCCACACCCTTCAGTCCGGAACTACTGTTGTGAGGG

GTCCTGGGTTTACGGGTGGCGATATTCTTAGGCGCACCTCCGGCGGACCA

TTCGCCTATACTATTGTCAATATAAACGGGCAACTGCCCCAGAGATATAG

AGCACGCATCCGCTACGCCTCTACTACAAACCTGAGGATCTACGTGACGG

TTGCCGGTGAGCGGATCTTCGCTGGCCAGTTCAACAAGACAATGGACACT

GGCGACCCACTCACATTCCAATCATTCTCCTACGCGACCATTAATACAGC

GTTTACATTCCCAATGAGCCAGTCTAGCTTCACCGTGGGTGCGGACACGT

TTTCGTCTGGGAACGAGGTCTACATCGACCGCTTTGAGTTGATCCCAGTG

ACCGCGACACTCGAGTGA

SEQ ID NO:14 shows a polynucleotide sequence, referred to in some places herein as Cry1F trunc Hx:

ATGGAGAACAACATACAGAATCAGTGCGTCCCCTACAACTGCCTCAACAA

TCCTGAAGTAGAGATTCTCAACGAAGAGAGGTCGACTGGCAGATTGCCGT

TAGACATCTCCCTGTCCCTTACACGTTTCCTGTTGTCTGAGTTTGTTCCA

GGTGTGGGAGTTGCGTTTGGCCTCTTCGACCTCATCTGGGGCTTCATCAC

TCCATCTGATTGGAGCCTCTTTCTTCTCCAGATTGAACAGTTGATTGAAC

AAAGGATTGAGACCTTGGAAAGGAATCGGGCCATCACTACCCTTCGTGGC

TTAGCAGACAGCTATGAGATCTACATTGAAGCACTAAGAGAGTGGGAAGC

CAATCCTAACAATGCCCAACTGAGAGAAGATGTGCGTATACGCTTTGCTA

ACACAGATGATGCTTTGATCACAGCCATCAACAACTTCACCCTTACCAGC

TTCGAGATCCCTCTTCTCTCGGTCTATGTTCAAGCTGCTAACCTGCACTT

GTCACTACTGCGCGACGCTGTGTCGTTTGGGCAAGGTTGGGGACTGGACA

TAGCTACTGTCAACAATCACTACAACAGACTCATCAATCTGATTCATCGA

TACACGAAACATTGTTTGGATACCTACAATCAGGGATTGGAGAACCTGAG

AGGTACTAACACTCGCCAATGGGCCAGGTTCAATCAGTTCAGGAGAGACC

TTACACTTACTGTGTTAGACATAGTTGCTCTCTTTCCGAACTACGATGTT

CGTACCTATCCGATTCAAACGTCATCCCAACTTACAAGGGAGATCTACAC

CAGTTCAGTCATTGAAGACTCTCCAGTTTCTGCGAACATACCCAATGGTT

TCAACAGGGCTGAGTTTGGAGTCAGACCACCCCATCTCATGGACTTCATG

AACTCTTTGTTTGTGACTGCAGAGACTGTTAGATCCCAAACTGTGTGGGG

AGGACACTTAGTTAGCTCACGCAACACGGCTGGCAATCGTATCAACTTTC

CTAGTTACGGGGTCTTCAATCCCGGGGCGCCATCTGGATTGCAGATGAA

GATCCACGTCCTTTCTATCGGACCTTGTCAGATCCTGTCTTCGTCCGAGG

AGGCTTTGGCAATCCTCACTATGTACTCGGTCTTAGGGGAGTGGCCTTTC

AACAAACTGGTACGAATCACACCCGCACATTCAGGAACTCCGGGACCATT

GACTCTCTAGATGAGATACCCCTCAAGACAACAGCGGCGCACCTTGGAA

TGACTACTCCCATGTGCTGAATCATGTTACCTTTGTGCGCTGGCCAGGTG

AGATCTCAGGTTCCGACTCATGGAGAGCACCAATGTTCTCTTGGACGCAT

CGTAGCGCTACCCCCACAAACACCATTGATCCAGAGAGAATCACTCAGAT

TCCCTTGGTGAAGGCACACACACTTCAGTCAGGAACTACAGTTGTAAGAG

GGCCGGGGTTCACGGGAGGAGACATTCTTGACGCACTAGTGGAGGACCA

TTCGCGTACACCATTGTCAACATCAATGGGCAACTTCCCAAAGGTATCG

TGCCAGGATACGCTATGCCTCTACTACCAATCTAAGAATCTACGTTACGG

-continued

```
TTGCAGGTGAACGGATCTTTGCTGGTCAGTTCAACAAGACAATGGATACC

GGTGATCCACTTACATTCCAATCTTTCTCCTACGCCACTATCAACACCGC

GTTCACCTTTCCAATGAGCCAGAGCAGTTTCACAGTAGGTGCTGATACCT

TCAGTTCAGGCAACGAAGTGTACATTGACAGGTTTGAGTTGATTCCAGTT

ACTGCCACACTCGAGTAA
```

SEQ ID NOs:15-29 show exemplary primers and probes utilized in certain embodiments herein.

DETAILED DESCRIPTION

I. Overview of Several Embodiments

Provided herein are compositions and methods to engineer synthetic genes for increased expression of the encoded protein products thereof. Disclosed herein is the unexpected and generally applicable discovery that heterologous protein expression may be increased in a plant cell by engineering the nucleotide sequence of the synthetic gene to include polyadenylation sequences that are present in the native gene. In some embodiments, the polyadenylation sequences are included in the synthetic gene in the same number, and in the same location(s), as they are present in the native gene. It has been surprisingly and unexpectedly found in some examples that such synthetic genes demonstrate an increase in average protein expression in V5 leaf tissue (e.g., of from about 0.5-fold to about 17-fold), when compared to synthetic genes designed utilizing conventional approaches.

A synthetic polynucleotide encoding a polypeptide may be engineered by a process comprising, for example and without limitation: substituting rare codons with preferred codons (e.g., most-preferred codons); removal of known destabilization factors; removal of sequences predicted to form secondary stem loop structures; removal of unintended open reading frames; and removal of unwanted internal restriction enzyme recognition sequences. In embodiments herein, the resulting polynucleotide encoding a polypeptide is additionally modified to include at least one specific polyadenylation sequence that is present in a native gene encoding the same polypeptide at the identical nucleotide position, for example, so as to maintain the location and total number of the specified polyadenylation sequences.

Specific examples herein demonstrate the foregoing discovery in maize with nine different genes encoding insecticidal Bt proteins, and a glyphosate tolerance gene. In particular examples herein, the foregoing methods and compositions are utilized to engineer a synthetic polynucleotide to express a heterologous polypeptide in a crop plant (e.g., corn and soya). For example, the expression of three configurations of a truncated cry1Ab gene was evaluated in transgenic maize at the $T_0$ generation. It was determined that one of the cry1Ab polynucleotides, wherein native polyadenylation sequences had been preserved, produced stable Cry1Ab protein at a significantly higher level than the other polynucleotides that were evaluated. By way of further example, the expression of twelve configurations of a truncated cry1Fa gene was also evaluated in maize at the $T_0$ generation. Two cry1Fa polynucleotides produced stable Cry1Fa protein at a significantly higher level than all of the other polynucleotides that were evaluated.

II. Abbreviations

Bt *Bacillus thuringiensis*
corn earworm CEW
ECB European corn borer
FAW fall armyworm
GFP green fluorescent protein
NCBI National Center for Biotechnology Information
PCR polymerase chain reaction
rECB Cry1Fa-resistant European corn borer

III. Terms

Use of the singular forms "a," "an," and "the" include plural references unless the context clearly dictates otherwise. For example, reference to "a polynucleotide" includes a plurality of polynucleotides, reference to "a substrate" includes a plurality of such substrates, reference to "a variant" includes a plurality of such variants, etc.

Where a range of values is recited, it is to be understood that each intervening integer value, and each fraction thereof, between the recited upper and lower limits of that range is also specifically disclosed, along with each subrange between such values. The upper and lower limits of any range can independently be included in, or excluded from, the range, and each range where either, neither, or both limits are included is also encompassed within the invention. Where a value being discussed has inherent limits (for example, where a component can be present at a concentration of from 0 to 100%, or where the pH of an aqueous solution can range from 1 to 14), those inherent limits are specifically disclosed.

Where a value is explicitly recited, it is to be understood that values which are about the same quantity or amount as the recited value are also within the scope of the invention. Where a combination is disclosed, each subcombination of the elements of that combination is also specifically disclosed, and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly, or in any combination with the other alternatives, are also hereby disclosed (more than one element of an invention can have such exclusions, and all combinations of elements having such exclusions are hereby disclosed).

Unless otherwise provided, all technical and scientific terms used herein have the same meaning as commonly understood by one of ordinary skill in the art of genetics, bioinformatics, and gene design. General dictionaries containing many of the terms used in this disclosure are: Singleton et al. (1994) *Dictionary of Microbiology and Molecular Biology,* 2nd Ed., John Wiley and Sons, New York; and Hale and Marham (1991) *The Harper Collins Dictionary of Biology*, Harper Perennial, New York. Any methods and materials similar or equivalent to those described herein may be used in the practice or testing of embodiments of the invention, though certain methods and materials are exemplified by those disclosed herein.

Codon usage bias: As used herein, the term "codon usage bias," or simply "codon usage," refers to the high-frequency preferential use of a particular codon (as opposed to other, synonymous codons) coding for an amino acid within an organism. A codon usage bias may be expressed as a quantitative measurement of the rate at which a particular codon is used in the genome of a particular organism, for example, when compared to other codons that encode the same amino acid.

Various methods are known to those of skill in the art for determining codon usage bias. In some embodiments, codon usage bias may be determined by the codon adaptation index (CAI) method, which is essentially a measurement of the distance of a gene's codon usage to the codon usage of a predefined set of highly-expressed genes. Sharp and Li (1987) Nucleic Acids Res. 15:1281-95. Alternative methods for determining a codon usage bias include MILC (measure independent of length and composition) (Supek and Vlahovicek (2005) BMC Bioinformatics 6:182) and relative synonymous codon usage (RSCU), which is the observed frequency of a particular codon divided by the frequency expected from equal usage of all the synonymous codons for that amino acid. Sharp et al. (1986) Nucleic Acids Res. 14:5125-43. RSCU values close to 1.0 indicate a lack of bias for the particular codon, whereas departure from 1.0 reflects codon usage bias.

Thus, codon usage bias includes the relative frequencies of use of codons that encode the same amino acid ("synonymous codons"). A bias may be naturally occurring; for example, the codon bias in an organism's genome reflects the relative overall use of synonymous codons within all the genes in that organism. A bias may also be used in a computational algorithm, where, for example, it may be used to determine the relative frequency with which different synonymous codons are selected for use in designing a polynucleotide sequence. Similarly, the "relative" frequency of any sequence element used to encode a polypeptide within a nucleotide sequence is the frequency with which that sequence element is used to encode a feature of the polypeptide, divided by the number of occurrences within the polypeptide in a given reading frame of features that could be encoded by that sequence element.

Codon usage bias may also be inferred from a codon usage table for a particular expression host organism. Codon usage tables are readily available for many expression host organisms. See, e.g., Nakamura et al. (2000) Nucleic Acids Res. 28:292 (Codon Usage Database—updated versions available at kazusa.or.jp/codon). When a codon usage table is not available, it may be assembled from public organismal genetic databases, such as those maintained by NCBI (available at ncbi.nlm.nih.gov/sites/genome). In some embodiments, a codon usage table may be assembled from a set of coding regions obtained from the particular expression host organism. In some examples, a set of coding regions comprises at least 100, at least 200, at least 300, at least 400, at least 500, at least 550, at least 600, or more coding regions obtained from the particular expression host organism.

The terms "codon usage table," or "codon bias table," or "codon frequency table" are used interchangeably and describe a table which correlates each codon that may be used to encode a particular amino acid with the frequencies with which each codon is used to encode that amino acid in a specific organism, within a specified class of genes within that organism, or within one or more synthetic polynucleotides.

Absolute codon frequency: As used herein, the term "absolute codon frequency" refers to the frequency with which a codon appears relative to the total number of codons (e.g., both synonymous and non-synonymous codons) within a polynucleotide or set of polynucleotides in a given reading frame (e.g., a reading frame that is used to encode a polypeptide of interest). Similarly, the "absolute" frequency of any sequence element used to encode a polypeptide within a polynucleotide is the frequency with which that sequence element is used to encode a feature (e.g., amino acid, amino acid pair, etc.) of the polypeptide, divided by the number of occurrences within the polypeptide of features of the same size as those that could be encoded by that sequence element.

As used herein with regard to codon bias and codon frequency, a "rare codon" is a codon that has a usage of less than 10% in the organism of interest. In some examples, a "rare codon" is a codon that has a usage of less than 5% in the organism. As used herein, a "preferred codon" is a codon that has a usage of more than 5% in the organism of interest. In some examples, a "most preferred codon" is a codon that has a usage of more than 10% in the organism, for example, the codon with the highest usage in the organism for the coding of a particular amino acid.

Codon space: As used herein, the term "codon space" refers to all of the possible polynucleotide sequences that can be used to encode a specific polypeptide, by varying the codons used to encode amino acids within the polypeptide.

Codon substitution: As used herein, the term "codon substitution" refers to the altering of a nucleotide coding sequence by changing one or more of the codons encoding one or more amino acids of an encoded polypeptide, without altering the amino acid sequence of the encoded polypeptide.

Codon optimization: As used herein, the term "codon optimization" refers to processes employed to modify an existing coding sequence, or to design a coding sequence in the first instance, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism. Codon optimization also includes, for example, the process sometimes referred to as "codon harmonization," wherein codons of a codon sequence that are recognized as low-usage codons in the source organism are altered to codons that are recognized as low-usage in the new expression host. This process may help expressed polypeptides to fold normally by introducing natural and appropriate pauses during translation/extension. Birkholtz et al. (2008) Malaria J. 7:197-217.

It will be understood that, due to the redundancy of the genetic code, multiple DNA sequences may be designed to encode a single amino acid sequence. Thus, optimized DNA sequences may be designed, for example, to remove superfluous restriction sites and undesirable RNA secondary structures, while optimizing the nucleotide sequence of the coding region so that the codon composition resembles the overall codon composition of the host in which the DNA is to be expressed. Guidance regarding the design and production of synthetic DNA sequences can be found in, for example, PCT International Patent Application Nos. WO 2013016546, WO 2011146524, and WO 1997013402; and U.S. Pat. Nos. 6,166,302 and 5,380,831.

Modify: As used herein, the terms "modify" or "alter," or any forms thereof, mean to modify, alter, replace, delete, substitute, remove, vary, or transform.

Backcrossing: Backcrossing methods may be used to introduce a nucleic acid sequence into plants. The backcrossing technique has been widely used for decades to introduce new traits into plants. Jensen, N., Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; and polyadenylation recognition sequences. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell. A "plant promoter" may be a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters. A "constitutive" promoter is a promoter which may be active in most cells of the organism under most environmental conditions.

Any inducible promoter can be used in some embodiments of the invention. See Ward et al. (1993) Plant Mol. Biol. 22:361-66. With an inducible promoter, the rate of transcription increases in response to an inducing agent. Exemplary inducible promoters include, but are not limited to: Promoters from the ACEI system that responds to copper; In2 gene from maize that responds to benzenesulfonamide herbicide safeners; Tet repressor from Tn10; and the inducible promoter from a steroid hormone gene, the transcriptional activity of which may be induced by a glucocorticosteroid hormone (Schena et al. (1991) Proc. Natl. Acad. Sci. USA 88:10421-5).

Exemplary constitutive promoters include, but are not limited to: promoters from plant viruses, such as the 35S promoter from CaMV; promoters from rice actin genes; ubiquitin promoters; pEMU; MAS; maize H3 histone promoter; and the ALS promoter, XbaI/NcoI fragment 5' to the *Brassica napus* ALS3 structural gene (or a nucleotide sequence similarity to said XbaI/NcoI fragment) (PCT International Patent Publication No. WO 96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: a root-preferred promoter, such as that from the phaseolin gene; a leaf-specific and light-induced promoter such as that from cab or rubisco; an anther-specific promoter such as that from LAT52; a pollen-specific promoter such as that from Zm13; a microspore-preferred promoter such as that from apg, and a seed specific promoter (e.g., a promoter from PvDlec2, LfKCS3, FAE1, BoACP, or BnNapinC).

Heterologous: The term "heterologous," as applied to nucleic acids (e.g., polynucleotides, DNA, RNA, and genes) herein, means of different origin. For example, if a host cell is transformed with a nucleic acid that does not occur in the untransformed host cell in nature, then that nucleic acid is heterologous (and exogenous) to the host cell. Furthermore, different elements (e.g., promoter, enhancer, coding sequence, terminator, etc.) of a transforming nucleic acid may be heterologous to one another and/or to the transformed host.

Native: As used herein, the term "native" refers to the form of a polynucleotide or gene in its natural location in the organism or in the genome of an organism as found in nature, with its own regulatory sequences, if present.

Endogenous: As used herein, the term "endogenous" refers to a polynucleotide, gene, or polypeptide that is located in the organism or genome that normally comprises the molecule in nature.

Transformation: As used herein, the term "transformation" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) Nature 319:791-3); lipofection (Feigner et al. (1987) Proc. Natl. Acad. Sci. USA 84:7413-7); microinjection (Mueller et al. (1978) Cell 15:579-85); *Agrobacterium*-mediated transfer (Fraley et al. (1983) Proc. Natl. Acad. Sci. USA 80:4803-7); direct DNA uptake; and microprojectile bombardment (Klein et al. (1987) Nature 327:70).

Transgene: An exogenous polynucleotide encoding a product that is integrated into the genome of the host. In some examples, a transgene may contain regulatory sequences operably linked to a coding sequence of the transgene (e.g., a promoter).

Vector: A nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; or virus that carries exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, and protein coating).

Expression: As used herein, the term "expression" may refer to the transcription and stable accumulation of mRNA encoded by a polynucleotide, or to the translation of such an mRNA into a polypeptide. The term "over-expression," as used herein, refers to expression that is higher than endogenous expression of the same or a closely related gene. A heterologous gene is over-expressed if its expression is higher than that of a closely-related endogenous gene (e.g., a homolog).

Exogenous: The term "exogenous," as applied to nucleic acids (e.g., polynucleotides, DNA, RNA, and genes) herein, refers to one or more nucleic acid(s) that are not normally present within their specific environment or context. For example, if a host cell is transformed with a nucleic acid that does not occur in the untransformed host cell in nature, then that nucleic acid is exogenous to the host cell. The term exogenous, as used herein, also refers to one or more nucleic acid(s) that are identical in sequence to a nucleic acid already present in a host cell, but that are located in a different cellular or genomic context than the nucleic acid with the same sequence already present in the host cell. For example, a nucleic acid that is integrated in the genome of the host cell in a different location than a nucleic acid with the same sequence is normally integrated in the genome of the host cell is exogenous to the host cell. Furthermore, a nucleic acid (e.g., a DNA molecule) that is present in a plasmid or vector in the host cell is exogenous to the host cell when a nucleic acid with the same sequence is only normally present in the genome of the host cell.

Sequence identity: The term "sequence identity" or "identity," as used herein in the context of two polynucleotides or polypeptides, may refer to the residues (nucleotides or amino acids, respectively) in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein, the term "substantially identical" may refer to nucleotide sequences that are more than 85% identical. For example, a substantially identical nucleotide sequence may be at least 85.5%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

In some embodiments, the presence of a heterologous nucleic acid in a plant may be detected through the use of a nucleic acid probe. A probe may be a DNA molecule or an RNA molecule. RNA probes can be synthesized by means known in the art, for example, using a DNA molecule template. A probe may contain all or a portion of the nucleotide sequence of the heterologous nucleic acid and additional, contiguous nucleotide sequence from the plant genome. This is referred to herein as a "contiguous probe." The additional, contiguous nucleotide sequence is referred to as "upstream" or "downstream" of the heterologous nucleic acid, depending on whether the contiguous nucleotide sequence from the plant chromosome is on the 5' or the 3' side of the heterologous nucleic acid, as conventionally understood. As is recognized by those of ordinary skill in the art, the process of obtaining additional, contiguous nucleotide sequence for inclusion in a probe may be repeated nearly indefinitely (limited only by the length of the chromosome), thereby identifying additional nucleic acid along the chromosome. Any and all of the above-described varieties of probes may be used in some embodiments of the present invention.

A probe may contain a nucleotide sequence that is not contiguous to that of the heterologous nucleic acid; this probe is referred to herein as a "noncontiguous probe." The sequence of the noncontiguous probe is located sufficiently close to the sequence of the heterologous nucleic acid on the chromosome so that the noncontiguous probe is genetically linked to the heterologous nucleic acid. A probe may also be an exact copy of a heterologous nucleic acid to be detected. A probe may also be a nucleic acid molecule comprising, or consisting of, a nucleotide sequence that is substantially identical to a cloned segment of chromosomal DNA comprising a heterologous nucleic acid to be detected.

An oligonucleotide probe sequence may be prepared synthetically or by cloning. Suitable cloning vectors are well-known to those of skill in the art. An oligonucleotide probe may be labeled or unlabeled. A wide variety of techniques exist for labeling nucleic acid molecules, including, for example and without limitation: Radiolabeling by nick translation; random priming; tailing with terminal deoxytransferase; etc., where the nucleotides employed are labeled, for example, with radioactive $^{32}$P. Other labels which may be used include, for example and without limitation: Fluorophores; enzymes; enzyme substrates; enzyme cofactors; enzyme inhibitors; etc. Alternatively, the use of a label that provides a detectable signal, by itself or in conjunction with other reactive agents, may be replaced by ligands to which receptors bind, where the receptors are labeled (for example, by the above-indicated labels) to provide detectable signals, either by themselves, or in conjunction with other reagents. See, e.g., Leary et al. (1983) Proc. Natl. Acad. Sci. USA 80:4045-9.

A probe may also be a nucleic acid molecule that is "specifically hybridizable" or "specifically complementary" to an exact copy of the marker to be detected ("DNA target"). "Specifically hybridizable" and "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the Na$^+$ and/or Mg$^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2$^{nd}$ ed., vol. 1-3, Cold Spring Harbor Laboratory Press, Cold Spring Harbor, N.Y., 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 25% mismatch between the hybridization molecule and the DNA target. "Stringent conditions" include further particular levels of stringency. Thus, as used herein, "moderate stringency" conditions are those under which molecules with more than 25% sequence mismatch will not hybridize; conditions of "medium stringency" are those under which molecules with more than 15% mismatch will not hybridize; and conditions of "high stringency" are those under which sequences with more than 10% mismatch will not hybridize. Conditions of "very high stringency" are those under which sequences with more than 6% mismatch will not hybridize.

In particular embodiments, stringent conditions are hybridization at 65° C. in 6× saline-sodium citrate (SSC) buffer, 5×Denhardt's solution, 0.5% SDS, and 100 μg sheared salmon testes DNA, followed by 15-30 minute sequential washes at 65° C. in 2×SSC buffer and 0.5% SDS, followed by 1×SSC buffer and 0.5% SDS, and finally 0.2×SSC buffer and 0.5% SDS.

With respect to all probes discussed, supra, the probe may comprise additional nucleic acid sequences, for example, promoters; transcription signals; and/or vector sequences.

Protein/polypeptide: The terms "protein" and "polypeptide" are used interchangeably herein. The terms refer to a contiguous molecular chain of amino acids linked through peptide bonds. The terms do not refer to a specific length of the product. Thus, "peptides," "oligopeptides," and "proteins" are included within the definition of polypeptide. The terms include polypeptides containing co- and/or post-translational modifications of the polypeptide made in vivo or in vitro; for example and without limitation: glycosylations, acetylations, phosphorylations, PEGylations, and sulphations. In addition, protein fragments, analogs (including amino acids not encoded by the genetic code; e.g., homocysteine, ornithine, p-acetylphenylalanine, D-amino acids, and creatine), natural or artificial mutants, variants, fusion proteins, derivatized residues (e.g., alkylation of amine groups, acetylations or esterifications of carboxyl groups), and combinations of any of the foregoing are included within the meaning of polypeptide.

Typically, proteins have a function. However, proteins also encompass oligopeptides and smaller contiguous amino acid sequences that do not have a functional activity. Non-limiting examples of functional proteins include: receptors, receptor ligands, cytokines, antibodies, immunomodulatory molecules, signalling molecules, fluorescent proteins, proteins with insecticidal or biocidal activities, and enzymes. Useful general classes of enzymes include, but are not limited to: proteases, cellulases, oxidoreductases, lipases, lyases, ligases, hemicellulases, laccases, amylases, glucoamylases, esterases, dehydrogenases, lactases, polygalacturonases, galactosidases, ligninases, oxidases, peroxidases, transferases, glucose isomerases, nitrilases, hydroxylases, hydrolases, polymerases and depolymerases. In addition to enzymes, proteins that can be encoded by synthetic nucleic acid molecules disclosed herein include without limitation: transcription factors, antibodies, receptors, growth factors (any of the PDGFs, EGFs, FGFs, SCF, HGF, TGFs, TNFs, insulin, IGFs, LIFs, oncostatins, CSFs, etc.), immunomodulators, peptide hormones, cytokines, integrins, interleukins, adhesion molecules, thrombomodulatory molecules, protease inhibitors, angiostatins, defensins, cluster of differentiation antigens, interferons, chemokines, antigens including those from infectious viruses and organisms, oncogene products, thrombopoietin, erythropoietin, tissue plasminogen activator, and any other biologically active protein which is desired for use in a clinical, diagnostic, or veterinary setting. All of these proteins are well-defined in the literature (for example, by exemplary amino acid sequences), and are so defined herein. Also included are deletion mutants of such proteins, individual domains of such proteins, fusion proteins made from such proteins, and mixtures of such proteins.

Conservative substitution: As used herein with regard to a polypeptide, the term "conservative substitution" refers to a substitution where an amino acid residue is substituted for another amino acid in the same class. A non-conservative amino acid substitution is one where the residues do not fall into the same class, for example, substitution of a basic amino acid for a neutral or non-polar amino acid. Classes of amino acids that may be defined for the purpose of performing a conservative substitution are known in the art.

In some embodiments, a conservative substitution includes the substitution of a first aliphatic amino acid for a second, different aliphatic amino acid. For example, if a first amino acid is one of Gly; Ala; Pro; Ile; Leu; Val; and Met, the first amino acid may be replaced by a second, different amino acid selected from Gly; Ala; Pro; Ile; Leu; Val; and Met. In particular examples, if a first amino acid is one of Gly; Ala; Pro; Ile; Leu; and Val, the first amino acid may be replaced by a second, different amino acid selected from Gly; Ala; Pro; Ile; Leu; and Val. In particular examples involving the substitution of hydrophobic aliphatic amino acids, if a first amino acid is one of Ala; Pro; Ile; Leu; and Val, the first amino acid may be replaced by a second, different amino acid selected from Ala; Pro; Ile; Leu; and Val.

In some embodiments, a conservative substitution includes the substitution of a first aromatic amino acid for a second, different aromatic amino acid. For example, if a first amino acid is one of His; Phe; Trp; and Tyr, the first amino acid may be replaced by a second, different amino acid selected from His; Phe; Trp; and Tyr. In particular examples involving the substitution of uncharged aromatic amino acids, if a first amino acid is one of Phe; Trp; and Tyr, the first amino acid may be replaced by a second, different amino acid selected from Phe; Trp; and Tyr.

In some embodiments, a conservative substitution includes the substitution of a first hydrophobic amino acid for a second, different hydrophobic amino acid. For example, if a first amino acid is one of Ala; Val; Ile; Leu; Met; Phe; Tyr; and Trp, the first amino acid may be replaced by a second, different amino acid selected from Ala; Val; Ile; Leu; Met; Phe; Tyr; and Trp. In particular examples involving the substitution of non-aromatic, hydrophobic amino acids, if a first amino acid is one of Ala; Val; Ile; Leu; and Met, the first amino acid may be replaced by a second, different amino acid selected from Ala; Val; Ile; Leu; and Met.

In other embodiments, a conservative substitution includes the substitution of a first polar amino acid for a second, different polar amino acid. For example, if a first amino acid is one of Ser; Thr; Asn; Gln; Cys; Gly; Pro; Arg; His; Lys; Asp; and Glu, the first amino acid may be replaced by a second, different amino acid selected from Ser; Thr; Asn; Gln; Cys; Gly; Pro; Arg; His; Lys; Asp; and Glu. In particular examples involving the substitution of uncharged, polar amino acids, if a first amino acid is one of Ser; Thr; Asn; Gln; Cys; Gly; and Pro, the first amino acid may be replaced by a second, different amino acid selected from Ser; Thr; Asn; Gln; Cys; Gly; and Pro. In particular examples involving the substitution of charged, polar amino acids, if a first amino acid is one of His; Arg; Lys; Asp; and Glu, the first amino acid may be replaced by a second, different amino acid selected from His; Arg; Lys; Asp; and Glu. In further examples involving the substitution of charged, polar amino acids, if a first amino acid is one of Arg; Lys; Asp; and Glu, the first amino acid may be replaced by a second, different amino acid selected from Arg; Lys; Asp; and Glu. In particular examples involving the substitution of positively charged (basic), polar amino acids, if a first amino acid is one of His; Arg; and Lys, the first amino acid may be replaced by a second, different amino acid selected from His; Arg; and Lys. In further examples involving the substitution of positively charged, polar amino acids, if a first amino acid is Arg or Lys, the first amino acid may be replaced by the other amino acid of Arg and Lys. In particular examples involving the substitution of negatively charged (acidic), polar amino acids, if a first amino acid is Asp or Glu, the first amino acid may be replaced by the other amino acid of Asp and Glu.

In alternative embodiments, a conservative substitution includes the substitution of a first electrically neutral amino acid for a second, different electrically neutral amino acid. For example, if a first amino acid is one of Gly; Ser; Thr; Cys; Asn; Gln; and Tyr, the first amino acid may be replaced by a second, different amino acid selected from Gly; Ser; Thr; Cys; Asn; Gln; and Tyr.

In yet other embodiments, a conservative substitution includes the substitution of a first non-polar amino acid for a second, different non-polar amino acid. For example, if a first amino acid is one of Ala; Val; Leu; Ile; Phe; Trp; Pro; and Met, the first amino acid may be replaced by a second, different amino acid selected from Ala; Val; Leu; Ile; Phe; Trp; Pro; and Met.

In many examples, the selection of a particular second amino acid to be used in a conservative substitution to replace a first amino acid may be made in order to maximize the number of the foregoing classes to which the first and second amino acids both belong. Thus, if the first amino acid is Ser (a polar, non-aromatic, and electrically neutral amino acid), the second amino acid may be another polar amino acid (i.e., Thr; Asn; Gln; Cys; Gly; Pro; Arg; His; Lys; Asp; or Glu); another non-aromatic amino acid (i.e., Thr; Asn; Gln; Cys; Gly; Pro; Arg; His; Lys; Asp; Glu; Ala; Ile; Leu; Val; or Met); or another electrically-neutral amino acid (i.e., Gly; Thr; Cys; Asn; Gln; or Tyr). However, it may be preferred that the second amino acid in this case be one of Thr; Asn; Gln; Cys; and Gly, because these amino acids share all the classifications according to polarity, non-aromaticity, and electrical neutrality. Additional criteria that may optionally be used to select a particular second amino acid to be used in a conservative substitution are known in the art. For example, when Thr; Asn; Gln; Cys; and Gly are available to be used in a conservative substitution for Ser, Cys may be eliminated from selection in order to avoid the formation of undesirable cross-linkages and/or disulfide bonds. Likewise, Gly may be eliminated from selection, because it lacks an alkyl side chain. In this case, Thr may be selected, e.g., in order to retain the functionality of a side chain hydroxyl group. The selection of the particular second amino acid to be used in a conservative substitution is ultimately, however, within the discretion of the skilled practitioner.

Plant: The term "plant," as used herein includes any descendant, cell, tissue, seed, seed oil, or part thereof.

Trait or phenotype: The terms "trait" and "phenotype" are used interchangeably herein. For the purposes of the present disclosure, traits of particular interest include agronomically important traits, as may be expressed, for example, in a crop plant (e.g., expression of an insecticidal protein).

IV. Synthetic Polynucleotide Encoding a Polypeptide of Interest

This disclosure provides methods for designing a synthetic polynucleotide encoding a polypeptide of interest, for example, to increase expression the polypeptide of interest in a heterologous host cell or organism. In some embodiments herein, a synthetic polynucleotide encoding a polypeptide of interest is engineered, wherein the synthetic polynucleotide is derived from a reference gene containing at least one polyadenylation sequence (e.g., at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA). For example, the synthetic polynucleotide may comprise the at least one polyadenylation sequence from the reference gene in the same amount and in the same location of the coding sequence.

Embodiments herein provide synthetic polynucleotides encoding a polypeptide of interest that have been engineered according to the foregoing. Such synthetic polynucleotides may be particularly well-suited for use in expressing the polypeptide of interest in a transgenic plant cell, or transgenic plant tissue or plant comprising such a plant cell.

Methods of particular embodiments herein may be used to engineer a synthetic nucleic acid sequence for a variety of reasons known to those of skill in the art; e.g., to increase expression, to adapt the nucleic acid sequence to be expressed in a new host cell or organism, and to introduce functional and/or non-functional mutations into an encoded polypeptide. Typically in embodiments where a polypeptide of interest is a naturally-occurring gene product, or portion of a naturally-occurring gene product (e.g., an isolated protein domain), a naturally-occurring reference polynucleotide encoding the polypeptide may be obtained, for example, by searching genome databases or cloning from a source genome. In many cases, homologues or orthologs of such naturally-occurring reference polynucleotides may also be found in the genomes of other organisms. In embodiments, synthetic polynucleotides encoding all or part of a polypeptide of interest may be designed or derived from a reference polynucleotide that encodes any polypeptide of interest. In particular embodiments, the reference polynucleotide comprises at least one polyadenylation sequence.

In embodiments herein, a polypeptide of interest may be any protein or polypeptide that occurs in nature, or any naturally-occurring variant including, for example and without limitation, processed forms of such proteins. The polypeptide of interest may be a protein formed by combining portions or fragments of more than one naturally occurring protein, such as by mixing and matching functional protein domains. Synthetic nucleic acids of certain embodiments encode polypeptide(s) of interest that are, for example and without limitation, insecticidal proteins (e.g., from *Bacillus thuringiensis*); expression products of herbicide, water, and/or heat stress tolerance genes; proteins involved in plant oil production, storage, and/or metabolism; and/or expression products of marker genes. In some embodiments, a polypeptide of interest is one for which its expression in a plant results in a phenotype that is an agronomic trait, or is a reporter protein useful for introgressing or introducing agronomic traits.

Insecticidal proteins, for example, those with activity against Lepidoptera driver pests, are an extremely important tool in crop improvement. The Cry1Ab protein from *Bacillus thuringiensis* has demonstrated activity against *Ostrinia nubilalis* (European corn borer (ECB)) and *Helicoverpa zea* (corn earworm (CEW)) using in vitro diet based assays. Cry1Ab is an established active, and a form of the protein is currently utilized in the insect-resistant SMART STAX™ product. HERCULEX® has is also a successful agricultural tool. The active ingredient of HERCULEX®, Cry1Fa protein in the truncated form, has been demonstrated to be efficacious against many key maize pests, including *Spodoptera frugiperda* (fall armyworm (FAW)), *Ostrinia nubilalis* (European corn borer (ECB)), and *Helicoverpa zea* (corn earworm (CEW)).

Insects can develop resistance to the activity of Cry toxins through changes in the receptors located in the midgut that bind the truncated Cry toxin. Van Rie et al. (1990) Science 247(4938):72-4; Heckel et al. (2007) J. Invert. Pathol. 95(3):192-7. One method to prevent or delay the development of resistance to Cry toxins in insects is to express multiple toxins in the plant having different modes of action. Roush (1998) Philos. Trans. B 353:1777-86; Ives et al. (2011) Ecol. Appl. 21(2):503-15. Embodiments herein utilize Cry1Ab and/or Cry1Fa as insect resistance polypeptides as part of an insect management strategy to prolong the activity of an insect resistance trait in a plant. Such a method may provide a particular advantage in delaying the development of toxin resistance in pest insects.

In some embodiments herein, a native/wild-type gene sequence encoding a polypeptide of interest is identified and/or provided, and subsequently analyzed to determine whether polyadenylation signal sequences are present. In particular embodiments herein, a step in the engineering of a synthetic polynucleotide expressing the polypeptide of interest includes reducing in the polynucleotide (with respect to the reference gene) the number of undesirable polyadenylation signal sequences selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, TGTTTG, TTATAT, TGTAAT, AAATAA, ATTTTT, TATTTT, TTATTT, TTTATT, TTTTTT, TTTTAT, AATTTT, TTTTTA, TAATTT, TTAATT, AAATTT, AAATAA, ATATTT, TTTGTT, TTGTTT, ATATAT, ATTATT, ATTTTA, TTTAAT, and TTTTAA. In particular embodiments, occurrences of the Shaw-Kamen sequence, ATTTA, are also removed.

Known techniques in recombinant DNA technology may be used in certain embodiments to improve control of expression of heterologous polynucleotides, for example and without limitation, by manipulating the number of copies of the polynucleotides within the host cell; by manipulating the efficiency with which those polynucleotides are transcribed; by manipulating the efficiency with which the resultant transcripts are translated; and by manipulating the efficiency of post-translational modifications. By way of further example, promoter sequences may be genetically engineered to improve the level of expression in the host, as compared to the reference promoter. Thus, techniques useful for controlling the expression of polynucleotides include, for example and without limitation, integration of the polynucleotides into one or more host cell chromosomes; addition of vector stability sequences to plasmids; substitutions or modifications of transcription control signals (e.g., promoters, operators, and enhancers); substitutions or modifications of translational control signals (e.g., ribosome binding sites and Shine-Dalgarno sequences); modification of polynucleotides to correspond to the codon usage of the host cell; and deletion of sequences that destabilize transcripts.

Factors that may affect the rate of translational elongation of an encoded polypeptide of interest during synthesis include, for example, the level of charged tRNAs (Elf et al. (2003) Science 300:1718-22), which depends upon tRNA concentrations, tRNA charging rates, and amino acid availability. For example, a translational pause induced by a rare (or non-preferred) codon according to the host organism's codon usage bias may reduce the rate of heterologous protein expression. A rare codon-induced translational pause includes the presence of codons in the polynucleotide of interest that are rarely used in the host organism, and may have a negative effect on protein translation due to their scarcity in the available tRNA pool. These factors also include the rate of ribosomal tRNA selection (decoding rate), which depends upon: the strength of the codon-anticodon interaction; the preceding codon (P-site codon); the wobble base of the preceding codon; and the wobble base of the codon being read. Factors that may affect ribosomal fidelity include those that influence ribosomal frame-shifts, such as homopolymer stretches, G/C islands, A/T islands, and homopolymer stretches near pause sites. Furthermore, some polypeptides may be hindered in the ribosomal exit channel, which depends in part upon the sequence of the initial 10-20 amino acids of the polypeptide. In view of the foregoing, one method of improving optimal translation in a host organism includes performing codon optimization, which can result in rare host codons being modified in a synthetic polynucleotide.

Thus, in addition to removing undesirable polyadenylation signal sequences and Shaw-Kamen sequences, synthetic polynucleotides herein may be engineered that utilize codons roughly in the same frequency at which they are utilized, on average, in genes naturally occurring in the plant species in which the synthetic polynucleotide will be expressed. In some embodiments, the synthetic polynucleotide engineering process comprises optimizing the codon sequence by replacing rare codons in the sequence with preferred codons, and by preserving certain polyadenylation sequences in the coding sequence.

Table 1 provides exemplary target percentages for codon usage in synthetic genes intended for use in maize and soybean. These percentages may be used, for example, in the absence of more specific codon usage data, as well in dicots generally, or in plants generally.

TABLE 1

Exemplary target rescaled codon compositions of synthetic plant genes.

| Amino acid | Codon | Target usage % (maize) | Target usage % (soya) |
|---|---|---|---|
| ALA (A) | GCA | 18.0 | 33.1 |
|  | GCC | 34.0 | 24.5 |
|  | GCG | 24.0 | 0 |
|  | GCT | 24.0 | 42.3 |
| ARG (R) | AGA | 18.8 | 36.0 |
|  | AGG | 32.5 | 32.2 |
|  | CGA | 0 | 0 |
|  | CGC | 30.0 | 15.0 |
|  | CGG | 18.8 | 0 |
|  | CGT | 0 | 16.9 |
| ASN (N) | AAC | 68.0 | 50.0 |
|  | AAT | 32.0 | 50.0 |
| ASP (D) | GAC | 63.0 | 38.1 |
|  | GAT | 37.0 | 61.9 |
| CYS (C) | TGC | 68.0 | 50.0 |
|  | TGT | 32.0 | 50.0 |
| END | TAA | 0 | 0 |
|  | TAG | 0 | 0 |
|  | TGA | 100 | 100 |
| GLN (Q) | CAA | 38.0 | 55.5 |
|  | CAG | 62.0 | 44.5 |
| GLU (E) | GAA | 29.0 | 50.5 |
|  | GAG | 71.0 | 49.5 |
| GLY (G) | GGA | 19.0 | 31.9 |
|  | GGC | 42.0 | 19.3 |
|  | GGG | 19.0 | 18.4 |
|  | GGT | 20.0 | 30.4 |
| HIS (H) | CAC | 62.0 | 44.8 |
|  | CAT | 38.0 | 55.2 |
| ILE (I) | ATA | 14.0 | 23.4 |
|  | ATC | 58.0 | 29.9 |
|  | ATT | 28.0 | 46.7 |
| LEU (L) | CTA | 0 | 0 |
|  | CTC | 29.9 | 22.4 |
|  | CTG | 33.3 | 16.3 |
|  | CTT | 19.5 | 31.5 |
|  | TTA | 0 | 0 |
|  | TTG | 17.2 | 29.9 |

TABLE 1 -continued

Exemplary target rescaled codon compositions of synthetic plant genes.

| Amino acid | Codon | Target usage % (maize) | Target usage % (soya) |
|---|---|---|---|
| LYS (K) | AAA | 22.0 | 42.5 |
| | AAG | 78.0 | 57.5 |
| MET (M) | ATG | 100 | 100 |
| PHE (F) | TTC | 71.0 | 49.2 |
| | TTT | 29.0 | 50.8 |
| PRO (P) | CCA | 26.0 | 39.8 |
| | CCC | 24.0 | 20.9 |
| | CCG | 28.0 | 0 |
| | CCT | 22.0 | 39.3 |
| SER (S) | AGC | 25.3 | 16.0 |
| | AGT | 0 | 18.2 |
| | TCA | 17.6 | 21.9 |
| | TCC | 25.3 | 18.0 |
| | TCG | 15.4 | 0 |
| | TCT | 16.5 | 25.8 |
| THR (T) | ACA | 21.0 | 32.4 |
| | ACC | 37.0 | 30.2 |
| | ACG | 22.0 | 0 |
| | ACT | 20.0 | 37.4 |
| TRP (W) | TGG | 100 | 100 |
| TYR (Y) | TAC | 73.0 | 48.2 |
| | TAT | 27.0 | 51.8 |
| VAL (V) | GTA | 0 | 11.5 |
| | GTC | 34.8 | 17.8 |
| | GTG | 42.4 | 32.0 |
| | GTT | 22.8 | 38.7 |

In some embodiments, disclosed methods involve optimization of the nucleotide sequence of a polynucleotide, such that the primary structure of an encoded polypeptide is unchanged. The structure of an encoded polypeptide is determined, to the greatest extent, by the amino acid sequence of the polypeptide. Thus, a desired structure for an encoded polypeptide places limitations on its polynucleotide coding sequence that are determined by the degeneracy of the genetic code and standard codon usage. In certain embodiments of the invention, a synthetic polynucleotide is engineered in silico, such that the polynucleotide comprises a specific codon-optimized sequence selected from the codon space that encodes all or part of a polypeptide of interest, wherein the number and location of certain polyadenylation sequences are preserved from the native polynucleotide to the synthetic polynucleotide. Incorporation of the specific polynucleotide sequence that is selected may avoid certain problems associated with heterologous nucleotide sequences that encode polypeptides, and may achieve one or more desired properties (e.g., enhanced expression) when compared to polynucleotides that are merely codon-optimized, for example, by reference to the codon usage bias of an expression host organism.

A variety of methods are available to those skilled in the art for optimizing the coding sequence of a nucleic acid molecule (e.g., a polynucleotide encoding a polypeptide of interest) according to predetermined parameters. For example, the skilled artisan may optimize a coding sequence by inspection, e.g., to better conform to the codon usage bias of an expression host organism. More commonly, a computer-implemented software program may be used to optimize a coding sequence. Such software programs may comprise one or more algorithms that optimize factors selected from the group comprising: factors that may affect the expression of an encoded polypeptide of interest; factors that may affect the rate of translation initiation of a transcript; and factors that may affect the rate of translational elongation of the encoded polypeptide or its precursor. Accordingly, in some embodiments, a reference polynucleotide may be imported into a computer-implemented software program that is capable of optimizing a coding sequence according to predetermined parameters. Particular examples of such software programs include, without limitation, OPTGENE™ (Ocimum Biosolutions), Accelrys GCG™ (Accelrys Software, Inc.), OPTIMIZER™ (available for public use on the world-wide web at genomes.urv.es/OPTIMIZER), and OPTIMUMGENE™ (GenScript).

In some embodiments, the amino acid sequence of a polypeptide of interest may be used directly to obtain a codon-optimized polynucleotide sequence. In particular embodiments, the amino acid sequence of the polypeptide of interest (e.g., provided directly) may be used to deduce a codon-optimized polynucleotide encoding the amino acid sequence (e.g., in silico reverse-translation), for example, by using a computer-implemented software program that is capable of optimizing a coding sequence according to predetermined parameters. In specific examples, a codon-optimized polynucleotide may be deduced using the standard genetic code and an appropriate codon usage bias table for an expression host organism. It may desirable in some embodiments to deduce multiple codon-optimized polynucleotide encoding each polypeptide of interest. Thus, in particular examples, a polypeptide of interest may be used to deduce a set of 1, 2, 3, 4, 5, 6, 7, 8, 9, 10, 11, 12, 13, 14, 15, 16, 17, 18, 19, 20, or more codon-optimized nucleic acid sequences encoding the polypeptide of interest. In some embodiments, deduced codon-optimized polynucleotides encoding the polypeptide of interest may be exported into text files by a computer-implemented software program, or otherwise recorded for the practitioner. For example, a computer-implemented software program may export into a corresponding number of text files for an entire set of deduced codon-optimized polynucleotides encoding a single polypeptide of interest.

In other embodiments, codon-optimized polynucleotides encoding a polypeptide of interest may be aligned by sequence homology. In particular examples, one or more deduced codon-optimized polynucleotide(s) that correspond to all of the polyadenylation sequences of the polypeptide of interest are aligned with a native polynucleotide encoding the polypeptide of interest. In particular examples, the deduced codon-optimized nucleic acid sequences correspond to segments of protein coding regions, and the alignments may be performed with no "gaps" allowed.

According to the foregoing, methods herein may be used to provide a single codon-optimized polynucleotide encoding a polypeptide of interest. In particular examples, a method may be used to provide a set of single, codon-optimized polynucleotides, each of which the polypeptide of interest.

In some embodiments, a polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA may be incorporated into an optimized polynucleotide encoding an entire polypeptide of interest, such that the selected polyadenylation sequence is incorporated at the native position for the particular polyadenylation sequence in a native nucleic acid sequence encoding the polypeptide of interest, while the correct reading frame for the polypeptide of interest is maintained. For example, all members of the set of native polyadenylation sequences selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, each may be incorporated into an optimized polynucleotide encoding the entire polypeptide of interest, such that all members of the set are incorporated at their native positions for the particular polyadenylation sequence in the entire polynucleotide. Thus, some embodiments herein may be used to produce synthetic polynucleotides encoding a polypeptide of interest, wherein every polyadenylation sequence of the native polynucleotide is present in the same position of the aligned synthetic, optimized polynucleotide.

The optimization of a nucleic acid may include, for example, steps to improve the ability of the host to produce a heterologous protein, as well as steps to assist a researcher in efficiently designing an expression construct. Factors that may be considered during the optimization of a nucleic acid may include, without limitation: factors that may affect the expression of an encoded polypeptide of interest; factors that may affect the rate of translation initiation of a transcript; and factors that may affect the rate of translational elongation of the encoded polypeptide or its precursor. The selection of which of these factors to be considered during the design of a set of codon-optimized sequences is within the discretion of the skilled practitioner.

Factors that may affect the expression of a polypeptide of interest that is encoded by a polynucleotide may be influenced by the particular codons chosen to encode the amino acids of the polypeptide. Factors affecting the rate of production of mRNA from the template nucleic acid sequence may include: the RNA polymerase type used for transcription; the RNA polymerase level present in the expression system; and the transcription promoter sequence used. The mRNA levels may also be affected by the mRNA degradation rate, which in turn may be influenced by mRNA destabilizing motifs; RNAse recognition sequences; and polyA addition signals. The mRNA levels may also be affected by mRNA structures at the translational initiation site, at the ribosome binding site, at the start codon, and/or around the initial 10-50 codons of the coding sequence (or elsewhere within, or following, the open reading frame); transcriptional termination motifs present before or within the open reading frame; and signals within the transcribed sequence such as those that direct, alter, or modify mRNA splicing and/or nuclear export. A particular example of a factor affecting the rate of mRNA production from a template sequence is nucleotide repeat-induced polymerase slippage. Nucleotide repeat-induced polymerase slippage involves nucleotide sequence repeats that have been shown to cause slippage or stuttering of DNA polymerase which can result in frame-shift mutations. Such nucleotide repeats can also cause slippage of RNA polymerase. For example, in an organism with a high G+C content bias, there can be a higher degree of G or C nucleotide repeats. Therefore, one method of reducing the possibility of inducing RNA polymerase slippage includes altering extended repeats of G or C nucleotides.

Alternate translational initiation and interfering mRNA secondary structures may affect the rate of translational initiation for a particular transcript. Alternate translational initiation may occur in a synthetic polynucleotide sequence that inadvertently contains one or more motifs capable of functioning as a ribosome binding site (RBS). These sites can result in initiating translation of a truncated protein from a gene-internal site. One method of reducing the possibility of producing a truncated protein, which can be difficult to remove during purification, includes modifying putative internal RBS sequences from an optimized polynucleotide. Interfering secondary structures may sequester the RBS sequence or initiation codon, and have been correlated to a reduction in protein expression. Stem-loop structures can also be involved in transcriptional pausing and attenuation. An optimized polynucleotide may thus contain minimal secondary structures in the RBS and gene coding regions to allow for improved transcription and translation.

Another class of polynucleotide sequence elements that may affect heterologous protein expression includes restriction sites. Thus, optimization of a polynucleotide herein may include modification of restriction sites that could, for example, interfere with subsequent sub-cloning of transcription units into host expression vectors.

All or a portion of a polynucleotide sequence may be optimized. In some examples, a desired modulation of expression may be achieved by optimizing essentially an entire gene, while preserving certain polyadenylation sequences in the native gene. In other examples, a desired modulation may be achieved by optimizing part, but not all, of a gene. The starting point for such an optimization may be a coding sequence that consists only of commonly-used or preferred codons, according to the codon usage bias of the expression host, or a coding sequence which contains a mixture of common and non-common codons. Optimizing a polynucleotide can negatively or positively affect gene expression or protein production. For example, replacing a rare or non-preferred codon with a more common codon may affect the half-life of an mRNA molecule transcribed from the sequence comprising the replaced codon, or alter its structure by introducing a secondary structure that interferes with its translation. It may therefore be necessary, in certain instances, to further alter an optimized polynucleotide.

Within some embodiments, a synthetic polynucleotide comprising codon-optimized sequences encoding a polypeptide of interest while preserving certain polyadenylation sequences of the native gene may comprise more than one optimized sequence. For example, such a polynucleotide may encode a fusion polypeptide that comprises multiple polypeptides as described herein, or that comprises at least one polypeptide as described herein and an unrelated sequence. Fusion polypeptides may be prepared using standard techniques, including chemical conjugation, so as to permit translation into a single fusion polypeptide that retains at least one biological activity of both component polypeptides. A peptide linker sequence may be employed to separate polypeptide components of a fusion polypeptide by a distance sufficient to ensure that each polypeptide folds into appropriate secondary and tertiary structures. Such a peptide linker sequence may be incorporated into the fusion polypeptide using standard techniques well known in the art.

In many embodiments, non-coding regions of a nucleic acid molecule comprising a polynucleotide encoding a polypeptide of interest may also be optimized. For example, it may be desirable to include certain non-coding sequences either upstream, downstream, or within (e.g., introns) the synthetic polynucleotide. Therefore, in some embodiments, the sequence(s) of any non-coding sequences included in a nucleic acid molecule comprising a synthetic polynucleotide may be taken account in methods herein.

Nucleic acids comprising a synthetic polynucleotide encoding a polypeptide of interest may be expressed for use in a variety of applications, for example, to produce a recombinant polypeptide; to develop a new expression system; to compare expression properties to those of other nucleic acid sequences; and for diagnostic applications.

V. Expression of a Diverged, Codon-Optimized Nucleic Acid Sequence

Some embodiments herein provide methods for obtaining a desirable phenotype or trait in a plant cell, plant tissue, plant material, and/or whole plant, by a process comprising introducing a synthetic polynucleotide encoding a polypeptide of interest into a plant cell, so as to express the polypeptide of interest in the cell. In particular embodiments, the polypeptide of interest is a heterologous polypeptide not normally found in the cell.

Nucleic acid constructs (e.g., vectors) comprising a synthetic polynucleotide encoding a polypeptide of interest may be employed in particular embodiments for transformation of an expression host, wherein the construct may be integrated into the genome of the expression host. The construct may comprise at least transcriptional and translational initiation and termination regions, and the synthetic polynucleotide may be positioned between the initiation and termination regions and under their regulatory control. The construct may further comprise a selection marker and/or other functional sequences, for example and without limitation, homologous sequences for integration into the host genome; sequences that hybridize to PCR primers; and restriction sites.

In some embodiments, an expression host may be a plant cell, such as, for example, a plant cell in a plant tissue culture or whole plant. Embodiments of the invention may include plant cells from any tissue or wherever they are found, including but not limited to, in embryos, meristematic cells, callus, pollen, leaves, anthers, roots, root tips, flowers, seeds, pods, stems, and tissue culture. A synthetic polynucleotide may be incorporated into an appropriate vector, and introduced into a plant cell any method known to those of skill in the art. For example, a nucleic acid molecule may be introduced into a plant cell by methods including, without limitation, transfection with viral vectors, transformation with plasmid vectors, electroporation (Fromm et al. (1986) Nature 319:791-3), lipofection (Feigner et al. (1987) Proc. Natl. Acad. Sci. USA 84:7413-7), microinjection (Mueller et al. (1978) Cell 15:579-85), *Agrobacterium*-mediated transfer (Fraley et al. (1983) Proc. Natl. Acad. Sci. USA 80:4803-7), direct DNA uptake, and microprojectile bombardment (Klein et al. (1987) Nature 327:70).

In other embodiments, a vector comprising a synthetic polynucleotide may be introduced into a particular part of a plant cell (e.g., via nanoparticle bombardment). Examples of particular parts of plant cells into which a nucleic acid molecule may be introduced include, but are not limited to: cytosol, nucleus, tonoplasts, plastids, etioplasts, chromoplasts, leucoplasts, elaioplasts, proteinoplasts, amyloplasts, chloroplasts, and the lumen of a double membrane.

Cell transformation (including plant cell transformation) may involve the construction of an expression vector which will function in a particular cell. Such a vector may comprise DNA that includes a gene under control of, or operatively linked to, a regulatory element (for example, a promoter). The expression vector may contain one or more such operably-linked gene/regulatory element combinations. The vector(s) may be in the form of a plasmid and can be used alone or in combination with other plasmids to provide transformed cells using transformation methods as described herein to incorporate transgene(s) into the genetic material of a plant cell.

Plant cell expression vectors may include at least one genetic marker, operably linked to a regulatory element (a promoter, for example) that allows transformed cells containing the marker to be either recovered by negative selection (i.e., inhibiting growth of cells that do not contain the selectable marker gene) or by positive selection (i.e., screening for the product encoded by the genetic marker). Many selectable marker genes suitable for plant transformation are well known in the transformation arts and include, for example, genes that code for enzymes that metabolically detoxify a selective chemical agent which may be an antibiotic or an herbicide, or genes that encode an altered target which may be insensitive to the inhibitor. A few positive selection methods are also known in the art. In some embodiments, selectable marker genes suitable for plant transformation may include: the neomycin phosphotransferase II (nptII) gene under the control of plant regulatory signals, which confers resistance to kanamycin (See, e.g., Fraley et al. (1983) Proc. Natl. Acad. Sci. U.S.A. 80:4803); the hygromycin phosphotransferase gene, which confers resistance to the antibiotic, hygromycin (See, e.g., Vanden Elzen et al. (1985) Plant Mol. Biol., 5:299); marker genes of bacterial origin that confer resistance to antibiotics, including gentamycin acetyl transferase, streptomycin phosphotransferase, aminoglycoside-3'-adenyl transferase, and the bleomycin resistance determinant (See Hayford et al. (1988) Plant Physiol. 86:1216; Jones et al. (1987) Mol. Gen. Genet. 210:86; Svab et al. (1990) Plant Mol. Biol. 14:197; and Hille et al. (1986) Plant Mol. Biol. 7:171); marker genes that confer resistance to herbicides such as glyphosate, glufosinate or bromoxynil (See Comai et al. (1985) Nature 317: 741-744; Gordon-Kamm et al. (1990) Plant Cell 2:603-618; and Stalker et al. (1988) Science 242:419-423); and marker genes not of bacterial origin including, for example, mouse dihydrofolate reductase, plant 5-enolpyruvylshikimate-3-phosphate synthase, and plant acetolactate synthase (See Eichholtz et al. (1987) Somatic Cell Mol. Genet. 13:67; Shah et al. (1986) Science 233:478; and Charest et al. (1990) Plant Cell Rep. 8:643).

Another class of marker genes suitable for plant transformation requires screening of presumptively transformed plant cells rather than direct genetic selection of transformed cells for resistance to a toxic substance, such as an antibiotic. These genes may be particularly useful to quantify or visualize the spatial pattern of expression of a gene in specific tissues, and they are frequently referred to as reporter genes because they can be fused to a gene or gene regulatory sequence for the investigation of gene expression. Commonly used genes for screening transformed cells include β-glucuronidase (GUS), β-galactosidase, luciferase, and chloramphenicol acetyltransferase. See Jefferson (1987) Plant Mol. Biol. Rep. 5:387; Teeri et al. (1989) EMBO J. 8:343; Koncz et al. (1987) Proc. Natl. Acad. Sci. U.S.A. 84:131; and DeBlock et al. (1984) EMBO J. 3:1681. Methods are available for visualizing GUS activity in vivo that do not require destruction of plant tissue. Molecular Probes publication 2908 (1993) IMAGENE GREEN™, pp. 1-4; and Naleway et al. (1991) J. Cell Biol. 115:151. Genes encoding fluorescent proteins (e.g., GFP, EGFP, EBFP, ECFP, and YFP) have also been utilized as markers for gene expression in prokaryotic and eukaryotic cells. See Chalfie et al. (1994) Science 263:802. Thus, fluorescent proteins and mutations of fluorescent proteins may be used as screenable markers.

Expression of a synthetic polynucleotide included in a plant expression vector may be driven by a nucleotide sequence comprising a regulatory element, for example, a promoter. Several types of promoters useful in plant cells are now well known in the transformation arts, as are other regulatory elements that can be used alone or in combination with such promoters.

The term "promoter" refers to a region of DNA that may be upstream from the start of transcription and that may be involved in recognition and binding of RNA polymerase and other proteins to initiate transcription. A "plant promoter" may be a promoter capable of initiating transcription in plant cells. Examples of promoters under developmental control include promoters that preferentially initiate transcription in certain tissues, for example, in leaves, roots, seeds, fibers, xylem vessels, tracheids, or sclerenchyma. Such promoters are referred to as "tissue-preferred." Promoters which initiate transcription only in certain tissues are referred to as "tissue-specific." A "cell type-specific" promoter primarily drives expression in certain cell types in one or more organs, for example, vascular cells in roots or leaves. An "inducible" promoter can be a promoter which may be under environmental control. Examples of environmental conditions that may affect transcription by inducible promoters include, without limitation, anaerobic conditions or the presence of light. Tissue-specific, tissue-preferred, cell type-specific, and inducible promoters constitute the class of "non-constitutive" promoters. A "constitutive" promoter is a promoter which may be active under most environmental conditions.

An inducible promoter may be operably linked to an optimized nucleotide sequence of the invention for expression in a cell. Optionally, an inducible promoter may be operably linked to a nucleotide sequence encoding a signal sequence, which may be operably linked to a nucleotide sequence of the invention for expression in a cell. The rate of transcription of a nucleotide sequence operably linked to an inducible promoter may increase in response to an inducing agent. Any inducible promoter may be used in the instant invention. See Ward et al. (1993) Plant Mol. Biol. 22:361-366. Exemplary inducible promoters include, but are not limited to: those from the ACEI system that responds to copper (Mett et al. (1993) Proc. Natl. Acad. Sci. U.S.A. 90:4567-71); In2 gene from maize that responds to benzenesulfonamide herbicide safeners (Hershey et al. (1991) Mol. Gen Genetics 227:229-37; and Gatz et al. (1994) Mol. Gen. Genetics 243:32-8); and Tet repressor from Tn10 (Gatz et al. (1991) Mol. Gen. Genetics 227:229-37). A particularly useful inducible promoter may be a promoter that responds to an inducing agent to which plants do not normally respond. An exemplary inducible promoter may be the inducible promoter from a steroid hormone gene, the transcriptional activity of which may be induced by a glucocorticosteroid hormone. Schena et al. (1991) Proc. Natl. Acad. Sci. U.S.A. 88:10421-5.

Alternatively, a constitutive promoter may be operably linked to a synthetic polynucleotide for expression in a cell, or the constitutive promoter may be operably linked to a nucleotide sequence encoding a signal sequence which may be operably linked to a synthetic polynucleotide for expression in a cell. Different constitutive promoters may be utilized in the instant invention. Exemplary constitutive promoters include, but are not limited to: promoters from plant viruses, such as the 35S promoter from CaMV (Odell et al. (1985) Nature 313:810-2); promoters from rice actin genes (McElroy et al. (1990) Plant Cell 2:163-71); ubiquitin (Christensen et al. (1989) Plant Mol. Biol. 12:619-32; and Christensen et al. (1992) Plant Mol. Biol. 18:675-89); pEMU (Last et al. (1991) Theor. Appl. Genet. 81:581-8); MAS (Velten et al. (1984) EMBO J. 3:2723-30); and maize H3 histone (Lepetit et al. (1992) Mol. Gen. Genetics 231: 276-85; and Atanassova et al. (1992) Plant Journal 2(3):291-300). The ALS promoter, XbaI/NcoI fragment 5' to the *Brassica napus* ALS3 structural gene (or a nucleotide sequence similarity to said XbaI/NcoI fragment), represents a particularly useful constitutive promoter. See PCT International Patent Publication No. WO 96/30530.

A tissue-specific promoter may alternatively be operably linked to a synthetic polynucleotide for expression in a cell. Optionally, the tissue-specific promoter may be operably linked to a nucleotide sequence encoding a signal sequence which may be operably linked to a synthetic polynucleotide for expression in a cell. Plants transformed with a synthetic polynucleotide operably linked to a tissue-specific promoter may produce a protein product of the synthetic polynucleotide exclusively, or preferentially, in a specific tissue. Any tissue-specific or tissue-preferred promoter can be utilized in particular embodiments. Exemplary tissue-specific or tissue-preferred promoters include, but are not limited to: a root-preferred promoter, such as that from the phaseolin gene (Murai et al. (1983) Science 23:476-82; and Sengupta-Gopalan et al. (1985) Proc. Natl. Acad. Sci. U.S.A. 82:3320-4); a leaf-specific and light-induced promoter such as that from cab or rubisco (Simpson et al. (1985) EMBO J. 4(11):2723-9; and Timko et al. (1985) Nature 318:579-82); an anther-specific promoter such as that from LAT52 (Twell et al. (1989) Mol. Gen. Genetics 217:240-5); a pollen-specific promoter such as that from Zm13 (Guerrero et al. (1993) Mol. Gen. Genetics 244:161-168); and a microspore-preferred promoter such as that from apg (Twell et al. (1993) Sex. Plant Reprod. 6:217-224).

Transport of a polypeptide expressed from a synthetic polynucleotide to a subcellular compartment, such as the chloroplast, vacuole, peroxisome, glyoxysome, cell wall, or mitochondrion, or for secretion into the apoplast, can be accomplished by means of operably linking a nucleotide sequence encoding a signal sequence to the 5' and/or 3' region of the synthetic polynucleotide encoding the polypeptide. Targeting sequences at the 5' and/or 3' end of the structural gene may determine, during protein synthesis and processing, where the encoded protein may be ultimately compartmentalized. Alternatively, subcellular compartment targeting proteins may be directly linked to a nanoparticle to direct the nanoparticle coated with the molecule of interest to a desired subcellular compartment. Many signal sequences are known in the art. See, e.g., Becker et al. (1992) Plant Mol. Biol. 20:49; Close, P. S. (1993) Master's Thesis, Iowa State University; Knox et al. (1987) Plant Mol. Biol. 9:3-17; Lerner et al. (1989) Plant Physiol. 91:124-129; Fontes et al. (1991) Plant Cell 3:483-496; Matsuoka et al. (1991) Proc. Natl. Acad. Sci. U.S.A. 88:834; Gould et al. (1989) J. Cell. Biol. 108:1657; Creissen et al. (1991) Plant J. 2:129; Kalderon et al. (1984) Cell 39:499-509; and Steifel et al. (1990) Plant Cell 2:785-793.

In embodiments where the expression host is a multicellular organism (e.g., a plant), a vector or DNA construct may be introduced into one or more cells of the multicellular organism, and expressed therein. In some examples, a whole organism may be produced from one or more cells of the multicellular organism comprising an introduced vector or DNA construct. For example, methods of regenerating a whole plant from plant cells transformed with a nucleic acid molecule of interest, and subsequently selecting for a plant that has integrated the nucleic acid molecule into its genome, are known in the art.

In some embodiments, it will be understood that, in addition to be a multicellular organism, an expression host for use in embodiments herein may be a unicellular prokaryotic or eukaryotic organism. A variety of expression systems can be used for expression of a polypeptide from an optimized nucleic acid sequence of the invention. The expression host may, for example, be selected from a group comprising bacteria; algae; fungi (e.g., yeast); insect cells; animal cells; baculovirus; and mammalian tissue culture.

In particular embodiments, an expression system may be, for example and without limitation: a bacterial expression system, such as *Escherichia coli, Salmonella* spp., *Bacillus* spp., *Streptomyces* spp., *Pseudomonas* spp. (e.g., *P. fluorescens*), *Ralstonia eutropha, Chlamydomonas* spp.; yeast expression systems including *Saccharomyces, Pichia, Klebsiella*, and *Candida* species, *S. cerevisiae, P. pastoris, P. methanolica*, and *K. lactis*; fungal expression systems including *Cryptosporidium* and *Trichoderma* spp.; filamentous fungal protein production systems; protozoan expression systems including *Plasmodium falciparum* and *Leishmania*; model organisms including *Caenorhabditis elegans, Drosophila melanogaster*, and *Xenopus laevis*; plant cells (including, e.g., soybean, bushbean, maize, cotton, tobacco, and *Arabidopsis*); tissue culture expression systems including COS cells, Chinese Hamster Ovary cells, and fibroblasts such as 3T3 cells; cell lines infected with adenovirus; insect cell lines such as those derived from *Spodptera* spp. for growing baculovirus; model organisms for the study of disease and tests of the efficacies of DNA vaccines such as macaques, mice, rats, guinea pigs, sheep, goats and rabbits; in vitro expression systems prepared from extracts of living cells such as *E. coli* extracts, wheat germ extracts, rabbit reticulocyte lysates; and in vitro expression systems prepared by assembly of purified individual components.

Methods for gene expression in a genetically modified organism, including, for example and without limitation, a plant, are known in the art. Some embodiments include a recombinant vector (e.g., a plasmid) comprising one or more heterologous polynucleotides encoding a heterologous polypeptide of interest. A recombinant vector is an engineered (e.g., artificially produced) nucleic acid molecule that is used as a tool for manipulating a nucleic acid of choice, and/or for introducing such a nucleic acid into a host cell. The recombinant vector may therefore be suitable for use in cloning, sequencing, and/or otherwise manipulating a polynucleotide therein, such as by expressing and/or delivering the polynucleotide into a host cell to form a recombinant cell. A vector may contain nucleotide sequences that are not naturally found adjacent to the polynucleotide to be cloned or delivered. A vector may also contain regulatory nucleic acid sequences (e.g., promoters, untranslated regions) that are naturally found adjacent to the polynucleotide or that are useful for expression of the polynucleotide. An integrated polynucleotide may be under chromosomal promoter control, under native or plasmid promoter control, or under a combination of several promoter controls. A vector may be either RNA or DNA, and may be either prokaryotic or eukaryotic. A vector may be maintained as an extrachromosomal element (e.g., a plasmid) or it may be integrated into a chromosome of a recombinant organism (e.g., a microbe, yeast, and plant cell). The entire vector may remain in place within a host cell, or under certain conditions, extraneous DNA (e.g., unnecessary plasmid sequences) may be deleted, leaving behind one or more heterologous polynucleotides encoding a heterologous polypeptide of interest. Single or multiple copies of the heterologous polynucleotides may be integrated into the host genome. A recombinant vector of the present invention may contain at least one selectable marker.

In some embodiments, a recombinant vector comprising one or more heterologous polynucleotides encoding a heterologous polypeptide of interest is an expression vector, for example, a plant expression vector. In such embodiments, at least one polynucleotide encoding the product to be produced may be inserted into the recombinant vector in a manner that operably links the polynucleotide(s) to regulatory sequences in the vector that enable the transcription and translation of the nucleic acid sequence within the recombinant host cell. Vectors useful for the transformation of a variety of host organisms and cells are known in the art. Typically, a vector contains a selectable marker, and sequences allowing autonomous replication or chromosomal integration in the desired host.

Suitable methods for transformation of host cells include any method by which DNA can be introduced into a cell, such as by transformation of protoplasts (See, e.g., U.S. Pat. No. 5,508,184), by desiccation/inhibition-mediated DNA uptake (See, e.g., Potrykus et al. (1985) Mol. Gen. Genet. 199:183-8), by electroporation (See, e.g., U.S. Pat. No. 5,384,253), by agitation with silicon carbide fibers (See, e.g., U.S. Pat. Nos. 5,302,523 and 5,464,765), by *Agrobacterium*-mediated transformation (See, e.g., U.S. Pat. Nos. 5,563,055; 5,591,616; 5,693,512; 5,824,877; 5,981,840; and 6,384,301), and by acceleration of DNA-coated particles (See, e.g., U.S. Pat. Nos. 5,015,580; 5,550,318; 5,538,880; 6,160,208; 6,399,861; and 6,403,865). Through the application of techniques such as these, the cells of virtually any species may be stably transformed, including both monocotyledonous and dicotyledonous plants. In some embodiments, transforming DNA is integrated into the genome of the host cell. In the case of multicellular species, transgenic cells may be regenerated into a transgenic organism. Any of these techniques may be used to produce a transgenic monocotyledonous or dicotyledonous plant, for example, comprising one or more heterologous polynucleotides encoding a heterologous polypeptide of interest in the genome of the transgenic plant.

The most widely utilized method for introducing an expression vector into plants is based on the natural transformation system of *Agrobacterium. A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. The Ti (tumor-inducing)-plasmids contain a large segment, known as T-DNA, which is transferred to transformed plants. Another segment of the Ti plasmid, the vir region, is responsible for T-DNA transfer. The T-DNA region is bordered by terminal repeats. In modified binary vectors, the tumor-inducing genes have been deleted, and the functions of the vir region are utilized to transfer foreign DNA bordered by the T-DNA border sequences. The T-region may also contain a selectable marker for efficient recovery of transgenic plants and cells, and a multiple cloning site for inserting sequences for transfer such as a dsRNA encoding nucleic acid.

Thus, in particular embodiments, a plant transformation vector is derived from a Ti plasmid of *A. tumefaciens* (See, e.g., U.S. Pat. Nos. 4,536,475, 4,693,977, 4,886,937, and 5,501,967; and European Patent EP 0 122 791) or a Ri plasmid of *A. rhizogenes*. Additional plant transformation vectors include, for example and without limitation, those described by Herrera-Estrella et al. (1983) Nature 303:209-13; Bevan et al. (1983) Nature 304:184-7; Klee et al. (1985) Bio/Technol. 3:637-42; and in European Patent EP 0 120 516, and those derived from any of the foregoing. Other bacteria such as *Sinorhizobium, Rhizobium*, and *Mesorhizobium* that interact with plants naturally can be modified to mediate gene transfer to a number of diverse plants. These plant-associated symbiotic bacteria can be made competent for gene transfer by acquisition of both a disarmed Ti plasmid and a suitable binary vector.

After providing exogenous DNA to recipient cells, transformed cells are generally identified for further culturing and plant regeneration. In order to improve the ability to identify transformed cells, one may desire to employ a selectable or screenable marker gene, as previously set forth, with the transformation vector used to generate the transformant. In the case where a selectable marker is used, transformed cells are identified within the potentially transformed cell population by exposing the cells to a selective agent or agents. In the case where a screenable marker is used, cells may be screened for the desired marker gene trait.

Cells that survive the exposure to the selective agent, or cells that have been scored positive in a screening assay, may be cultured in media that supports regeneration of plants. In some embodiments, any suitable plant tissue culture media (e.g., MS and N6 media) may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

To confirm the presence of a nucleic acid molecule of interest (for example, a heterologous polynucleotide encoding a heterologous polypeptide of interest) in the regenerating plants, a variety of assays may be performed. Such assays include, for example: molecular biological assays, such as Southern and Northern blotting, PCR, and nucleic acid sequencing; biochemical assays, such as detecting the presence of a protein product, e.g., by immunological means (ELISA and/or Western blots) or by enzymatic function; plant part assays, such as leaf or root assays; and analysis of the phenotype of the whole regenerated plant.

Integration events may be analyzed, for example, by PCR amplification using, e.g., oligonucleotide primers specific for a nucleic acid molecule of interest. PCR genotyping is understood to include, but not be limited to, polymerase-chain reaction (PCR) amplification of genomic DNA derived from isolated host plant callus tissue predicted to contain a nucleic acid molecule of interest integrated into the genome, followed by standard cloning and sequence analysis of PCR amplification products. Methods of PCR genotyping have been well described (for example, Rios, G. et al. (2002) Plant J. 32:243-53) and may be applied to genomic DNA derived from any plant species (e.g., *Z. mays* or *G. max*) or tissue type, including cell cultures.

A transgenic plant formed using *Agrobacterium*-dependent transformation methods typically contains a single recombinant polynucleotide inserted into one chromosome. The single recombinant polynucleotide is referred to as a "transgenic event" or "integration event." Such transgenic plants are heterozygous for the inserted exogenous sequence. In some embodiments, a transgenic plant homozygous with respect to a transgene may be obtained by sexually mating (selfing) an independent segregant transgenic plant that contains a single exogenous gene sequence to itself, for example an $T_0$ plant, to produce $T_1$ seed. One fourth of the $T_1$ seed produced will be homozygous with respect to the transgene. Germinating $T_1$ seed results in plants that can be tested for heterozygosity, typically using a SNP assay or a thermal amplification assay that allows for the distinction between heterozygotes and homozygotes (i.e., a zygosity assay).

In addition to direct transformation of a plant with a recombinant nucleic acid molecule, transgenic plants can be prepared by crossing a first plant having at least one transgenic event with a second plant lacking such an event. For example, a recombinant nucleic acid molecule comprising one or more heterologous polynucleotide(s) encoding a heterologous polypeptide of interest may be introduced into a first plant line that is amenable to transformation to produce a transgenic plant, which transgenic plant may be crossed with a second plant line to introgress the polynucleotide(s) into the second plant line.

The foregoing genetic manipulations of a recombinant host can be performed using standard genetic techniques and screening, and can be made in any host cell that is suitable to genetic manipulation. In some embodiments, the recombinant host is a higher plant, including both dicotyledonous and monocotyledonous plants, and consumable plants, including crop plants and plants. Thus, any plant species or plant cell can be selected.

Particular embodiments herein provide methods of producing a heterologous polypeptide of interest in the cytoplasm and/or periplasm of a cell. Some embodiments utilize a synthetic polynucleotide optimized for heterologous expression in a host organism (e.g., a bacterial host organism). In particular embodiments, such an optimized synthetic polynucleotide may be ligated into an expression vector, and the expression vector comprising the optimized polynucleotide may be introduced into an expression host cell (e.g., by transformation), where a polypeptide is expressed from the optimized synthetic nucleic acid sequence.

Nucleic acid molecules comprising a synthetic polynucleotide encoding a polypeptide of interest may be produced by methods known to those of skill in the art. For example, in some embodiments, relatively short segments of a desired nucleic acid sequence may be reliably synthesized, followed by concatenation. Advances in the field of DNA synthesis have allowed the reliable synthesis of longer, as well as relatively shorter, polynucleotides. Synthetic techniques allow reasonably accurate oligonucleotide synthesis of 300 bases or more. Thus, in other embodiments, longer polynucleotides may be synthesized, such that concatenation may not be required. However, synthetic chemically-produced oligonucleotides are typically between 20 and 100 bp in length. In some embodiments, a synthetic gene or gene fragment may be prepared using PCR in a step-wise fashion by the annealing and extension of synthetic alternating and overlapping sense and antisense oligomers (for example, 90-110 bp in length) designed to encode the final desired sequence.

Oligonucleotide production may include oligo-synthesis carried out by the phosphoramidite protocol as a solid phase synthesis. Briefly, a first nucleotide with its 5'-OH functional group protected by a DMT-group may be coupled to polystyrene beads as a solid phase. Next, the DMT-group may be removed by acid treatment, generating a free 5'-OH group. Then, the phosphoramidite of choice may be added, converted to a reactive intermediate in weakly acidic conditions, and coupled to the free 5'-OH group to produce a novel phosphite linkage. These reactions may take place in THF or DMSO. As the 5'-OH of the added nucleotide remains protected, only one nucleotide is added to the growing chain. The 5'-OH groups that do not react may be capped so that they cannot continue to take part in the synthesis process and generate oligonucleotides with deletions. This may be achieved by acetylation after treatment with acetic acid and 1-methylimidazole. Finally, water and iodine may be added to oxidize the phosphite linkage to a phosphodiester linkage. In between steps, the production system may be conditioned by washing with a suitable solvent. After repeating this sequence of steps as required, the oligonucleotide may finally be cleaved from the column, and treated with ammonium hydroxide at high temperature to remove all remaining protecting groups. This process may be made more efficient by use of a photolithography approach, for example, as provided by NIMBLEGEN™ (Febit, Germany).

After short oligonucleotides have been produced by solid state synthesis, the oligonucleotides may be assembled into larger DNA fragments, for example, to a size of about 500 bp. This is typically achieved by one of a variety of enzyme-assisted methods. For example, short overlapping oligonucleotide pairs may be used to generate longer dsDNA molecules via a Klenow extension reaction. The corresponding oligonucleotides may be mixed, hybridized, and then converted to larger assemblies by PCA. In a PCA reaction, all oligonucleotides that together represent the targeted double-stranded DNA fragment are present. By repeated melting and re-hybridization, the oligonucleotides are step-by-step extended into longer sections until a certain population reaches the desired length. Note that this reaction is carried out without terminal oligonucleotide in excess, so it is not an amplification reaction. Rather, every full-length fragment consists of oligonucleotides and their extensions, thereby reducing the chance of introducing errors by polymerase action. An alternative methodology to PCA is polymerase assembly multiplexing (PAM), wherein terminal primers are added to a pool of oligonucleotides such that only a specific subset of the oligonucleotides is amplified. In a second round of PAM reactions, multiple oligonucleotides can be recombined into a single DNA molecule by using a novel set of primers.

Large oligonucleotides (for example, oligonucleotides produced by PCA, PMA, etc.) may be assembled into still larger DNA molecules, for example, by restriction digestion and ligation.

In embodiments wherein a polypeptide of interest comprising amino acid repeat regions is to be expressed in a prokaryotic cell or expression system, an optimized polynucleotide encoding the polypeptide of interest may first be cloned into a prokaryotic vector by linearizing a vector having an origin of replication and convenient restriction sites, which may involve a polylinker, for insertion of the nucleic acid sequence. The vector may also have a marker gene for selection, which may impart antibiotic resistance or afford another distinguishing characteristic (e.g., chromophore or fluorophore formation). There are a wide variety of antibiotic reagents (e.g., tetracycline, chloramphenicol, actinomycin, neomycin, ampicillin, hygromycin, heavy metals, etc.) that may be utilized for marker-assisted selection. Other markers include β-galactosidase, which, converts the substrate X-gal to provide a blue color when it is expressed. Numerous vectors are commercially available for cloning in bacteria, and these vectors are well-known to those of skill in the art. In some embodiments, a prokaryotic vector comprising one or more optimized synthetic polynucleotide(s) encoding a polypeptide of interest may then be introduced into an appropriate cloning host by any convenient means, including without limitation; calcium phosphate precipitated DNA, fusion, transfection, and conjugation. The cells may then be grown in an appropriate selective nutrient medium. Surviving cells may be harvested, lysed, and the plasmid isolated.

A prokaryotic expression vector may be characterized by having an origin of replication which is functional in an appropriate expression host, usually for episomal maintenance, and a marker for selection. For unintegrated vectors or constructs, the origin of replication will usually provide for multicopies, for example, at least about 5 copies on the average. The expression vector typically will also have a promoter which is functional in the expression host. A large number of promoters are available and particular promoters may, for example, provide for a high level of either inducible or constitutive transcription. Illustrative promoters that may be useful in some embodiments include, without limitation: β-lactamase; α-galactosidase; $\lambda P_L$ or $\lambda P_R$ promoters; trpE promoter; trp-lac promoter; T7 promoter (particularly genes 9 and 10); and cI$^{ts}$.

A nucleic acid molecule comprising an optimized polynucleotide may be combined with a linearized vector by hybridization, for example, ligation. Where the optimized polynucleotide does not have an initiation codon, such a codon can be added. In some embodiments, a polynucleotide may be inserted into a coding sequence present in the vector (in an appropriate reading frame), under the transcriptional control of a promoter. A signal sequence may be included at the 5' terminus of a coding sequence to allow for secretion of the polypeptide product into the periplasmic space. Generally, the product will be produced intracellularly.

The expression host cell comprising an introduced vector or DNA construct may be grown in an appropriate medium in culture (e.g., fermentation). After the cells have been grown to an appropriate density, the cells may be harvested, lysed, and the expression product may be isolated in accordance with its physical and chemical characteristics. In some embodiments, an expression product may be insoluble at moderate temperatures in an aqueous medium, and may be purified by detergent extraction at mildly elevated temperatures. See U.S. Pat. No. 5,235,041. As appropriate, the crude or purified expression product may then be used for its intended purpose.

Embodiments herein allow for the expression of any polypeptide of interest. In some examples, the polypeptide of interest may be itself desirable for an application (e.g., a polymer). In other examples, the polypeptide of interest may be expressed in the host to produce a further desirable polypeptide, small molecule, or other substance (e.g., an enzyme), or to introduce a desired phenotype in the host. In particular examples, a polypeptide of interest may be: a protein that is not normally found in cells of the expression host; an agronomic gene product; a polypeptide that confers resistance to pests or disease; A *Bacillus thuringiensis* protein; a lectin; a vitamin-binding protein (e.g., avidin); an enzyme inhibitor; an insect-specific hormone or pheromone; a peptide or neuropeptide that is specific to a particular organism; a venom; an enzyme responsible for a hyperaccumulation of a monoterpene, a sesquiterpene, a steroid, hydroxamic acid, a phenylpropanoid derivative or other non-protein molecule; an enzyme involved in the modification, including the post-translational modification, of a biologically active molecule (e.g., an enzyme involved in omega-3 fatty acid synthesis); a signal transduction molecule or molecule that stimulates signal transduction (e.g., calmodulin); a hydrophobic moment peptide; a membrane permease, transporter, or channel; a channel former or channel blocker; a viral-invasive protein or complex toxin derived therefrom; an antibody or immunotoxin (e.g., a virus-specific antibody); a developmental-arrestive protein; a polypeptide that confers resistance to an herbicide, fungicide, or other harmful small molecule; scaffolding proteins; and synthetic polypeptides that are designed to have a particular function (e.g., a function attributable to amino acid repeat regions, such as binding properties or physical characteristics). In some embodiments, a polypeptide of interest may be appropriated from nature. In other embodiments, a polypeptide of interest may be a polypeptide that is not normally found in nature; for example, a mutant polypeptide comprising a conservative mutation in the amino acid sequence of a native polypeptide of interest.

In particular embodiments, two or more different candidate sequences that were generated by sequence optimization using different parameters (e.g., sequences that differ in a their codon usage) may be generated and tested to determine if they possess the desired property. Candidate sequences may be evaluated, for example, to search for the presence of regulatory elements, such as silencers or enhancers, or to search for the presence of regions of coding sequence which could be converted into such regulatory elements by an alteration in codon usage. Additional criteria may include enrichment for particular nucleotides (e.g., A, C, G or U, codon bias for a particular amino acid), the presence or absence of particular mRNA secondary or tertiary structure, and/or the presence or absence of additional polyadenylation sequences. Adjustment to the candidate sequence for further expression may be made based on such criteria.

Promising candidate sequences may be constructed and evaluated experimentally. Multiple candidates may be evaluated independently of each other, or the process can be iterative, either by using the most promising candidate as a new starting point, or by combining regions of two or more candidates to produce a novel hybrid. Further rounds of modification and evaluation may be desirable.

Other embodiments herein provide methods for obtaining a desirable phenotype or trait in a plant cell, plant tissue, plant material, and/or whole plant, wherein the desirable phenotype is, for example, the expression of an insect toxin, and wherein the desirable trait may be pest tolerance and/or resistance. In some examples, a method for controlling pests in a plant comprises expressing a synthetic polynucleotide encoding a polypeptide of interest in a plant cell, where the synthetic polynucleotide encodes an insect toxin; for example and without limitation, a *Bacillus thuringiensis* Cry protein. Particular examples of a method for controlling pests in meal or flour comprise obtaining grain or seed from a plant containing a synthetic polynucleotide, wherein the plant expresses an insect toxin. Transgenic plants that express an insect toxin may be resistant to attack by an insect target pest by virtue of the presence of controlling amounts of the subject insecticidal protein (or variants thereof) in the cells of the plant. For example, by incorporating into the genome of a plant a polynucleotide that encodes a polypeptide having the insecticidal properties of the Bt insecticidal toxins, insect target pests (e.g., the adult or larvae) are made to die after consuming material of the plant.

Particular embodiments herein provide methods for obtaining a desirable phenotype or trait in a plant cell, plant tissue, plant material, and/or whole plant, wherein the desirable phenotype is, for example, the expression of an herbicide tolerance and/or resistance gene, and wherein the desirable trait may be herbicide tolerance and/or resistance. In some examples, a method for providing herbicide tolerance to a plant comprises expressing a synthetic polynucleotide encoding a polypeptide of interest in a plant cell, where the synthetic polynucleotide encodes an herbicide tolerance enzyme, for example and without limitation, the aryloxyalkanoate dioxygenase (AAD1) (See PCT International Patent Publication No. WO 2005/107437); phosphinothricin acetyltransferase (PAT), or 5-enolpyruvylshikimate-3-phosphate synthase (EPSP synthase) enzymes.

Particular embodiments herein provide methods for obtaining a desirable phenotype or trait in a plant cell, plant tissue, plant material, and/or whole plant, wherein the desirable phenotype is, for example, expression of a protein involved in a plant oil trait, and wherein the desirable trait may be a modified oil profile in the plant (e.g., in a seed of the plant). In some examples, a method for modifying the oil profile of a plant comprises expressing a synthetic polynucleotide encoding a polypeptide of interest in a plant cell, where the synthetic polynucleotide encodes one or more enzymes for modifying oil profiles in plants; for example and without limitation, a fatty acid desaturase (e.g., FAD2 and FAD3).

Particular embodiments herein provide methods for obtaining a desirable phenotype or trait in a plant cell, plant tissue, plant material, and/or whole plant, wherein the desirable phenotype is, for example, expression of a stress tolerance gene, and wherein the desirable trait may be increased stress tolerance to, for example, water and/or heat stress. In some examples, a method for providing stress tolerance to a plant comprises expressing a synthetic polynucleotide encoding a polypeptide of interest in a plant cell, where the synthetic polynucleotide encodes one or more stress tolerance proteins; for example and without limitation, the stress associated protein (SAP 1) (U.S. Patent Publication No. 2010/0275327); and 1-Cys peroxiredoxin (1-CysPrx) proteins (Mowla et al. (2002) Planta 215:716-26).

Particular embodiments herein provide methods for obtaining a desirable phenotype or trait in a plant cell, plant tissue, plant material, and/or whole plant, wherein the desirable phenotype is, for example, expression of a marker protein, and wherein the desirable trait may be marker selection. In some examples, a method for providing marker selection to a plant comprises expressing a synthetic polynucleotide encoding a polypeptide of interest in a plant cell, where the synthetic polynucleotide encodes one or more transformation marker proteins; for example and without limitation, green fluorescence protein (GFP) or beta-glucuronidase enzyme.

VI. Transgenic Plants Comprising the Polypeptide of Interest

This disclosure also provides genetically-modified organisms comprising a heterologous, synthetic polynucleotide encoding a polypeptide of interest. Some embodiments herein provide a transgenic plant comprising a heterologous, synthetic polynucleotide encoding a polypeptide of interest, for example, as may be produced by regeneration of a plant from a plant cell transformed with a nucleic acid comprising the synthetic polynucleotide. A synthetic polynucleotide encoding a polypeptide of interest may be operably linked to regulatory sequences (e.g., a promoter) appropriate to the organism, as previously set forth. In particular embodiments, the organism may express the polypeptide of interest. In certain embodiments herein, a polypeptide of interest may be expressed from an optimized polypeptide at a level which is at least 110%, 150%, 200%, 500%, 1,000%, 5,000% or even 10,000% of that expressed by a polynucleotide encoding the same polypeptide that has not been likewise optimized; for example, a polynucleotide that has been codon-optimized for expression in the same host, but wherein the polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA have not been preserved.

In some embodiments, a genetically-modified organism comprising a heterologous, synthetic polynucleotide encoding a polypeptide of interest is a genetically-modified plant, wherein at least some of the cells of the genetically-modified plant comprise one or more of the heterologous, synthetic polynucleotides. In one example of an embodiment, a plasmid comprising a heterologous, synthetic polynucleotide encoding a polypeptide of interest and a selectable marker are introduced into a plant cell, for example, by any of the methods previously enumerated herein. Stable transformants that have stably integrated the synthetic polynucleotide and/or the selectable marker may be selected from such plant cells. In other embodiments, a plant cell comprising the synthetic polynucleotide (for example, a stable transformant that has been selected) may be propagated to produce new plant cells comprising the synthetic polynucleotide. Plant cells comprising a synthetic polynucleotide may be a regenerable cell that may be used to regenerate a whole plant. Such plant cells and whole plants generated therefrom may express a polypeptide of interest that is encoded by the synthetic polynucleotide.

In these and further embodiments, methods of creating regenerable plant cells comprising a synthetic polynucleotide (e.g., for use in tissue culture) may be provided. A tissue culture may be capable of regenerating plants having substantially the same genotype as the regenerable cells. The regenerable cells in such tissue cultures may be embryos, protoplasts, meristematic cells, callus, pollen, leaves, anthers, roots, root tips, flowers, seeds, pods or stems. Some embodiments of the invention provides plants regenerated from the tissue cultures of the invention.

Also provided herein are methods for generating stabilized plant lines comprising a synthetic polynucleotide encoding a polypeptide of interest, wherein cells of the stabilized plant lines may express the polypeptide of interest that is encoded by the polynucleotide. Methods of generating stabilized plant lines are known to one of ordinary skill in the art, and may include techniques such as, but not limited to, selfing, backcrosses, hybrid production, and crosses to populations. All plants and plant cells comprising a synthetic polynucleotide encoding a polypeptide of interest as described herein do not exist in nature, and they may exhibit advantageous expression properties of the heterologous polypeptide of interest, for example, when compared to a plant or plant cell comprising a synthetic polynucleotide encoding the polypeptide of interest that has not been likewise optimized. Plant cells comprising a synthetic polynucleotide may be used in crosses with other, different, plant cells to produce first generation ($F_1$) hybrid cells, seeds, and/or plants with superior or desirable characteristics.

Any plant or plant cell expressing a polypeptide of interest from a synthetic polynucleotide optimized by the methods described herein, or plant material comprising such a polypeptide, is included in particular embodiments. In particular embodiments, a synthetic polynucleotide is utilized to produce genetically-modified *Brassica napus* plants. In further embodiments, genetically-modified plants produced using a synthetic polynucleotide may be, for example and without limitation: a higher plant; dicotyledonous plant; monocotyledonous plant; consumable plant (e.g., crop plants and plants used for their oils); soybean; rapeseed; linseed; corn; safflowers; sunflowers; tobacco; a plant of the family Fabaceae (Leguminosae, legume family, pea family, bean family, or pulse family); a plant of the genus *Glycine* (e.g., *G. albicans, G. aphyonota, G. arenari, G. argyrea, G. canescens, G. clandestine, G. curvata, G. cyrtoloba, G. falcate, G. gracei, G. hirticaulis, G. hirticaulis* subsp. *leptosa, G. lactovirens, G. latifolia, G. latrobeana, G. microphylla, G. montis-douglas, G. peratosa, G. pescadrensis, G. pindanica, G. pullenii, G. rubiginosa, G. stenophita, G. syndetika, G. tabacina, G. tomentella, G. soja*, and *G. max* (soybean)); peanut; *Phaseolus vulgaris, Vicia faba*; and *Pisum sativum*.

In some embodiments, a genetically modified plant is a plant that is known to produce compounds used as pharmaceutical agents, flavoring agents, nutraceutical agents, functional food ingredients or cosmetically active agents, or a plant that is genetically engineered to produce these compounds/agents.

In other embodiments, the genetically modified plant is an oilseed plant, wherein the oilseeds, and/or the oil therefrom, contain a modified oil profile with respect to a wild-type plant of the same species (e.g., expression of LC-PUFAs in unusual amounts, omega oil content, and increased oil content).

In alternative embodiments, a transgenic plant or seed comprising a heterologous, synthetic polynucleotide encoding a polypeptide of interest as described herein may also may comprise at least one other transgenic event in its genome, including without limitation: a gene encoding an insecticidal protein (e.g., a *Bacillus thuringiensis* insecticidal protein); an herbicide tolerance gene (e.g., a gene providing tolerance to glyphosate); and a gene contributing to a desirable phenotype in the transgenic plant, such as increased yield, altered fatty acid metabolism, or restoration of cytoplasmic male sterility. In particular embodiments, a synthetic polynucleotide encoding a polypeptide of interest is combined with such additional transgenes, either by recombinant DNA techniques or conventional breeding with a plant already comprising the additional transgene(s).

Also included in some embodiments are parts of a plant comprising a heterologous, synthetic polynucleotide encoding a polypeptide of interest as described herein. Such plant parts include any parts of a plant, including, for example and without limitation, seeds (including mature seeds and immature seeds); tissues; pollen; embryos; flowers; fruits; shoots; leaves; roots; stems; and explants. Particular embodiments include descendants of a plant comprising a heterologous, synthetic polynucleotide encoding a polypeptide of interest as described herein.

The following examples are provided to illustrate certain particular features and/or embodiments. The examples should not be construed to limit the disclosure to the particular features or embodiments exemplified.

EXAMPLES

Example 1: Evaluation of Multiple DNA Sequences Encoding the Truncated Cry1Ab Protein for the Impact on the Gene Expression in $T_0$ Maize Three different DNA sequences that encode the identical truncated Cry1Ab protein were evaluated. The 3 different versions of the cry1Ab gene were tested in a uniform binary plant transformation vector. The genes were cloned into identical gene expression cassettes with the same selectable marker cassette. The only variable in each plasmid was the actual DNA sequence encoding the truncated cry1Ab gene.

Materials and Methods

Design of synthetic Cry1Ab DNA Sequences. The truncated Cry1Ab protein used in this study consists of amino acids corresponding to those found at positions 1-619 of the native Cry1Ab full length protein. The truncated form of the native cry1Ab gene which encoded amino acids 1-619 was analyzed for the presence of 16 distinct polyadenylation sequences. Table 2. The location and composition of these 16 sequences identified in the native cry1Ab gene were recorded, and were included in the design of the cry1Ab truncated gene sequences that were evaluated.

Three different DNA sequences were designed and created using various concepts on gene redesign. Each version of the cry1Ab gene was trimmed to yield the corresponding protein consisting of amino acids 1-619, and the DNA composition was changed to include the 16 aforementioned polyadenylation sequences found in the native gene, to eliminate an additional putative instability sequence, and a seventeenth polyadenylation sequence beginning at base 1639 was incorporated into the design. This sequence is referred to herein as "IRDIG.1471.4."

Two new versions of the gene were designed to test different redesign hypotheses. The wild-type DNA sequence encoding the Cry1Ab core toxin (SEQ ID NO:30) was translated into the corresponding amino acid sequence, and was then reverse translated using the most preferred codon for each amino acid, using the OPTGENE™ 2.0 software (Ocimum Biosolutions, Banjara Hills Hyderabad, India). The resulting DNA sequence was analyzed, and codons were changed where necessary to restore sequences identified in Table 2, to remove unwanted open reading frames, to remove unwanted restriction sites, and to remove extended runs of G+C and A+T when possible by the substitution of a base to disrupt the consecutive string of either G+C or A+T codons. The resulting encoded amino acid sequence corresponded to the native amino acid sequence. This sequence is referred to herein as "IRDIG.1471.2."

The second sequence design was based on a maize codon distribution table encompassing the distribution of amino acid codons for over 800 maize genes. The amino acid sequence corresponding to the core Cry1Ab protein was reverse translated using the amino acid codon distribution table that corresponded to the levels each codon present in the average maize gene. Rare codons (i.e., codons present 10 percent of the time or less) were not included. The resulting DNA sequence was analyzed, and codons were changed where necessary to remove unwanted open reading frames, to remove unwanted restriction sites, to restore sequences identified in Table 2, and to remove extended runs of G+C and A+T where possible. The resulting encoded amino acid sequence corresponded to the native amino acid sequence. This sequence is referred to herein as "IRDIG.1471.3."

TABLE 2

Sequences found in the native cry1Ab gene were included in the rebuilt genes that were evaluated in this experiment. There is one additional polyadenylation site from the table at 1639 (AATCAA), which is not included in the native sequence but was engineered into the rebuilds because it eliminates an additional putative destabilization sequence.

|  | Sequence | No. sites in native Cry1Ab | Loc. in native Cry1Ab | IRDIG.1471.2 | IRDIG.1471.3 | IRDIG.1471.4 | Loc. in redesigned Cry1Ab |
|---|---|---|---|---|---|---|---|
| 1 | AATAAA | 0 | — | 0 | 0 | 0 | — |
| 2 | AATAAT | 3 | 960, 1126, 1387 | 3 | 3 | 3 | 960, 1126, 1387 |
| 3 | AACCAA | 2 | 253, 280 | 2 | 2 | 2 | 253, 280 |
| 4 | ATATAA | 2 | 185, 1391 | 2 | 2 | 2 | 185, 1391 |
| 5 | AATCAA | 2 | 688, 1129 | 3 | 3 | 3 | 688, 1129, 1639 |
| 6 | ATACTA | 0 | — | 0 | 0 | 0 | — |
| 7 | ATAAAA | 0 | — | 0 | 0 | 0 | — |
| 8 | ATGAAA | 1 | 1232 | 1 | 1 | 1 | 1232 |
| 9 | AAGCAT | 0 | — | 0 | 0 | 0 | — |
| 10 | ATACAT | 1 | 1636 | 1 | 1 | 1 | 1636 |
| 11 | ATACAT | 2 | 1366, 1613 | 2 | 2 | 2 | 1366, 1613 |
| 12 | AAAATA | 0 | — | 0 | 0 | 0 | — |
| 13 | ATTAAA | 3 | 249, 704, 785 | 3 | 3 | 3 | 249, 704, 785 |
| 14 | AATTAA | 0 | — | 0 | 0 | 0 | — |
| 15 | AATACA | 0 | — | 0 | 0 | 0 | — |
| 16 | CATAAA | 0 | — | 0 | 0 | 0 | — |
|  | Total | 16 |  | 17 | 17 | 17 |  |

The 3 different versions of truncated cry1Ab were evaluated for total G+C content. The total ranged from 50.9% to 59.5% G+C. Table 3. Each of the 3 versions of the truncated cry1Ab gene described above was synthesized (DNA2.0; Menlo Park, Calif.).

TABLE 3

The G + C content for each of the 3 different versions of Cry1Ab.

| Cry1Ab Sequence | G + C Content |
|---|---|
| IRDIG.1471.2 | 59.50% |
| IRDIG.1471.3 | 50.90% |
| IRDIG.1471.4 | 51.40% |

Plant Expression Vector Construction. Standard cloning methods were used in the construction of entry vectors containing cry1Ab expression cassettes. Binary plasmids that contained cry1Ab expression cassettes were engineered using GATEWAY® (Invitrogen, Carlsbad, Calif.), and used in *Agrobacterium*-mediated plant transformation. Restriction endonucleases were obtained from New England BioLabs (NEB®; Ipswich, Mass.), and T4 DNA Ligase (Invitrogen) was used for DNA ligation. GATEWAY® reactions were performed using GATEWAY® LR CLONASE® enzyme mix (Invitrogen) for assembling one entry vector and one destination vector. Plasmid preparations were performed using NUCLEOSPIN® Plasmid Kit (Macherey-Nagel Inc., Bethlehem, Pa.) or the Plasmid Midi Kit (QIAGEN) following the instructions of the suppliers. DNA fragments were isolated using QIAQUICK® Gel Extraction Kit (QIAGEN) after agarose Tris-acetate gel electrophoresis.

Three synthetic genes encoding truncated Cry1Ab with the aforementioned DNA design were obtained in plasmids DASDNA441-DASDNA443. Plant expression vector construction was initiated with insertion of each synthetic cry1Ab gene into pDAB101557 between the ZmUbi1 promoter and ZmPer5 3' untranslated region (3' UTR) on a BamHI/SacI fragment, creating entry vectors pDAB111444-pDAB111446. Entry vectors pDAB111444-pDAB111446 were each recombined using GATEWAY® technology with destination vector pDAB109805, which contained the selectable marker cassette SCBV(MAM) promoter v2/AAD-1 v3/ZmLip 3' UTR v1, to create final binary vectors pDAB111447-pDAB111449, respectively.

Colonies of all assembled plasmids were initially screened by restriction digestion of miniprep DNA. Plasmid DNA of selected clones was sequenced by contract with a commercial sequencing vendor (EUROFINS™ MWG Operon, Huntsville, Ala.). Sequence data were assembled and analyzed using the SEQUENCHER™ software (Gene Codes Corp., Ann Arbor, Mich.). Maps of the plasmids reflect the correct sequence. FIG. 1.

*Agrobacterium tumefaciens* Strain Production. The details of the *E. coli*-derived, plasmid DNA used to develop the *Agrobacterium tumefaciens* strains for plant transformation are provided in Table 4. DAt13192, a recA-ternary strain of *A. tumefaciens*, was the base strain selected for the development of these plant transformation strains. Standard transformation protocols were utilized in the development of these strains. The development of the new stably-transformed *A. tumefaciens* strains with the binary vector of interest was confirmed by restriction digest of each strain, resulting in the validation of at least one colony for each construct.

TABLE 4

*E. coli* derived, plasmid DNA used to develop the *A. tumefaciens* strains for plant transformation from strain DAt13192.

Cry1Ab *Agrobacterium* Validation Summary

| Construct | Description | Colony | Result |
|---|---|---|---|
| pDAB111447 | ZmUbil v2/IRDIG.1741.2/ZmPer5::SCBV(MAM)/AAD-1 v3/Zm-Lip | 1 | PASS |
| | | 2 | PASS |
| pDAB111448 | ZmUbil v2/IRDIG.1741.3/ZmPer5::SCBV(MAM)/AAD-1 v3/Zm-Lip | 1 | PASS |
| | | 2 | PASS |
| pDAB111449 | ZmUbil v2/IRDIG.1741.4/ZmPer5::SCBV(MAM)/AAD-1 v3/Zm-Lip | 1 | PASS |
| | | 2 | PASS |

*Agrobacterium* Culture Initiation. Glycerol stocks of the project vectors in the host *A. tumefaciens* strain DAt13192 (RecA minus ternary strain) were obtained, and *Agrobacterium* cultures were streaked from glycerol stocks onto AB minimal medium and incubated at 20° C., in the dark, for 2-3 days. *Agrobacterium* cultures were then streaked onto a plate of YEP medium and incubated at 20° C., in the dark, for 1 day.

On the day of an experiment, a mixture of Inoculation medium and acetosyringone was prepared in a volume appropriate to the number of constructs in the experiment. Table 5. Inoculation medium was pipetted into a sterile, disposable 250 mL flask. A 1 M stock solution of acetosyringone in 100% dimethyl sulfoxide was added to the flask containing Inoculation medium in a volume appropriate to make a final acetosyringone concentration of 200 μM.

TABLE 5

Amount of Inoculation medium/acetosyringone mixture made according to the number of constructs being prepared.

| No. Constructs Prepared | Inoculation Medium (mL) | 1 M acetosyringone stock (μL) |
|---|---|---|
| 1 | 50 | 10 |
| 2 | 100 | 20 |
| 3 | 150 | 30 |
| 4 | 200 | 40 |
| 5 | 250 | 50 |

For each construct, 1-2 loops of *Agrobacterium* from the YEP plate were suspended in 15 mL Inoculation medium/acetosyringone mixture inside a sterile, disposable 50 mL centrifuge tube, and the optical density of the solution at 600 nm ($OD_{600}$) was measured in a spectrophotometer. The suspension was then diluted down to 0.25-0.35 $OD_{600}$ using additional Inoculation medium/acetosyringone mixture. The tube of *Agrobacterium* suspension was then placed horizontally on a platform shaker set at about 75 rpm at room temperature for between 1 and 4 hours before use.

Ear Sterilization and Embryo Isolation. Ears from *Zea mays* cultivar B104 were produced in greenhouse facilities and harvested 10-12 days post-pollination. Harvested ears were de-husked and surface-sterilized by immersion in a 20% solution of commercial bleach (ULTRA CLOROX® Germicidal Bleach, 6.15% sodium hypochlorite) and two drops of TWEEN™ 20, for 20 minutes, followed by three rinses in sterile, deionized water inside a laminar flow hood. Immature zygotic embryos (1.8-2.2 mm long) were aseptically excised from each ear, and distributed into one or more micro-centrifuge tubes containing 2.0 mL *Agrobacterium* suspension into which 2 µl of 10% BREAK-THRU® 5233 surfactant had been added.

*Agrobacterium* Co-cultivation. Upon completion of the embryo isolation activity, the tube of embryos was closed and placed on a rocker platform for 5 minutes. The contents of the tube were then poured out onto a plate of Co-cultivation medium, and the liquid *Agrobacterium* suspension was removed with a sterile, disposable, transfer pipette. Embryos were oriented with the scutellum facing up using a microscope. The co-cultivation plate with embryos was then placed in the back of the laminar flow hood with the lid ajar for a further 15 minutes. The plate was then closed, sealed with 3M micropore tape, and placed in an incubator at 25° C. with 24 hours/day light at approximately 60 µmol $m^{-2}s^{-1}$ light intensity.

Callus Selection and Regeneration of Transgenic Events. Following the co-cultivation period, embryos were transferred to Resting medium. No more than 36 embryos were moved to each plate. The plates were wrapped with 3M micropore tape and incubated at 27° C. with 24 hours/day light at approximately 50 µmol $m^{-2}s^{-1}$ light intensity for 7-10 days. Callused embryos were then transferred onto Selection I medium. No more than 18 callused embryos were moved to each plate of Selection I. The plates were wrapped with 3M micropore tape, and incubated at 27° C. with 24 hours/day light at approximately 50 µmol $m^{-2}s^{-1}$ light intensity for 7 days. Callused embryos were then transferred to Selection II medium. No more than 12 callused embryos were moved to each plate of Selection II. The plates were wrapped with 3M micropore tape and incubated at 27° C. with 24 hours/day light at approximately 50 µmol $m^{-2}s^{-1}$ light intensity for 14 days.

At this stage, resistant calli were moved to Pre-Regeneration medium. No more than 9 calli were moved to each plate of Pre-Regeneration medium. The plates were wrapped with 3M micropore tape, and incubated at 27° C. with 24 hours/day light at approximately 50 µmol $m^{-2}s^{-1}$ light intensity for 7 days. Regenerating calli were then transferred to Regeneration medium in PHYTATRAYS™, and incubated at 25.5° C. with 16 hours light/8 hours dark per day at approximately 90 µmol $m^{-2}s^{-1}$ light intensity for 7-14 days, or until shoots developed. No more than calli were placed in each PHYTATRAY™. Small shoots with primary roots were then isolated, and transferred to Shoot Elongation medium. Rooted plantlets about 6 cm or taller were transplanted into soil, and moved out to a growth chamber for hardening off.

Genomic DNA Isolation for PCR from Plant Tissues. Tissue samples (leaf tear equivalent to 2 leaf punches using a standard paper punch) were collected in 96-well collection plates (QIAGEN #19560). Tissue disruption was performed with a KLECKO™ tissue pulverizer (Garcia Manufacturing, Visalia, Calif.) in BIOSPRINT96™ AP1 lysis buffer with one stainless steel bead. Following tissue maceration, the genomic DNA was isolated in high throughput format using the BIOSPRINT96™ Plant kit (QIAGEN, #69181) using the BIOSPRINT96™ extraction robot. Genomic DNA was diluted 2:3 $DNA/H_2O$ prior to setting up the qPCR reaction to achieve appropriate Cp scores.

qPCR. Transgene detection by hydrolysis probe assay was performed by real-time PCR using the LIGHTCYCLER®480 system (Roche Applied Science). Assays were designed for AAD-1 using PRIMER EXPRESS™ and the 3' region of the ZmUbi1 promoter (zmUbiLNK) and spectinomycin resistance gene (specR) using LIGHTCYCLER® Probe Design Software 2.0. The assays were multiplexed with internal reference assay invertase to ensure gDNA was present in each assay. For amplification, LIGHTCYCLER® 480 Probes Master mix (Roche Applied Science, #04707494001) was prepared at 1× final concentration in a 10 µL volume multiplex reaction containing 0.4 µM primer and 0.2 µM probe. Table 6. A two-step amplification reaction was performed with an extension at 60° C. for 40 seconds with fluorescence acquisition. Table 6.

Cp scores, the point at which the florescence signal crosses the background threshold using the fit points algorithm (LIGHTCYCLER® software release 1.5) and the RELATIVE QUANT™ module (based on the ΔΔCt method), was used to perform the analysis of real time PCR data.

TABLE 6

Primers and probes for HP assay.

| Name | Sequence | Probe |
|---|---|---|
| zmUbiLNK F | TGCAGCAGCTATATGTGGATT (SEQ ID NO: 15) | FAM/BHQ |
| zmUbiLNK R | TCCATGGTGTCGTGTGG (SEQ ID NO: 16) | |
| zmUbiLNK-Probe | AACAACAGGGTGAGCATCGAC (SEQ ID NO: 17) | |
| zmUbiV5LNK R | TCCATTGTTGGATCCTCTAGAG (SEQ ID NO: 27) | |
| | | |
| GAAD1F | TGTTCGGTTCCCTCTACCAA (SEQ ID NO: 18) | FAM/MGB |
| GAAD1R | CAACATCCATCACCTTGACTGA (SEQ ID NO: 19) | |
| GAAD1-Probe | CACAGAACCGTCGCTTCAGCAACA (SEQ ID NO: 20) | |
| | | |
| IVF-Taq | TGGCGGACGACGACTTGT (SEQ ID NO: 21) | HEX/BHQ |
| IVR-TAQ | AAAGTTTGGAGGCTGCCGT (SEQ ID NO: 22) | |
| IV-Probe | CGAGCAGACCGCCGTGTACTTCTACC (SEQ ID NO: 23) | |

TABLE 6 -continued

Primers and probes for HP assay.

| Name | Sequence | Probe |
|---|---|---|
| SPC1S | GACCGTAAGGCTTGATGAA (SEQ ID NO: 24) | Cy5/BHQ |
| SPC1A | CTTAGCTGGATAACGCCAC (SEQ ID NO: 25) | |
| TQSPC-Probe | CGAGATTCTCCGCGCTGTAGA (SEQ ID NO: 26) | |

TABLE 7

Reaction components and conditions for $T_0$ analysis.

Master mix

| Component | Amt (µL) | Stock | Final |
|---|---|---|---|
| 2 X Buffer | 5 | 2 x | 1x |
| GOI Forward | 0.4 | 10 µM | 0.4 |
| GOI Reverse | 0.4 | 10 µM | 0.4 |
| GOI Probe | 0.4 | 5 µM | 0.2 |
| IVF-TQ | 0.4 | 10 µM | 0.4 |
| IVR-TQ | 0.4 | 10 µM | 0.4 |
| IVP-TQ | 0.4 | 5 µM | 0.2 |
| $H_2O$ | 0.6 | | |
| DNA | 2 | | |

Thermocycler conditions

| Activate | 95° C. | 10 min. | Cycles = 40 Acquire |
|---|---|---|---|
| Denature | 95° C. | 10 sec | |
| Extend | 60° C. | 40 sec | |
| Cool | 40° C. | 10 sec | |

Protein Extraction. Plant leaf tissue was sampled at the V3 to V5 stage within a day of bioassay collection. Two 6 mm diameter leaf samples were stored in a 96-well cluster tube rack at −80° C. until the day of analysis. Two DAISY™ steel BB's and 300 µL extraction buffer (PBS solution containing 0.05% TWEEN™ 20 and 5 µL/mL protease inhibitors (SIGMA™ catalog number 9599) were added to each tube. The samples were milled in a KLECKO™ tissue pulverizer for 3 minutes, on maximum setting. 85 µL NUPAGE™ denaturing sample buffer and 15 µL DTT was added to each sample tube. The samples were mixed gently, heated for 5 minutes at 90° C., and then centrifuged at 3,000 rcf. The supernatant was removed, and tested the same day.

Western Blot Production. Conventional electrophoresis and blotting methods (Gallagher et al. (2008) Curr. Prot. Immolunol. 8(10):1-28) were used with INVITROGEN™ devices and basic reagents. A rabbit anti-Cry1Ab core antibody was the primary antibody utilized with a chemiluminescence detection system.

Quantitative Method. The ELISA used for Cry1Ab quantitation in this study was ENVIROLOGIX™ Catalog Number AP003, using a Cry1Ab purified protein as the standard.

$T_0$ Insect Bioassay. Transgenic plants containing single Bt genes were tested for insecticidal activity in bioassays conducted with neonate lepidopteran larvae on leaves from transgenic plants. The lepidopteran species assayed were the European Corn Borer, *Ostrinia nubilalis* Hübner (ECB), and the Corn Earworm, *Helicoverpa zea* (CEW).

32-well trays (C-D International, Pitman, N.J.) were partially filled with a 2% agar solution, and the agar was allowed to solidify. Leaf sections (approximately 1 in$^2$) were taken from each plant, and placed singly into wells of the 32-well trays. One leaf piece was placed into each well, and two leaf pieces were tested per plant and per insect. Insects were mass-infested using a paintbrush, placing 10 neonate larvae into each well. Trays were sealed with perforated sticky lids that allowed ventilation during the test. Trays were placed at 28° C., 40% RH, 16:8 hours light:dark for three days. After the duration of the test, a percent damage score was taken for each leaf piece. Damage scores for each test were averaged, and used alongside protein expression analysis to conduct correlation analyses.

$T_1$ Seed Production. Select events from all three backgrounds were identified for advancement to the next generation based on copy number of the genes, protein expression level as measured by ELISA, protection in the leaf bioassay, and overall plant health. Events that contained the Spectinomycin resistance gene (SpecR) were noted, but not necessarily omitted from advancement; these events were tested in the greenhouse, but were used in winter nursery or field trails.

Events selected for advancement were transplanted into 5 gallon pots. Observations were taken periodically to track any abnormal phenotypes. Shoot bags were placed over the shoots prior to silk emergence to prevent cross-contamination by stray pollen. Any shoots producing silks prior to covering were noted, and the shoot was removed. The second shoot was then covered and used for pollinations. Plants that produced abnormal or no shoots were recorded in the database. Silks were cut back the day prior to pollinations to provide an even brush to accept pollen. Pollen from the inbred cultivar B104 was used for all pollinations. Reciprocal crosses were performed when possible. Pollination information was recorded for tracking purposes in the database. Ears were peeled back at 21 days after pollination to enhance dry down followed by complete harvest (ear removed from plant) at 42 days after pollination. Ears were placed in the dryer for 1 week, followed by seed processing (shelling, counting, and packaging in pre-printed envelopes).

Table 8 describes the components of various media used in the foregoing protocols.

TABLE 8

Plant media components

| Components | Pre or Post Autoclave | Inoculation | Co-cultivation | Resting | Selection I | Selection II |
|---|---|---|---|---|---|---|
| MS salts | Pre | 2.2 g/L | 4.33 g/L | 4.33 g/L | 4.33 g/L | 4.33 g/L |
| Sucrose | Pre | 68.4 g/L | 30 g/L | 30 g/L | 30 g/L | 30 g/L |

TABLE 8-continued

| Plant media components | | | | | | |
|---|---|---|---|---|---|---|
| Glucose | Pre | 36 g/L | | | | |
| MS mod. vitamins | Post | 1 mL/L | 1 mL/L | 1 mL/L | 1 mL/L | 1 mL/L |
| L-proline | Pre | 115 mg/L | 700 mg/L | 700 mg/L | 700 mg/L | 700 mg/L |
| Casein enzymatic hydrolysate | Pre | | 100 mg/L | 100 mg/L | 100 mg/L | 100 mg/L |
| MES | Pre | | | 500 mg/L | 500 mg/L | 500 mg/L |
| Dicamba p.t. liquid | Pre | | 3.3 mg/L | 3.3 mg/L | 3.3 mg/L | 3.3 mg/L |
| pH | | 5.2 | 5.8 | 5.8 | 5.8 | 5.8 |
| NAA p.t. stock | Pre | | | | | |
| ABA | Post | | | | | |
| BA p.t. stock | Pre | | | | | |
| IAA p.t. stock | Post | | | | | |
| Acetosyringone 1M | Post | 200 µM | 200 µM | | | |
| Silver nitrate | Post | | 15 mg/L | 15 mg/L | 15 mg/L | 15 mg/L |
| Cefotaxime | Post | | | 250 mg/L | 250 mg/L | 250 mg/L |
| Haloxyfop | Post | | | | 36.2 µg/L | 181 µg/L |
| Sigma Agar A7921 | Pre | | 7.0 g/L | 7.0 g/L | 7.0 g/L | 7.0 g/L |
| Sterilize | | Filter | Autoclave | Autoclave | Systec | Systec |

| Components | Pre or Post Autoclave | Pre-regen 500 nM haloxyfop | Pre-regen no selection | Regen 500 nM haloxyfop | Regen no selection | Shoot elongation |
|---|---|---|---|---|---|---|
| MS salts | Pre | 4.33 g/L | 4.33 g/L | 4.33 g/L | 4.33 g/L | 4.33 g/L |
| Sucrose | Pre | 45 g/L | 45 g/L | 60 g/L | 60 g/L | 30 g/L |
| Glucose | Pre | | | | | |
| MS mod. vitamins | Post | 1 mL/L | 1 mL/L | 1 mL/L | 1 mL/L | 1 mL/L |
| L-proline | Pre | 350 mg/L | 350 mg/L | | | |
| Casein enzymatic hydrolysate | Pre | 50 mg/L | 50 mg/L | | | |
| MES | Pre | 500 mg/L | 500 mg/L | 500 mg/L | 500 mg/L | 500 mg/L |
| Dicamba p.t. liquid | Pre | | | | | |
| pH | | 5.8 | 5.8 | 5.8 | 5.8 | 5.8 |
| NAA p.t. stock | Pre | 0.5 mg/L | 0.5 mg/L | | | |
| ABA | Post | 2.5 mg/L | 2.5 mg/L | | | |
| BA p.t. stock | Pre | 1.0 mg/L | 1.0 mg/L | | | |
| IAA p.t. stock | Post | | | | | |
| Acetosyringone 1M | Post | | | | | |
| Silver nitrate | Post | 1.0 mg/L | 1.0 mg/L | | | |
| Cefotaxime | Post | 250 mg/L | 250 mg/L | 125 mg/L | 125 mg/L | |
| Haloxyfop | Post | 181 µg/L | | 181 µg/L | | |
| Sigma Agar A7921 | Pre | 7.0 g/L | 7.0 g/L | 7.0 g/L | 7.0 g/L | 5.5 g/L |
| Sterilize | | Systec | Systec | Systec | Systec | Systec |

Aultoclave = 20 min. cycle

Systec = 2 min. cycle

Results and Discussion

Figure 2:
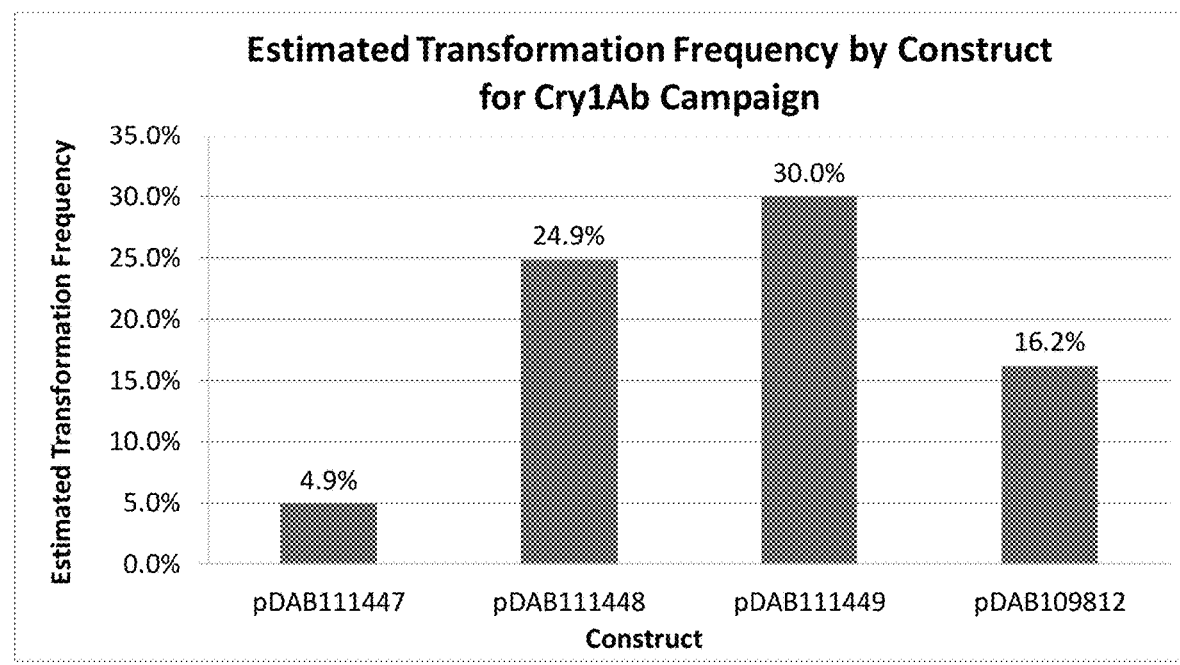
FIG. 2 includes transformation frequencies estimated by construct used for the Cry1Ab transformation. pDAB109812 is the negative control, and this plasmid contains YFP instead of Cry1Ab, but is identical with regard to regulatory elements and the selectable marker cassette.

Transformation Results. Transformation frequencies were estimated for each construct. Table 9. The transformation frequency for each construct was estimated by dividing the number of events that produced at least one plant ready to isolate (Total Regenerable Events) by the sum of all the embryos infected with *Agrobacterium* (Total Embryos Treated). In addition, Table 9 lists the numbers of plants with negative qPCR results from among the total that were tested. There exists a wide degree of variation in the estimated transformation frequency, ranging from 4.9% to 30.0% as shown in FIG. 2.

qPCR Assay for Copy Number Detection. Transgene detection by hydrolysis probe assay was performed by real-time PCR assays designed to identify the copy number of the AAD-1 gene. Because 3 different DNA sequences were implemented, the cry1Ab gene was not the target of the hydrolysis probe assay. Instead, a region of the cry1Ab gene cassette that was present in all of the backgrounds was utilized. The region, located upstream of the cry1Ab gene and consisting of a portion of the ZmUbi1 intron 1 (a polylinker to facilitate cloning and the Kozak sequence preceding the translation start site) was identified. Confirmation of the presence of this region indicated the presence

TABLE 9

Summary of the estimated transformation frequency for each of the individual constructs. At least 25 events were produced for each construct.

| Construct | No. plants analyzed by qPCR | No. plants AAD-1+ and Cry1Ab − | No. plants AAD-1+ and Cry1Ab− | No. plants negative for at least 1 gene | Total regenerable events | Total embryos treated | Estimated transformation frequency |
|---|---|---|---|---|---|---|---|
| pDAB111447 | 34 | 1 | 2 | 3 | 34 | 694 | 4.9% |
| pDAB111448 | 25 | 0 | 0 | 0 | 98 | 394 | 24.9% |
| pDAB111449 | 28 | 0 | 2 | 2 | 69 | 230 | 30.0% |
| pDAB109812 | 7 | 1 | 0 | 1 | 31 | 191 | 16.2% | of cry1Ab gene cassette; it was not used to determine copy number, only the presence or absence of the region.

These two assays (AAD-1 and Cry1Ab linker) were multiplexed with internal reference assay invertase gene to ensure gDNA was present in each assay. Additionally, assays were designed to identify the presence of the specR gene, to determine which events should not be advanced to next generation for use in field testing. Throughout the course of this experiment, the molecular analysis data were implemented to remove negative events or events containing 3 or more copies of the AAD-1 gene from the population, and to ensure that only low copy events containing both the cry1Ab and AAD-1 genes were advanced to the CONVIRON™ and greenhouse for additional testing. All of the backgrounds produced at least 20 low (1-2) copy events. However, the pDAB111447 background produced the highest percentage of single copy events (i.e., 32.3%). Table 10.

Figure 4:
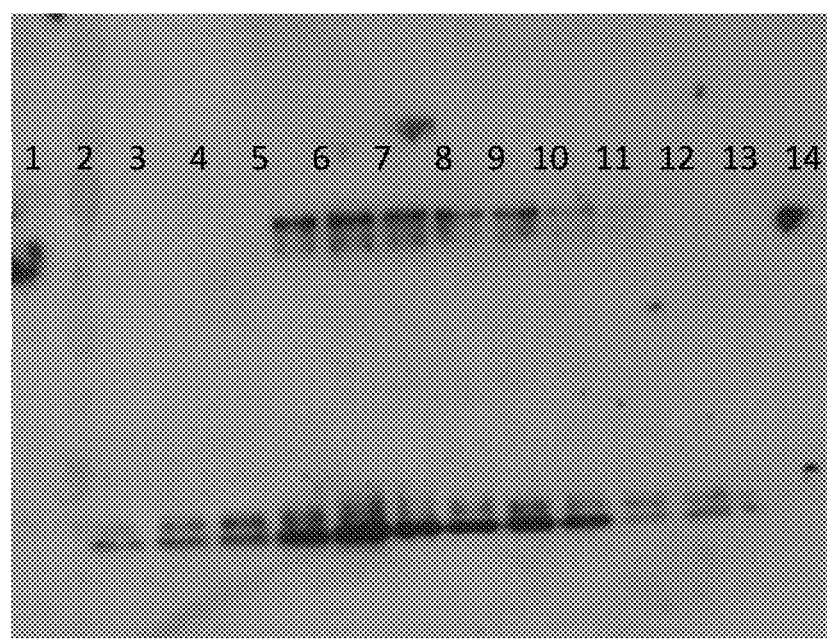
FIG. 4 includes the image of a Western Blot from maize leaf tissue harvested at the V5 stage of development. The contents of the lanes are: Lane 1=negative control; lane 2=BioRad MWM, 20 μL; lane 3=107645[1]-021.001AJ.016; lane 4=107645[1]-021.001AJ.021; lane 5=107645[1]-021.001AJ.006; lane 6=111447[1]-002.001; lane 7=111447[1]-003.001; lane 8=111447[1]-033.001; lane 9=111448[1]-030.001; lane 10=111448[1]-013.001; lane 11=111448[1]-032.001; lane 12=111449[1]-020.001; lane 13=111449[1]-009.001; lane 14=111449[1]-018.001; and lane 15=purified bacterial Cry1Ab standard (1 ng). 107645 events are $T_1$ events that contain full length Cry1Ab that was determined to be active in insect bioassay.

Western blots were completed on select events from each background to ensure that the protein was stable and of the correct size. A representative Western blot consisting of samples from the $T_1$ control (pDAB107645) containing full length Cry1Ab, and $T_0$ events from pDAB111447; pDAB111448; and pDAB111449 is depicted in FIG. 4. The truncated Cry1Ab protein can be detected in events from each of the backgrounds, along with breakdown products of 20 and 18 kD in size. The full length Cry1Ab $T_1$ controls are known to be active in bioassay, and express Cry1Ab below the level of detection for the antibody.

Bioassay Results of $T_0$ Events. Leaf materials from events representing the pDAB111447, pDAB111448 and pDAB111449 backgrounds were collected at the V5 stage of

TABLE 10

Events were analyzed using hydrolysis probe assay for: AAD-1 for copy number determination; a linker region between the maize Ubiquitin promoter and the ATG start of cry1Ab found in all of the backgrounds, for presence or absence; the specR gene for presence or absence; as well as the native maize gene, invertase, for relative strength of signal.

| Plasmid | Description | % GC | AAD-1/GOI +/+ events analyzed | No. 1-copy events | % 1-copy |
| --- | --- | --- | --- | --- | --- |
| pDAB111447 | IRDIG.1741.2 High GC | 59.5 | 31 | 10 | 32.3 |
| pDAB111448 | IRDIG1471.3 Zm Codon bias | 50.9 | 29 | 4 | 13.8 |
| pDAB111449 | IRDIG1471.4 Patent example | 51.4 | 26 | 7 | 26.9 |

| Plasmid | No. LC events (PCR) | % LC | No. HC events (PCR) | SpecR | % SpecR backbone |
| --- | --- | --- | --- | --- | --- |
| pDAB111447 | 25 | 80.6 | 6 | 6 | 19.4 |
| pDAB111448 | 20 | 69.0 | 5 | 6 | 20.7 |
| pDAB111449 | 22 | 84.6 | 4 | 6 | 23.1 |

Figure 3:
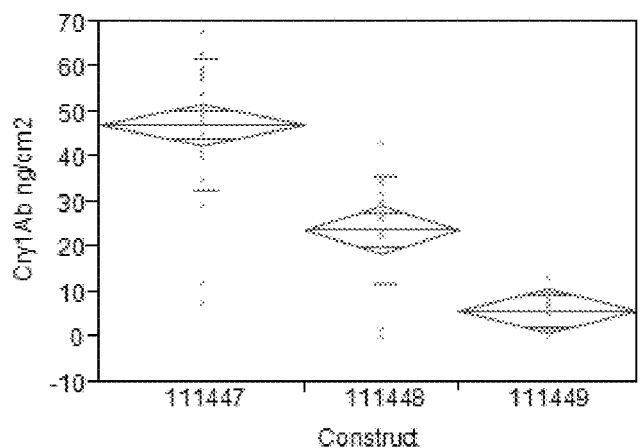
FIG. 3 includes a summary of the statistical analysis of $T_0$ transformation events, obtained by using JMP statistical analysis software for each of the backgrounds. The average is the center line of the green diamond for each of the backgrounds.
Figure 5:
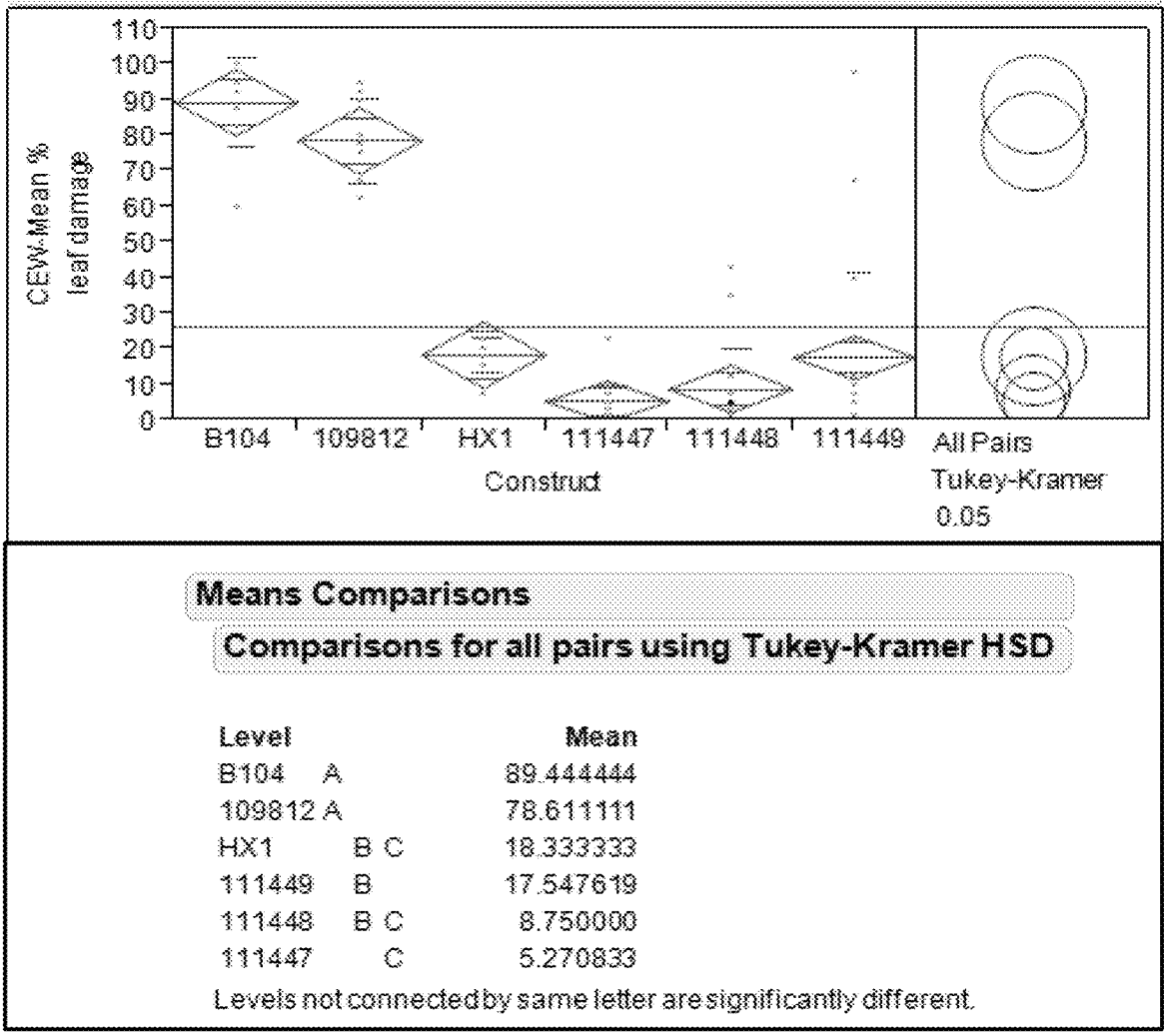
FIG. 5 includes a summary of a Tukey-Kramer Oneway analysis of corn earworm (CEW) percent damage by construct. The control materials, 109812 (YFP), B104 (non-transformed control), and HX1 (HERCULEX®) were evaluated alongside the Cry1Ab events. All three backgrounds containing Cry1Ab provided protection that is equal to that of HERCULEX® against CEW.
Figure 6:
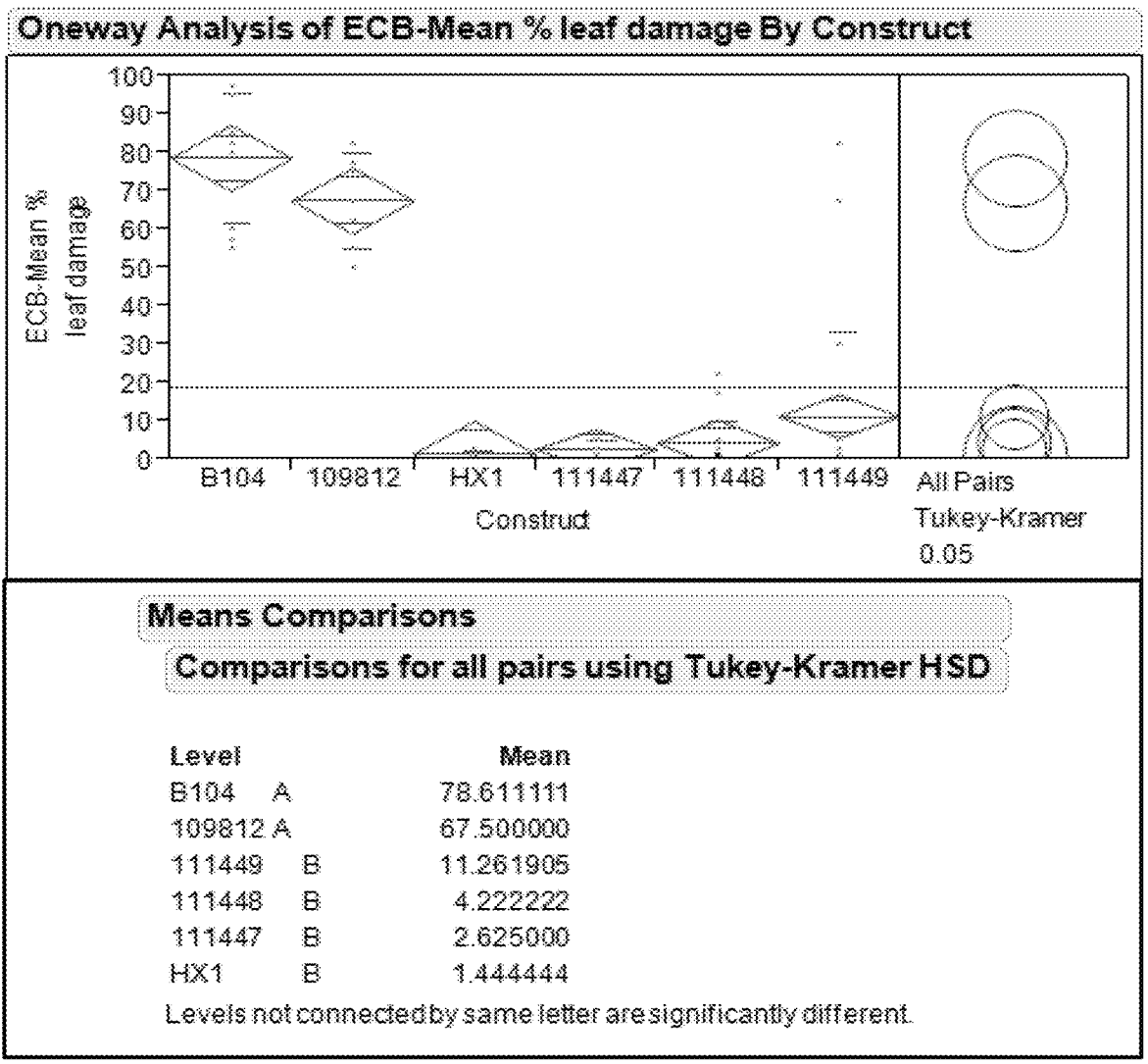
FIG. 6 includes a summary of a Tukey-Kramer Oneway analysis of European corn borer (ECB) percent damage by construct. The control materials, 109812 (YFP), B104 (non-transformed control), and HX1 (HERCULEX®) were evaluated alongside the Cry1Ab events. All three backgrounds containing Cry1Ab provided protection that is equal to that of HERCULEX® against ECB.
Figure 7:
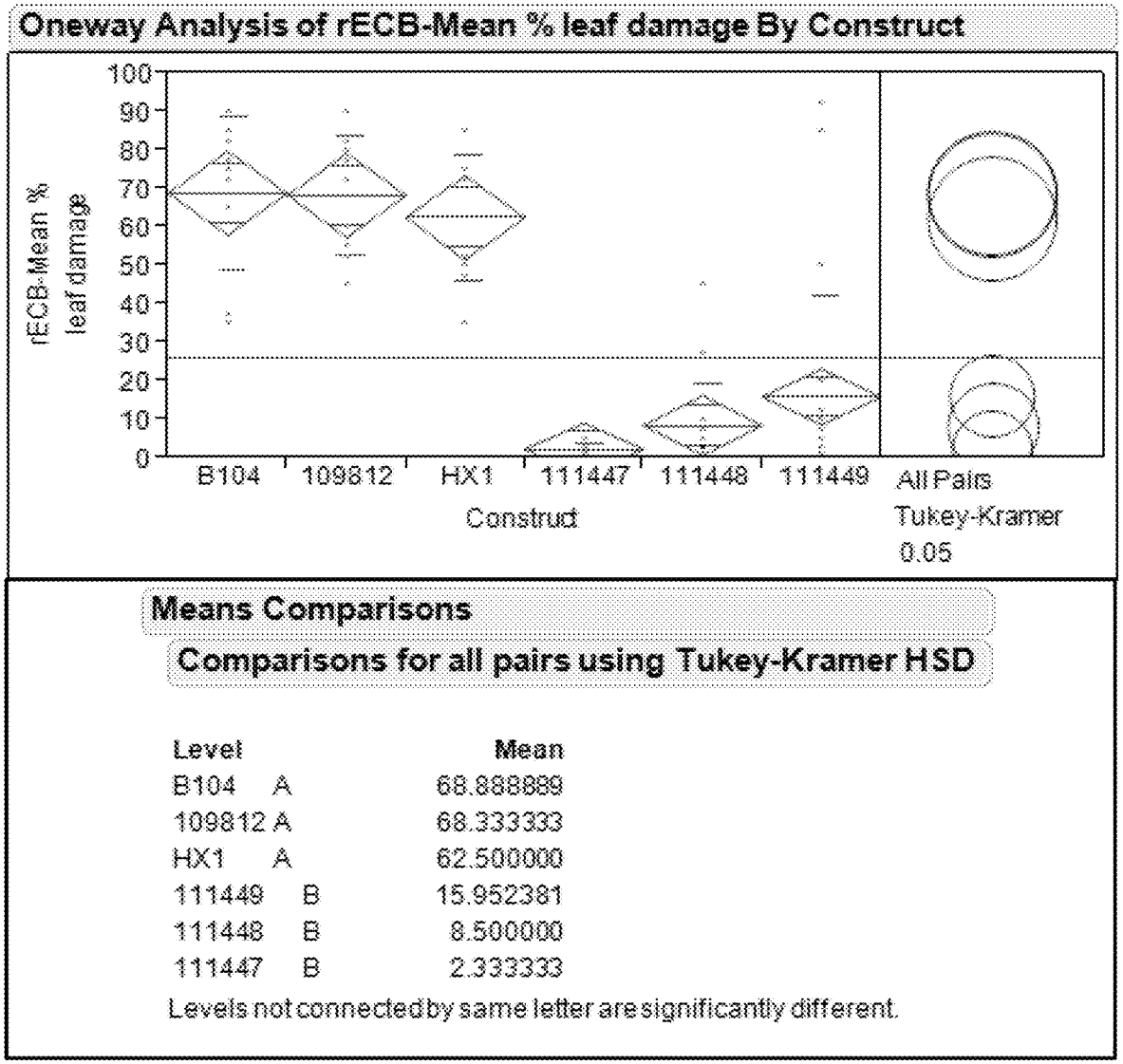
FIG. 7 includes a summary of a Tukey-Kramer Oneway analysis of Cry1Fa-resistant European corn borer (rECB) percent damage by construct. The control materials, 109812 (YFP), B104 (non-transformed control), and HX1 (HERCULEX®) were evaluated alongside the Cry1Ab events. All three backgrounds containing Cry1Ab provided protection against rECB.

Protein Analysis. All of the low copy events that passed the molecular analysis screen from each of the three backgrounds were analyzed for Cry1Ab protein level. The high GC background, pDAB111447, exhibited a significantly higher average expression level of Cry1Ab, as compared to the other two backgrounds, with a value of 45.3 ng/cm². The maize codon-biased background, pDAB111448, had an average expression of 23.8 ng/cm², and the protein described in U.S. Patent Publication No. US 2012/0266335 A1 (pDAB111449) had an average expression level of 5.8 ng/cm². Statistical analyses of the levels of Cry1Ab protein detected in the $T_0$ events from each background are depicted in FIG. 3 and summarized in Table 11.

development, and challenged with CEW, ECB, and Cry1Fa-resistant European corn borer (rECB) larvae. The assay spanned 3 days, and $T_0$ events were evaluated as they reached the V5 developmental stage. The samples were then graded for damage to the leaf tissue. FIGS. 5-7 contain the bioassay results for CEW, ECB, and rECB, respectively. Events from the three constructs performed equally well against all three pests. Each performed as well as the HERCULEX® control against CEW and ECB, and each had less than 20% leaf damage against rECB.

TABLE 11

The number of events for each background that were included in the quantitative ELISA determination of the Cry1Ab protein expression. The average expression ranged from 5.8 to 45.3 ng/cm² from the different backgrounds.

| Background | Description | No. events tested | Avg. expression (ng/cm²) |
| --- | --- | --- | --- |
| pDAB111447 | IRDIG.1741.2 High GC | 25 | 45.3 |
| pDAB111448 | IRDIG1471.3 Zm Codon bias | 18 | 23.8 |
| pDAB111449 | IRDIG1471.4 Patent example | 21 | 5.8 |

Pollinations. High expressing, single copy events as determined by AAD-1 analysis, which were also determined to be positive for the Cry1Ab gene cassette were considered for advancement to the $T_1$ generation. Events containing the SpecR gene were omitted from the advancement process. Ten events from each background were advanced to the $T_1$ generation. The plants were cross-pollinated with B104 donor events in reciprocal fashion to ensure that the seed is recovered for evaluation at the $T_1$ generation. The events that were advanced to $T_1$ seed production are shown in Table 12.

TABLE 12

Summary of the data for each of the events that were advanced for $T_1$ seed production. All events were positive for detection of ZmUbil-linker, and negative for detection of SpecR. Each event was cross pollinated with B104.

| Subject ID | AAD-1 v3 copy | Cry1Ab ELISA (ng/cm$^2$) | CEW mean % leaf damage | ECB mean % leaf damage | rECB mean % leaf damage |
|---|---|---|---|---|---|
| 111447[1]-010.001 | 1.3 | 49 | 3 | 1 | 1 |
| 111447[1]-012.001 | 1.3 | 35 | 3 | 1 | 5 |
| 111447[1]-023.001 | 1.5 | 45 | 5 | 1 | 3 |
| 111447[1]-002.001 | 1.6 | 68 | 5 | 1 | 3 |
| 111447[1]-003.001 | 1.6 | 63 | 5 | 1 | 3 |
| 111447[1]-006.001 | 1.6 | 59 | 5 | 3 | 3 |
| 111447[1]-007.001 | 1.7 | 45 | 1 | 1 | 1 |
| 111447[1]-008.001 | 1.7 | 48 | 5 | 1 | 1 |
| 111447[1]-013.001 | 1.8 | 51 | 3 | 1 | 1 |
| 111447[1]-021.001 | 1.8 | 50 | 1 | 1 | 1 |
| 111448[1]-022.001 | 1.0 | 29 | 3 | 3 | 7.5 |
| 111448[1]-021.001 | 1.1 | 23 | 5 | 3 | 5 |
| 111448[1]-013.001 | 1.4 | 35 | 1 | 1 | 5 |
| 111448[1]-015.001 | 1.5 | 27 | 5 | 3 | 5 |
| 111448[1]-020.001 | 1.5 | 30 | 3 | 1 | 5 |
| 111448[1]-002.001 | 1.6 | 20 | 5 | 1 | 3 |
| 111448[1]-003.001 | 1.8 | 27 | 3 | 1 | 1 |
| 111448[1]-030.001 | 1.9 | 43 | 5 | 1 | 5 |
| 111448[1]-033.001 | 1.8 | 32 | 3 | 1 | 1 |
| 111448[1]-032.001 | 1.9 | 34 | 5 | 3 | 5 |
| 111449[1]-025.001 | 1.2 | 7.3 | 10 | 3 | 10 |
| 111449[1]-008.001 | 1.3 | 9.9 | 10 | 5 | 5 |
| 111449[1]-012.001 | 1.4 | 6.9 | 10 | 5 | 3 |
| 111449[1]-017.001 | 1.5 | 6.8 | 5 | 3 | 1 |
| 111449[1]-020.001 | 1.5 | 13 | 10 | 1 | 7.5 |
| 111449[1]-026.001 | 1.6 | 5 | 5 | 1 | 3 |
| 111449[1]-027.001 | 1.7 | 9.3 | 5 | 3 | 5 |
| 111449[1]-009.001 | 1.8 | 10 | 5 | 1 | 3 |
| 111449[1]-023.001 | 1.8 | 7 | 5 | 3 | 5 |
| 111449[1]-024.001 | 2.0 | 8.1 | 1 | 5 | 3 |

Conclusions

Multiple DNA sequences were evaluated that would encode the truncated Cry1Ab protein, and pDAB111447 (additionally modified to include a specific set of polyadenylation sequences that were identified in the native gene DNA composition at the identical nucleotide position in the rebuilt gene) was identified as an unexpectedly superior gene that will be utilized in an above-ground Lepidoptera control gene stack. Three different DNA sequences, encompassing various DNA design methodologies, were evaluated in maize at the $T_0$ generation. All three of the DNA sequences were combined with a binary plant transformation plasmid consisting of identical components for the expression of the Cry1Ab protein. Only the DNA sequence itself was varied between constructs.

Protein expression ranged from a low of 5.8 ng/cm$^2$ for the average expression in the $T_0$ population (observed in the pDAB111449 background) to a high of 45.3 ng/cm$^2$, as detected in the pDAB111447 background. Thus, pDAB111447 provides an 8-fold increase. Individual events were recorded to express the Cry1Ab protein in amounts as high as 68 ng/cm$^2$ in the pDAB111447 background. pDAB111447 also produced the largest percentage of single copy events compared to the other two backgrounds. However, the transformation efficiency with pDAB111447 was much lower (4.5%), in comparison to the other two backgrounds (both about 25%).

The collective expression of Cry1Ab protein measured in the events from the pDAB111447 background, and the activity against CEW, ECB, and rECB in the insect leaf bioassay, were key factors in advancing this DNA sequence for an above-ground Lepidoptera pest gene stack. This version of truncated Cry1Ab will be combined with a Cry1Fa gene in some exemplary gene stacks.

Example 2: Evaluation of Multiple DNA Sequences Encoding the Truncated Cry1Fa Protein for the Impact on the Gene Expression in $T_0$ Maize This experiment evaluated 11 different DNA sequences that encode the identical truncated Cry1Fa protein. The 11 different versions of the truncated cry1Fa gene were tested in a uniform binary plant transformation vector. The genes were cloned into identical gene expression cassettes having the same selectable marker cassette. The only variable in each plasmid is the actual DNA sequence encoding the truncated Cry1Fa protein.

Materials and Methods

Design of synthetic Cry1Fa genes. The truncated Cry1Fa protein used in this study consists of amino acids corresponding to those found at positions 1-605 of the native Cry1Fa full length protein. The truncated form of the native cry1Fa gene that encoded amino acids 1-605 was analyzed for the presence of 16 distinct polyadenylation sequences. Table 13. The location and composition of these 22 sequences were recorded, and are included in the design of the cry1Fa truncated gene sequences that were evaluated.

Eleven different cry1Fa gene sequences were designed to test different redesign hypotheses. Pre-existing versions of Cry1Fa include a maize codon-biased sequence, 2 plant codon-biased sequences, and one described in U.S. Patent Publication No. US 2012/0266335 A1. Each version of the cry1Fa gene was trimmed to yield the corresponding protein consisting of amino acids 1-605, and the DNA composition was changed to include the 22 aforementioned polyadenylation sequences found in the native gene.

Several new versions of the gene were designed to test different redesign hypotheses. The wild-type DNA sequence encoding the Cry1Fa core toxin (SEQ ID NO:31) was translated into the corresponding amino acid sequence, and it was then reverse translated using the most preferred codon for each amino acid, using the OPTGENE™ 2.0 software (Ocimum Biosolutions, Banjara Hills Hyderabad, India). The resulting DNA sequence was analyzed and codons were substituted, where necessary, to restore sequences identified in Table 13, to remove unwanted open reading frames, and to remove unwanted restriction sites. Extended runs of G+C and A+T were ignored in this initial gene design. The amino acid sequence was preserved, and the resulting DNA sequence is referred to herein as "IRDIG.586.34." IRDIG.586.34 was further modified, eliminating the runs of G+C and A+T that extended six bases or longer, by substitution of a base to disrupt the consecutive string of either G+C or A+T codons where possible. As before, the amino acid sequence composition was preserved. The resulting DNA sequence is referred to herein as "IRDIG.586.35."

The pre-existing maize codon-biased cry1Fa gene was modified by restoring the sequences identified in Table 13, while preserving the amino acid sequence. The resulting DNA sequence is referred to herein as "IRDIG.586.36." IRDIG.586.36 was further modified by analyzing the DNA and changing codons when necessary to remove unwanted open reading frames, and to remove unwanted restriction sites, while preserving the amino acid sequence. The resulting DNA sequence is referred to herein as "IRDIG.586.37."

Two pre-existing plant codon-biased versions of the cry1Fa gene were modified, again by restoring the sequences identified in Table 13. The amino acid sequence of each was preserved. The resulting DNA sequences are referred to herein as "IRDIG.586.38" and "IRDIG.586.42," respectively. IRDIG.586.38 was further modified by analyzing the DNA and changing codons when necessary to remove unwanted open reading frames, and to remove unwanted restriction sites. The amino acid sequence was preserved. The resulting DNA sequence is referred to herein as "IRDIG.586.39."

The truncated Cry1Fa sequence described in U.S. Patent Publication No. US 2012/0266335 A1 was utilized for comparison. This sequence is referred to herein as "IRDIG.586.40." IRDIG.586.40 was further modified, eliminating the runs of G+C and A+T that extend six bases or longer, by substitution of a base to disrupt the consecutive string of either G+C or A+T codons where possible, while preserving the amino acid sequence of the encoded product. The resulting DNA sequence is referred to herein as "IRDIG.586.41."

A further sequence was designed specifically by reverse translation using an amino acid codon distribution table that corresponded to the levels at which each codon was present in the average maize gene. Rare codons (i.e., codons present 10% or less) were not included. The resulting DNA sequence was analyzed, and codons were changed where necessary to remove unwanted open reading frames, to remove unwanted restriction sites, to restore sequences identified in Table 13, and to remove extended runs of G+C and A+T where possible. The resulting DNA sequence is referred to herein as "IRDIG.586.43."

TABLE 13

Sequences found in the native cry1Fa gene that were included in the rebuilt genes evaluated in this experiment. The AATAAA sequences found in the native gene staring at nucleotide position 426 and 582 were changed to AATCAA at the same locations in the rebuilt genes.

| Sequence | No. sites in native Cry1Ab | Loc. in native Cry1Ab | IRDIG.586.34-IRDIG.586.43 | Loc. in redesigned Cry1Fa |
|---|---|---|---|---|
| AATAAA | 2 | 426, 582 | 0 | — |
| AATAAT | 5 | 7, 46, 358, 430, 562 | 5 | 7, 46, 358, 430, 562 |
| AACCAA | 0 | — | 0 | — |
| ATATAA | 1 | 1520 | 1 | 1520 |
| AATCAA | 2 | 19, 628 | 4 | 19, 426, 582, 628 |
| ATACTA | 1 | 1508 | 1 | 1508 |
| ATAAAA | 0 | — | 0 | — |
| ATGAAA | 2 | 314, 1211 | 2 | 314, 1211 |
| AAGCAT | 0 | — | 0 | — |
| ATTAAT | 2 | 579, 1690 | 2 | 579, 1690 |
| ATACAT | 0 | — | 0 | — |
| AAAATA | 0 | — | 0 | — |
| ATTAAA | 2 | 66, 1266 | 2 | 66, 1266 |
| AATTAA | 2 | 368, 779 | 2 | 368, 779 |
| AATACA | 3 | 400, 1369, 1693 | 3 | 400, 1369, 1693 |

TABLE 13 -continued

Sequences found in the native cry1Fa gene that were included in the rebuilt genes evaluated in this experiment. The AATAAA sequences found in the native gene staring at nucleotide position 426 and 582 were changed to AATCAA at the same locations in the rebuilt genes.

| Sequence | No. sites in native Cry1Ab | Loc. in native Cry1Ab | IRDIG.586.34-IRDIG.586.43 | Loc. in redesigned Cry1Fa |
|---|---|---|---|---|
| CATAAA | 0 | — | 0 | — |
| Total | 22 | | 22 | |

The 11 different versions of the truncated cry1Fa gene were evaluated for total G+C content. The total ranged from a low of 46.9% G+C in IRDIG.586.38, to a high of 64.1% G+C in IRDIG.568.36. The G+C content for each version of the gene, including the HERCULEX® Cry1Fa gene (i.e., "Cry1F trunc HX"), is found in Table 14.

TABLE 14

The G + C content for each of the 11 different versions of Cry1Fa.

| Cry1Fa Sequence | G + C Content |
|---|---|
| IRDIG.568.34 | 61.40% |
| IRDIG.568.35 | 59.80% |
| IRDIG.568.36 | 64.10% |
| IRDIG.568.37 | 60.80% |
| IRDIG.568.38 | 46.90% |
| IRDIG.568.39 | 48.30% |
| IRDIG.568.40 | 48.70% |
| IRDIG.568.41 | 49.10% |
| IRDIG.568.42 | 48.50% |
| IRDIG.568.43 | 53.80% |
| Cry1F trunc Hx | 48.50% |

Each of the 10 truncated cry1Fa genes described above (IRDIG.568.34-IRDIG.568.43) was synthesized (DNA2.0; Menlo Park, Calif.).

Plant Expression Vector Construction. Standard cloning methods were used in the construction of entry vectors containing cry1Fa expression cassettes. See, e.g., Sambrook et al. (1989) *Molecular Cloning: A Laboratory Manual, 2nd* Ed., Cold Spring Harbor Laboratory Press, Cold Spring Harbor, N.Y. *Agrobacterium* binary plasmids that contained cry1Fa expression cassettes were engineered using GATE-WAY® (Invitrogen, Carlsbad, Calif.), and were used in *Agrobacterium*-mediated plant transformation. Restriction endonucleases were obtained from New England BioLabs (NEB™; Ipswich, Mass.), and T4 DNA Ligase (Invitrogen) was used for DNA ligation. PCR amplification was performed using PHUSION™ High-Fidelity DNA Polymerase (NEB) and primers synthesized by Integrated DNA Technologies Inc. (IDT™; Coralville, Iowa). GATEWAY® reactions were performed using GATEWAY® LR CLONASE® enzyme mix (Invitrogen) for assembling one entry vector and one destination vector. Plasmid preparations were performed using NUCLEOSPIN® Plasmid Kit (Macherey-Nagel Inc., Bethlehem, Pa.) or the Plasmid Midi Kit (QIAGEN) following the instructions of the suppliers. DNA fragments were isolated using QIAQUICK® Gel Extraction Kit (QIAGEN) after agarose Tris-acetate gel electrophoresis.

Ten synthetic genes encoding Cry1Fa according to the foregoing DNA designs were obtained in plasmids DAS-DNA426-DASDNA435. Plant expression vector construction was initiated with insertion of each synthetic cry1Fa gene into pDAB101557, between the ZmUbi1 promoter and ZmPer5 3' untranslated region (3' UTR) on a BamHI/SacI fragment, creating entry vectors pDAB111424-pDAB111433, respectively. Entry vectors pDAB111424 through pDAB111433 were each recombined using GATEWAY® technology with destination vector pDAB109805, which contained the selectable marker cassette SCBV (MAM) promoter v2/AAD-1 v3/ZmLip 3'UTR v1, to create final binary vectors pDAB111434-pDAB111443, respectively.

Two additional plant expression vectors were assembled with the truncated cry1Fa gene from pMYC2405. The first of these included a cry1Fa-containing fragment that was PCR amplified from pMYC2405 with primers pMYC2405 F (GATCATACCATGGAGAACAACATACAGAATCA-GTGC; SEQ ID NO:28) and pMYC2405 R (GATCTC-GAGCTCGCGAAAGCTTGGC; SEQ ID NO:29). The 1869 bp amplified fragment was digested with NcoI/SacI and inserted into pDAB101557 to create entry vector pDAB110830, which was subsequently recombined using GATEWAY® technology with destination vector pDAB109805, to create pDAB110839. The final plasmid was assembled by inserting the SacI-blunted EcoRI fragment from pMYC2405 into pDAB110831, creating entry vector pDAB110833. A GATEWAY® recombination reaction with pDAB110833 and pDAB109805 resulted in pDAB110842.

Figure 8:
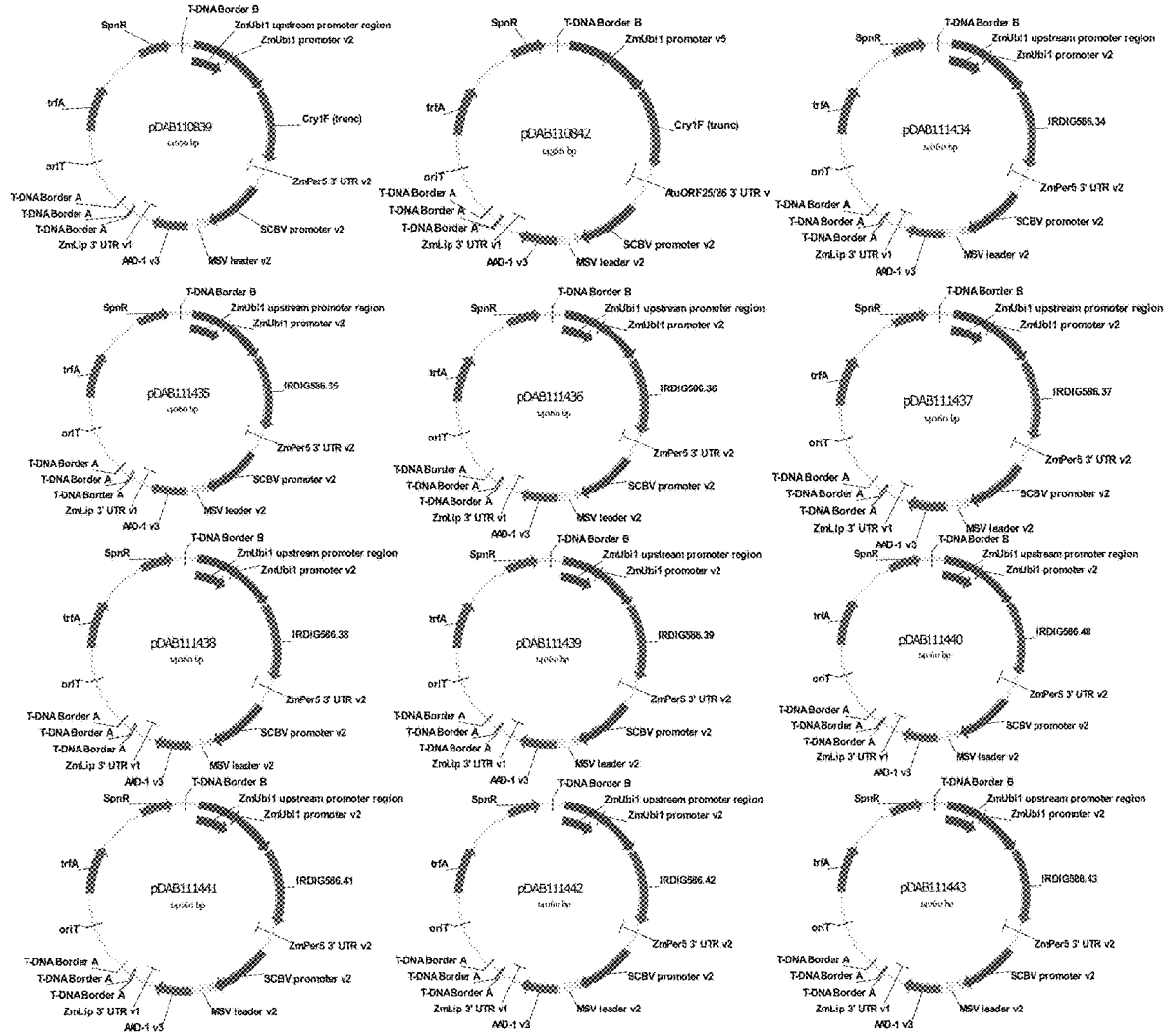
FIG. 8 includes maps of the twelve binary plasmids used in the Cry1Fa corn transformation experiment. All of the plasmids except pDAB110842 are identical, other than the polynucleotide encoding the Cry1Fa. The binary plasmid pDAB110842 has the gene cassette most similar to the HERCULEX® product, including the ZmUbi1 promoter v6 and the AtuORF25/26 3' UTR v1.

Colonies of all assembled plasmids were initially screened by restriction digestion of miniprep DNA. Plasmid DNA of selected clones was sequenced (EUROFINS™ MWG Operon, Huntsville, Ala.), and sequence data were assembled and analyzed using SEQUENCHER™ software (Gene Codes Corp., Ann Arbor, Mich.). Maps of the plasmids reflect the correct sequence. FIG. 8.

*Agrobacterium tumefaciens* Strain Production. The details of the *E. coli*-derived, plasmid DNA used to develop the *A. tumefaciens* strains for plant transformation are provided in Table 15. DAt13192, a recA-ternary strain of *A. tumefaciens*, was the base strain selected for the development of these plant transformation strains, using standard transformation protocols. The development of the new stably-transformed *A. tumefaciens* strains with the binary vector of interest was confirmed by restriction digest of each strain, resulting in the validation of at least one colony for each construct.

TABLE 15

E. coli derived, plasmid DNA used to develop the *A. tumefaciens* strains for plant transformation.

Cry1Fa *Agrobacterium* Validation Summary

| Construct | Description | Colony | Result |
|---|---|---|---|
| pDAB111434 | ZmUbi1 v2/IRDIG.586.34/ZmPer5::SCBV(MAM)/AAD-1 v3/ZmLip | 1 | PASS |
| | | 2 | fail |
| pDAB111435 | ZmUbi1 v2/IRDIG.586.35/ZmPer5::SCBV(MAM)/AAD-1 v3/ZmLip | 1 | PASS |
| | | 2 | PASS |
| pDAB111436 | ZmUbi1 v2/IRDIG.586.36/ZmPer5::SCBV(MAM)/AAD-1 v3/ZmLip | 1 | PASS |
| | | 2 | PASS |
| pDAB111437 | ZmUbi1 v2/IRDIG.586.37/ZmPer5::SCBV(MAM)/AAD-1 v3/ZmLip | 1 | PASS |
| | | 2 | fail |
| pDAB111438 | ZmUbi1 v2/IRDIG.586.38/ZmPer5::SCBV(MAM)/AAD-1 v3/ZmLip | 1 | PASS |
| | | 2 | PASS |
| pDAB111439 | ZmUbi1 v2/IRDIG.586.39/ZmPer5::SCBV(MAM)/AAD-1 v3/ZmLip | 1 | PASS |
| | | 2 | fail |
| pDAB111440 | ZmUbi1 v2/IRDIG.586.40/ZmPer5::SCBV(MAM)/AAD-1 v3/ZmLip | 1 | PASS |
| | | 2 | fail |
| pDAB111441 | ZmUbi1 v2/IRDIG.586.41/ZmPer5::SCBV(MAM)/AAD-1 v3/ZmLip | 1 | PASS |
| | | 2 | PASS |
| pDAB111442 | ZmUbi1 v2/IRDIG.586.42/ZmPer5::SCBV(MAM)/AAD-1 v3/ZmLip | 1 | fail |
| | | 2 | PASS |
| pDAB111443 | ZmUbi1 v2/IRDIG.586.43/ZmPer5::SCBV(MAM)/AAD-1 v3/ZmLip | 1 | PASS |
| | | 2 | PASS |
| pDAB110839 | ZmUbi1 v2/Cry1F (trunc)/ZmPer5::SCBV(MAM)/AAD-1 v3/ZmLip | 1 | PASS |
| | | 2 | PASS |
| pDAB110842 | ZmUbi1 v2/Cry1F (trunc)/AtuORF25::SCBV(MAM)/AAD-1 v3/ZmLip | 1 | PASS |
| | | 2 | PASS |

*Agrobacterium* culture initiation, ear sterilization, embryo isolation, and inoculation and co-cultivation were performed substantially as described in Example I.

Callus Selection and Regeneration of Transgenic Events. Following the co-cultivation period, embryos were transferred to Resting medium. No more than 36 embryos were transferred to each plate. The plates were wrapped with 3M micropore tape, and incubated at 27° C. with 24 hours/day light at approximately 50 µmol m$^{-2}$s$^{-1}$ light intensity for 7-10 days. Callused embryos were then transferred onto Selection I medium. No more than 18 callused embryos were moved to each plate of Selection I. The plates were wrapped with 3M micropore tape, and incubated at 27° C. with 24 hours/day light at approximately 50 µmol m$^{-2}$s$^{-1}$ light intensity for 7 days. Callused embryos were then transferred to Selection II medium. No more than 12 callused embryos were moved to each plate of Selection II. The plates were wrapped with 3M micropore tape, and incubated at 27° C. with 24 hours/day light at approximately 50 µmol m$^{-2}$s$^{-1}$ light intensity for 14 days.

At this stage, resistant calli were moved to Pre-regeneration medium. No more than 9 calli were moved to each plate of Pre-regeneration. The plates were wrapped with 3M micropore tape, and incubated at 27° C. with 24 hours/day light at approximately 50 µmol m$^{-2}$s$^{-1}$ light intensity for 7 days. Regenerating calli were then transferred to Regeneration medium in PHYTATRAYS™, and incubated at 25.5° C. with 16 hours light/8 hours dark per day at approximately 90 µmol m$^{-2}$s$^{-1}$ light intensity for 7-14 days, or until shoots developed. No more than 6 calli were placed in each PHYTATRAY™. Small shoots with primary roots were then isolated and transferred to Shoot/root medium. Rooted plantlets about 6 cm or taller were transplanted into soil, and placed in a growth chamber.

Transfer and Establishment of T$_0$ Plants in the Greenhouse. Transgenic plants were assigned unique identifiers (one plant per event) and transferred on a regular basis to the greenhouse. Plants were transplanted from PHYTATRAY™ to small pots (T.O. Plastics, 3.5" SVD, 700022C) filled with growing media (Premier Tech Horticulture, ProMix BX, 0581 P), and covered with a humidome, to help acclimate the plants to the greenhouse environment (Light Exposure Type: Photo or Assimilation; High Light Limit: 1200 PAR; 16-hour day length; 27° C. Day/24° C. Night).

Genomic DNA isolation; qPCR (See Table 7); protein extraction; Western blot production; and quantitative analysis were performed substantially as described in Example I.

T$_1$ Seed Production. Select events containing each of the twelve plasmids were selected for advancement to the next generation, based on copy number of the genes, protein expression level as measured by ELISA, and overall plant health. Events that contained the SpecR gene were tested in the greenhouse but were not used in winter nursery or field trails. Events selected for advancement were transplanted into 5 gallon pots. Observations were taken periodically to track any abnormal phenotypes. Shoot bags were placed over the shoots prior to silk emergence to prevent cross-contamination by stray pollen. Any shoots producing silks prior to covering were noted, and the shoot was removed. The second shoot was then covered and used for pollinations. Plants that produced abnormal or no shoots were recorded in the database. Silks were cut back the day prior to pollinations to provide an even brush to accept pollen. Pollen from the inbred cultivar B104 was used for all pollinations. Reciprocal crosses were performed when possible. Pollination information was recorded for tracking purposes. Ears were peeled back at 21 days after pollination to enhance dry down, followed by complete harvest (ear removed from plant) at 42 days after pollination. Ears were placed in the dryer for 1 week, followed by seed processing (shelling, counting, packaging in pre-printed envelopes).

Results and Discussion

Figure 9:
FIG. 9 includes an image showing that plants from the pDAB111436 and pDAB11437 backgrounds demonstrated negative agronomic phenotypes. Red discoloration of the stem and leaf material, and severe curling in the leaf and stem tissue, were detected.

Transformation. The transformation efficiencies for each construct were calculated and assembled in Table 16. There exists a wide degree of variation in the transformation frequency, ranging from 4% to 23%. The pDAB111434 and pDAB111436 backgrounds had the lowest transformation efficiency (5% and 4%, respectively), while the pDAB111435 and pDAB110839 backgrounds exhibited the highest rates of transformation (each reaching 23%). Plantlets emerging from pDAB111436 and pDAB111437 demonstrated discoloration in the shoots and leaflets, and epinasty in the leaf and stems. FIG. 9. The majority of these events did not survive, and were not analyzed by molecular analysis.

sequences were utilized, the cry1Fa gene was not the target of the hydrolysis probe assay. Instead, a region of the cry1Fa gene cassette that was present in all of the backgrounds was utilized. This region, located upstream of the cry1Fa gene and consisting of a portion of the ZmUbi1 intron 1, a polylinker to facilitate cloning and the Kozak sequence preceding the translation start site, was identified. Confirmation of the presence of this region indicated the presence of the cry1Fa gene cassette; it was not used to determine copy number. These two assays (AAD-1 and Cry1Fa linker) were multiplexed with an internal reference assay invertase

TABLE 16

Summary of the transformation frequency (adjusted to AAD-1) for each of the individual plasmids. At least 25 events were produced for each of the backgrounds. However, many plantlets from the pDAB11436 background contained red pigmentation and demonstrated stem and leaf curling, and were not healthy enough to be advanced for analysis.

| Construct | No. plants analyzed by qPCR | No. plants AAD-1- | Total regenerable events | Total embryos treated | Transformation frequency (adjusted AAD-1) |
|---|---|---|---|---|---|
| pDAB110839 | 37 | 0 | 115 | 504 | 23% |
| pDAB110842 | 45 | 0 | 73 | 520 | 14% |
| pDAB111434 | 35 | 0 | 38 | 718 | 5% |
| pDAB111435 | 40 | 0 | 116 | 504 | 23% |
| pDAB111436 | 22 | 0 | 25 | 572 | 4% |
| pDAB111437 | 32 | 0 | 52 | 504 | 10% |
| pDAB111438 | 34 | 3 | 44 | 500 | 9% |
| pDAB111439 | 39 | 2 | 66 | 724 | 9% |
| pDAB111440 | 30 | 0 | 54 | 504 | 11% |
| pDAB111441 | 31 | 0 | 34 | 504 | 7% |
| pDAB111442 | 36 | 1 | 91 | 504 | 18% |
| pDAB111443 | 29 | 1 | 53 | 504 | 11% |
| Total | 410 | 7 | 761 | 6562 | 12 |
| pDAB10981 (control) | 7 | 0 | 50 | | 25 |

The various cry1F-containing backgrounds were compared to determine the statistical significance of the effect DNA sequence had on the transformation. The number of events produced was compared as a percentage of the total number of embryos treated, to generate a transformation frequency. Use of JMP™ statistical software to complete a contingency analysis determined that backgrounds pDAB111435, pDAB110839, and pDAB111442 were statistically equal for transformation frequency, at the 0.05 level of significance. Transformation frequency with pDAB110842, pDAB111440, pDAB111443, pDAB111437, pDAB111438, and pDAB111439 were all statistically equal. Additionally, pDAB111441, pDAB111434 and pDAB111436 were all statistically equal as the DNA sequences providing the lowest transformation frequencies.

qPCR Assay for Copy Number Detection. Transgene detection by hydrolysis probe assay was performed by real-time PCR. Assays were designed to identify the copy number of the AAD-1 gene. Because 11 different DNA gene to ensure gDNA was present in each assay. Additionally, assays were designed to identify the presence of the specR gene, to determine which events should not be advanced to next generation for use in field testing. Negative events and events containing 3 or more copies of the AAD-1 gene were removed from the population and to ensure that only low copy events containing both the cry1Fa and AAD-1 genes were advanced to the CONVIRON™ and greenhouse for additional testing. Table 17 contains a summary of the analyses conducted on the events from each back ground.

Events from the pDAB111435 background (23% transformation frequency) also had the highest percent of single copy and low copy events (51.4% and 91.9%, respectively), with 24% of the events testing positive for the spectinomycin resistance gene. pDAB111436 had the lowest percentage of single copy events (5.3%; 1 event), and also had the highest percentage of events with backbone contamination (52.6%).

TABLE 17

Events were analyzed using hydrolysis probe for: AAD-1 for copy number determination; a linker region between the maize Ubiquitin promoter and the ATG start of cry1Fa found in all of the backgrounds for presence or absence; the specR gene for presence or absence; as well as the native maize gene, invertase, for relative strength of signal.

| Plasmid | Description | % GC | AAD-1/GOI +/+ events analyzed | No. 1-copy events | % 1-copy |
|---|---|---|---|---|---|
| pDAB110839 | Cry1Fa HX gene | 48.5% | 36 | 11 | 30.6% |
| pDAB110842 | Cry1Fa HX cassette | 48.5% | 42 | 8 | 19.0% |
| pDAB111434 | IRDIG.586.34 | 61.4% | 31 | 10 | 32.3% |

TABLE 17-continued

Events were analyzed using hydrolysis probe for: AAD-1 for copy number determination; a linker region between the maize Ubiquitin promoter and the ATG start of cry1Fa found in all of the backgrounds for presence or absence; the specR gene for presence or absence; as well as the native maize gene, invertase, for relative strength of signal.

| | | | | | |
|---|---|---|---|---|---|
| pDAB111435 | IRDIG.586.35 | 59.8% | 37 | 19 | 51.4% |
| pDAB111436 | IRDIG.586.36 | 64.1% | 19 | 1 | 5.3% |
| pDAB111437 | IRDIG.586.37 | 60.8% | 37 | 5 | 13.5% |
| pDAB111438 | IRDIG.586.38 | 46.9% | 30 | 7 | 23.3% |
| pDAB111439 | IRDIG.586.39 | 48.3% | 33 | 5 | 15.2% |
| pDAB111440 | IRDIG.586.40 | 48.7% | 26 | 5 | 19.2% |
| pDAB111441 | IRDIG.586.41 | 49.1% | 27 | 6 | 22.2% |
| pDAB111442 | IRDIG.586.42 | 48.5% | 32 | 7 | 21.9% |
| pDAB111443 | IRDIG.586.43 | 53.8% | 23 | 2 | 8.7% |
| Total | | — | 373 | 86 | 23% |
| pDAB109812 | ZmUbi1/PhiYFP | — | 6 | 2 | 33.3% |

| Plasmid | No. LC events (PCR) | % LC | No. HC events (PCR) | SpecR | % SpecR backbone |
|---|---|---|---|---|---|
| pDAB110839 | 33 | 91.7% | 3 | 7 | 19.4% |
| pDAB110842 | 35 | 83.3% | 7 | 3 | 7.1% |
| pDAB111434 | 25 | 80.6% | 6 | 4 | 12.9% |
| pDAB111435 | 34 | 91.9% | 3 | 9 | 24.3% |
| pDAB111436 | 15 | 78.9% | 4 | 10 | 52.6% |
| pDAB111437 | 23 | 62.2% | 9 | 12 | 32.4% |
| pDAB111438 | 25 | 83.3% | 5 | 2 | 6.7% |
| pDAB111439 | 23 | 69.7% | 10 | 3 | 9.1% |
| pDAB111440 | 21 | 80.8% | 5 | 12 | 46.2% |
| pDAB111441 | 22 | 81.5% | 5 | 6 | 22.2% |
| pDAB111442 | 22 | 68.8% | 3 | 6 | 18.8% |
| pDAB111443 | 20 | 87.0% | 3 | 9 | 39.1% |
| Total | 298 | 80% | 63 | 83 | 22% |
| pDAB109812 | 5 | 83.3% | 1 | 2 | 33.3% |

The various cry1F-containing backgrounds were compared to determine the statistical significance of the effect of DNA sequence on generation of single copy events. The number of events that contained a single copy of AAD-1, as measured by the hydrolysis probe assay, was compared as a percentage of the total number of events and using the JMP™ Statistical software, to complete a contingency analysis. The contingency analysis determined that the number of one copy events generated by the backgrounds pDAB111435, pDAB110839, pDAB111434, pDAB111438, pDAB111441, and pDAB111442 were statistically equal at the 0.05 level of significance, even though the percentage of one copy events ranged from 51.4% to 21.9%.

Figure 10:
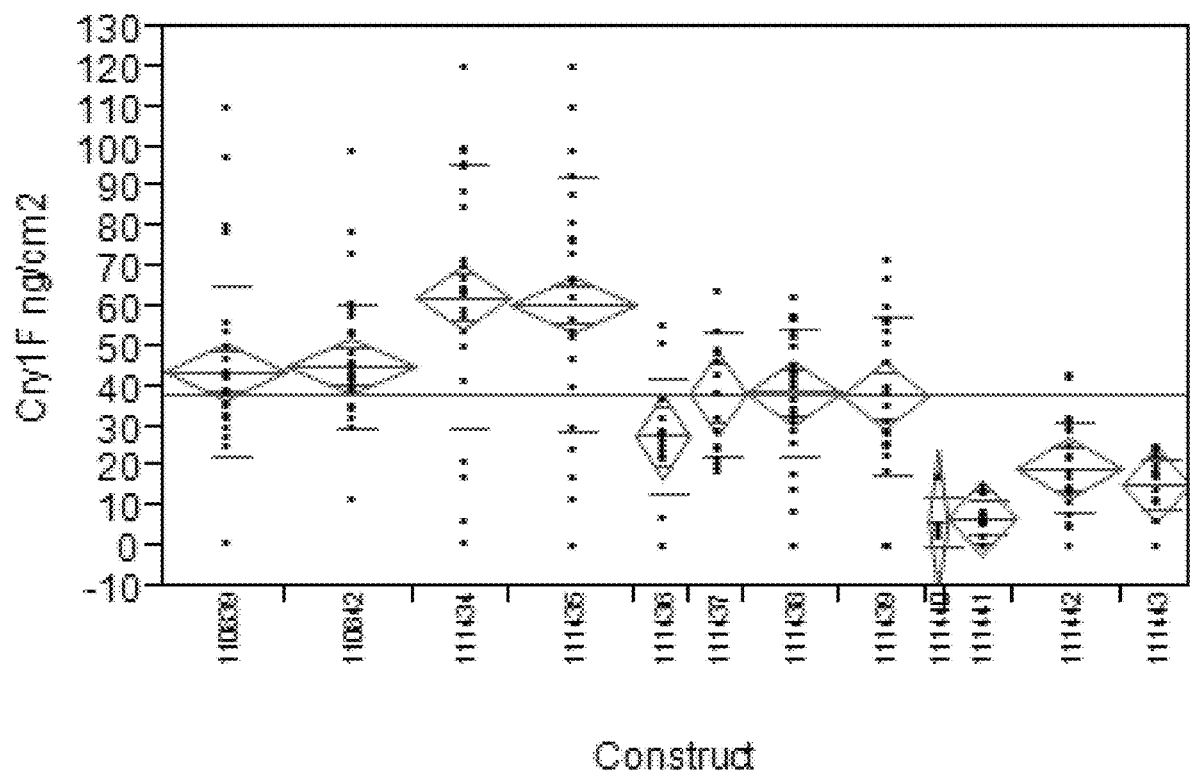
FIG. 10 includes a summary of the statistical analysis of $T_0$ events for each of the backgrounds using JMP statistical software. HERCULEX®, the product, was determined to express Cry1Fa at 60 ng/cm² under these greenhouse conditions. The average is the center line of the green diamond for each of the backgrounds. The line depicted directly below 40 ng/cm² is the grand mean for all of the events across all backgrounds.

Protein Analysis. All of the low copy events that passed the molecular analysis screen from each of the twelve backgrounds were evaluated for protein expression by a quantitative Cry1Fa ELISA assay. FIG. 10 depicts the average protein expression of the events from each of the twelve backgrounds. The level of Cry1Fa expression in HERCULEX® in the greenhouse was determined to be 60 ng/cm². Two of the backgrounds (pDAB111434 and pDAB111435) provided an average level of expression for all of the $T_0$ events that was equal to that of HERCULEX®, with several events expressing Cry1Fa at considerably higher levels. pDAB110839 and pDAB110842, backgrounds containing the HERCULEX® version of Cry1Fa and the HERCULEX® gene cassette respectively, provided average Cry1Fa expression levels of 43.8 ng/cm² and 45.1 ng/cm², respectively. The average levels of Cry1Fa expression for the $T_0$ events from all of the other backgrounds were lower than those found for pDAB110839 and pDAB110842, although specific events from pDAB111437, pDAB111438, and pDAB111439 were determined to be at or above the 60 ng/cm² level of expression. Table 18.

TABLE 8

ELISA determination of Cry1FA protein expression from the various backgrounds, ranging from 4 ng/cm² to 62.8 ng/cm².

| Background | Description | No. Events Tested | Avg. Expression (ng/cm²) |
|---|---|---|---|
| pDAB110839 | Cry1Fa HX gene | 33 | 43.8 |
| pDAB110842 | Cry1Fa HX cassette | 35 | 45.1 |
| pDAB111434 | IRDIG.586.34 | 25 | 62.6 |
| pDAB111435 | IRDIG.586.35 | 33 | 60.8 |
| pDAB111436 | IRDIG.586.36 | 16 | 30 |
| pDAB111437 | IRDIG.586.37 | 21 | 36.2 |
| pDAB111438 | IRDIG.586.38 | 25 | 38.6 |
| pDAB111439 | IRDIG.586.39 | 23 | 38 |
| pDAB111440 | IRDIG.586.40 | 21 | 4 |
| pDAB111441 | IRDIG.586.41 | 22 | 8.5 |
| pDAB111442 | IRDIG.586.42 | 29 | 19.1 |
| pDAB111443 | IRDIG.586.43 | 20 | 17 |
| Total | | 303 | 33.6 |

Figure 11:
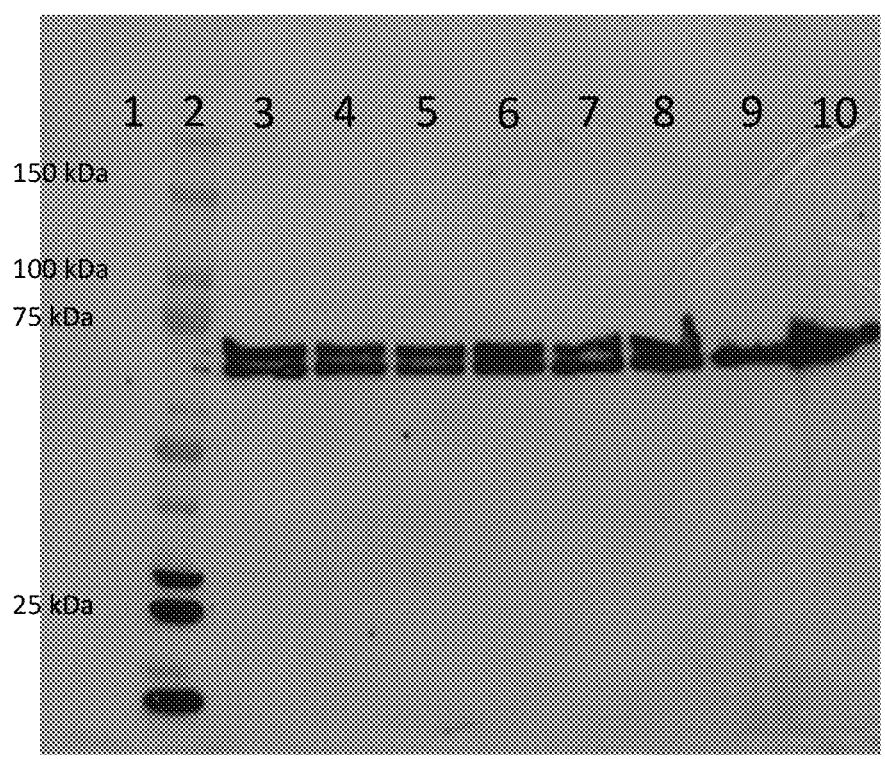
FIG. 11 includes the image of a Western Blot from maize leaf tissue harvested at the V5 stage of development. The contents of the lanes are as follows: Lane 1=negative control; lane 2=BioRad MWM, 20 µL; lane 3=111434[1]-010.001; lane 4=111434[1]-004.001; lane 5=111434[1]-013.001; lane 6=111435[1]-003.001; lane 7=111435[1]-006.001; lane 8=111435[1]-012.001; lane 9=bacterially purified Cry1Fa standard (2 ng); and lane 10=purified bacterial Cry1Fa standard (20 ng).

Western blots were completed on select events from each background to ensure that the protein was stable and of the correct size. Two distinct protein bands could be detected in events from most backgrounds, including the HERCULEX® control. The larger band (68 kDa) corresponds to the truncated Cry1Fa protein, and a smaller product (66 kDa) corresponds to the fully-processed active Cry1Fa core toxin. A representative Western blot consisting of samples from the pDAB111434 and pDAB111435 events is provided in FIG. 11.

Pollinations. High-expressing, single copy events, as determined by AAD-1 PCR analysis, which were also determined to be positive for the cry1Fa gene cassette, were considered for advancement to the $T_1$ generation. In most backgrounds, events containing the specR gene were omitted. However, in backgrounds pDAB111437, pDAB111442, and pDAB111443, there were not enough single copy events without specR, so a single event containing specR from each background was included. Plants from these events were not be included in any type of field testing, and were limited to testing in the greenhouse. Additionally, the pDAB111436 background only had a single 1 copy event available, and therefore four multi-copy events were selected for advancement. Otherwise, five events from each background were advanced to the $T_1$ generation, for cross-pollination with B104 donor events in reciprocal fashion.

Conclusions

Multiple DNA sequences were evaluated that would encode the truncated Cry1Fa protein, to identify a cry1Fa DNA sequence as an unexpectedly superior gene that will be utilized in an above-ground Lepidoptera control gene stack. Eleven different DNA sequences, encompassing various DNA design methodologies, were evaluated in maize at the $T_0$ generation. All eleven of the DNA sequences were combined with a binary plant transformation plasmid consisting of identical components for the expression of the Cry1Fa protein. Only the DNA sequence itself was varied.

Several parameters were affected by the cry1Fa DNA sequence. Protein expression ranged from a low of 4 ng/cm$^2$ for the average expression in the $T_0$ population (pDAB111440 background), to a high of 62.6 ng/cm$^2$ (pDAB111434 background), which represented a 15-fold increase in expression. Individual events were recorded to express the Cry1Fa protein as high as 120 ng/cm$^2$ in both the pDAB111434 and pDAB111435 backgrounds. Transformation frequency ranged from 4% (pDAB111436) to 23% (both pDAB110839 and pDAB111435), respectively. This difference in transformation frequency was statistically significant. Another factor in selection is the number of quality events, particularly events with a single copy of the cry1Fa gene cassette. Backgrounds with single copy events ranged from 5% (pDAB111436) to 51% (pDAB111435), respectively. This broad range of transformation frequency, DNA copy number (high quality events), and protein expression provided three distinct areas for the identification of a single background to advance for future stacking experiments.

The collective expression of Cry1Fa protein measured in the events from the pDAB111434 and pDAB111435 backgrounds was greater than all other backgrounds. Further, each of the two backgrounds had individual events with the highest levels of Cry1Fa protein expression. The DNA sequences from these two backgrounds are very similar; the DNA sequence from pDAB111434 was modified to reduce the number of G+C and A+T runs that were 6 bases and longer, to create pDAB111435. There are a total of 32 base differences between the cry1Fa genes of pDAB111434 and pDAB111435, and the DNA is 98.2% identical. The resulting protein expression is nearly identical (62.6 and 60.8 ng/cm$^2$), respectively. There is, however, a significant difference in transformation efficiency (5% and 23%), between these two backgrounds. Additionally, the difference in quality single copy event production, as detected by the hydrolysis probe assay, was statistically significant as well; 32.3% in pDAB111434 and 51.4% in pDAB111435.

The two backgrounds containing the HERCULEX® version of the cry1Fa gene, pDAB110839 (gene only) and pDAB110842 (gene cassette) each expressed Cry1Fa protein at relatively equal levels; 43.8 and 45.1 ng/cm$^2$, respectively. These two backgrounds had identical versions of the DNA sequence, but differed in the regulatory elements associated with the gene. The polylinker preceding the promoter in pDAB110842 includes a 24 base pair deletion, compared to pDAB110839. Different versions of the maize ubiquitin 1 promoter were used in each background, differing in sequence by 7 bases. The leader sequence that joins the promoter to the ATG translational start has a 5 base pair discrepancy, and 19 additional bases in the pDAB110839 background. Finally, the 3'UTR region for both gene cassettes are different; the pDAB110839 background has the *Zea mays* Per5 3'UTR, while pDAB110842 has the *A. tumefaciens* ORF25 3'UTR.

In additional to structural differences, the transformation efficiency and the percentage of single copy event detected in the two backgrounds also varied. The pDAB110839 background provided a statistically higher transformation efficiency (23%) and frequency of single copy events (30.6%), as compared to the pDAB110842 background (14% and 19%, respectively).

The remaining backgrounds each expressed Cry1Fa lower on average than the HERCULEX® controls. In the case of pDAB111436 and pDAB111437, elevated expression during the callus and young plantlet stages could have eliminated single copy high expressing events from the population, resulting in lower transformation rates and a population with reduced Cry1Fa expression. Some plantlets from these events were reported to have red discoloration in the leaves and stems with severe curling of the leaf and stem structures, ultimately resulting in poor plant health. The utilization of a weaker promoter than maize ubiquitin 1 in conjunction with these sequences may have been responsible for the lower overall expression, and pDAB111436 and pDAB111437 may be desirable DNA sequences with regards to protein expression.

Having an optimal DNA sequence for transgene expression in a particular host may be critical to achieving expression targets. Average protein expression from the different backgrounds varied from a low of 4 ng/cm$^2$ (observed in pDAB111440), to a high of 62.8 ng/cm$^2$ (measured in pDAB111434). The expression of single events ranged from 0 ng/cm$^2$, detected in all of the backgrounds, to a high of 120 ng/cm$^2$ in both pDAB111434 and pDAB111435 backgrounds, proving that integration into a poor location of the maize genome can result in non-expression regardless of the gene design. However, a gene designed for optimal expression in the host can be expressed at significantly higher levels as compared to a less optimal gene, if integration occurs at a location favorable for gene expression, as demonstrated by particular examples herein, ranging from 10 ng/cm$^2$ (pDAB111440) to 120 ng/cm$^2$ (pDAB11434 and pDAB111435).

What may be claimed is:

1. A system for expressing a heterologous polypeptide of interest in a cell of a maize plant, the system comprising:
    a reference nucleotide sequence encoding the polypeptide of interest from the genome of an organism other than the maize plant; and
    a synthetic polynucleotide comprising:
        a nucleotide sequence encoding the polypeptide of interest, wherein the nucleotide sequence has been codon-optimized to remove codons selected from the group consisting of TTA, CTA, GTA, CGT, AGT, and CGA from the reference nucleotide,
        wherein the synthetic polynucleotide nucleotide sequence encoding the polypeptide of interest comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, present in the same number and in the same location as in the reference nucleotide sequence,
        wherein the synthetic polynucleotide nucleotide sequence encoding the polypeptide of interest does not comprise any polyadenylation sequence selected from the group consisting of AATAAT, AACCAA, ATATAA, ATACTA, ATAAAA, ATGAAA, AAGCAT, ATTAAT, ATACAT, AAAATA, ATTAAA, AATTAA, AATACA, and CATAAA in a different number or location than in the reference nucleotide sequence, and wherein the synthetic polynucleotide nucleotide sequence encoding the polypeptide of interest does not comprise a polyadenylation sequence selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, TGTTTG, TTATAT, TGTAAT, AAATAA, AATTTT, TTTTTA, TAATTT, TTAATT, AAATTT, TTTGTT, ATTATT, ATTTTA, TTTAAT, and TTTTAA.

2. The system of claim 1, wherein the nucleotide sequence encoding the polypeptide of interest has been codon-optimized to remove from the reference nucleotide sequence all codons selected from the group consisting of TTA, CTA, GTA, CGT, AGT, and CGA.

3. The system of claim 1, wherein the polypeptide of interest is a protein selected from the group consisting of insecticidal proteins, herbicide tolerance proteins, stress tolerance-related proteins, and oil profile modification proteins.

4. The system of claim 1, wherein the polypeptide of interest is an insecticidal protein.

5. The system of claim 4, wherein the polypeptide of interest is Cry 1 Ab or Cry1Fa.

6. The system of claim 5, wherein the reference nucleotide sequence is SEQ ID NO:30.

7. The system of claim 5, wherein the reference nucleotide sequence is SEQ ID NO:31.

8. A transgenic maize plant comprising a synthetic polynucleotide comprising:
a nucleotide sequence encoding a polypeptide of interest, wherein the nucleotide sequence has been codon-optimized from a reference nucleotide sequence encoding the polypeptide of interest from the genome of an organism other than maize to remove codons selected from the group consisting of TTA, CTA, GTA, CGT, AGT, and CGA,
wherein the synthetic polynucleotide nucleotide sequence encoding the polypeptide of interest comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, present in the same number and in the same location as in the reference nucleotide sequence,
wherein the synthetic polynucleotide nucleotide sequence encoding the polypeptide of interest does not comprise any polyadenylation sequence selected from the group consisting of AATAAT, AACCAA, ATATAA, ATACTA, ATAAAA, ATGAAA, AAGCAT, ATTAAT, ATACAT, AAAATA, ATTAAA, AATTAA, AATACA, and CATAAA in a different number or location than in the reference nucleotide sequence, and
wherein the synthetic polynucleotide nucleotide sequence encoding a polypeptide of interest does not comprise a polyadenylation sequence selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, TGTTTG, TTATAT, TGTAAT, AAATAA, AATTTT, TTTTTA, TAATTT, TTAATT, AAATTT, TTTGTT, ATTATT, ATTTTA, TTTAAT, and TTTTAA.

9. The transgenic maize plant of claim 8, wherein the nucleotide sequence encoding the polypeptide of interest has been codon-optimized from the reference nucleotide sequence to remove all codons selected from the group consisting of TTA, CTA, GTA, CGT, AGT, and CGA.

10. The transgenic maize plant of claim 8, wherein the polypeptide of interest is a protein selected from the group consisting of insecticidal proteins, herbicide tolerance proteins, stress tolerance-related proteins, and oil profile modification proteins.

11. The transgenic maize plant of claim 8, wherein the polypeptide of interest is an insecticidal protein.

12. The transgenic maize plant of claim 11, wherein the polypeptide of interest is Cry1Ab or Cry1Fa.

13. The transgenic maize plant of claim 12, wherein the reference nucleotide sequence is SEQ ID NO:30.

14. The transgenic maize plant of claim 12, wherein the reference nucleotide sequence is SEQ ID NO:31.

15. A composition derived from the transgenic maize plant of claim 8, wherein the composition is a commodity product selected from the group consisting of meal, flour, protein concentrate, and oil.

16. A transgenic maize plant cell comprising a synthetic polynucleotide comprising:
a nucleotide sequence encoding a polypeptide of interest, wherein the nucleotide sequence has been codon-optimized from a reference nucleotide sequence encoding the polypeptide of interest from the genome of an organism other than maize to remove codons selected from the group consisting of TTA, CTA, GTA, CGT, AGT, and CGA,
wherein the synthetic polynucleotide nucleotide sequence encoding the polypeptide of interest comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, present in the same number and in the same location as in the reference nucleotide sequence,
wherein the synthetic polynucleotide nucleotide sequence encoding the polypeptide of interest does not comprise any polyadenylation sequence selected from the group consisting of AATAAT, AACCAA, ATATAA, ATACTA, ATAAAA, ATGAAA, AAGCAT, ATTAAT, ATACAT, AAAATA, ATTAAA, AATTAA, AATACA, and CATAAA in a different number or location than in the reference nucleotide sequence, and
wherein the synthetic polynucleotide nucleotide sequence encoding the polypeptide of interest does not comprise a polyadenylation sequence selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, TGTTTG, TTATAT, TGTAAT, AAATAA, AATTTT, TTTTTA, TAATTT, TTAATT, AAATTT, TTTGTT, ATTATT, ATTTTA, TTTAAT, and TTTTAA.

17. The transgenic maize plant cell of claim 16, wherein the nucleotide sequence encoding the polypeptide of interest has been codon-optimized from the reference nucleotide sequence to remove all codons selected from the group consisting of TTA, CTA, GTA, CGT, AGT, and CGA.

18. The transgenic maize plant cell of claim 16, wherein the polypeptide of interest is a protein selected from the group consisting of insecticidal proteins, herbicide tolerance proteins, stress tolerance-related proteins, and oil profile modification proteins.

19. The transgenic maize plant cell of claim 16, wherein the polypeptide of interest is an insecticidal protein.

20. The transgenic maize plant cell of claim 19, wherein the polypeptide of interest is Cry1Ab or Cry1Fa.

21. The transgenic maize plant cell of claim 20, wherein the reference nucleotide sequence is SEQ ID NO:30.

22. The transgenic maize plant cell of claim 20, wherein the reference nucleotide sequence is SEQ ID NO:31.

23. A plant material comprising the transgenic maize plant cell of claim 16, wherein the plant material comprises a detectable level of the synthetic polynucleotide.

24. A system for expressing a heterologous polypeptide of interest in a cell of a soybean plant, the system comprising:
 a reference nucleotide sequence encoding the polypeptide of interest from the genome of an organism other than the soybean plant; and
 a synthetic polynucleotide comprising:
  a nucleotide sequence encoding the polypeptide of interest, wherein the sequence has been codon-optimized to remove from the reference nucleotide sequence all codons selected from the group consisting of TTA, CTA, TCG, CCG, ACG, GCG, CGA, and CGG,
  wherein the synthetic polynucleotide nucleotide sequence encoding the polypeptide of interest comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, present in the same number and in the same location as in the reference nucleotide sequence,
  wherein the synthetic polynucleotide nucleotide sequence encoding the polypeptide of interest does not comprise any polyadenylation sequence selected from the group consisting of AATAAT, AACCAA, ATATAA, ATACTA, ATAAAA, ATGAAA, AAGCAT, ATTAAT, ATACAT, AAAATA, ATTAAA, AATTAA, AATACA, and CATAAA in a different number or location than in the reference nucleotide sequence, and
  wherein the synthetic polynucleotide nucleotide sequence encoding the polypeptide of interest does not comprise a polyadenylation sequence selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, GTTTTG, TTATAT, TGTAAT, AAATAA, AATTTT, TTTTTA, TAATTT, TTAATT, AAATTT, TTTGTT, ATTATT, ATTTTA, TTTAAT, and TTTTAA.

25. The system of claim 24, wherein the polypeptide of interest is a protein selected from the group consisting of insecticidal proteins, herbicide tolerance proteins, stress tolerance-related proteins, and oil profile modification proteins.

26. The system of claim 24, wherein the polypeptide of interest is an insecticidal protein.

27. The system of claim 26, wherein the polypeptide of interest is Cry1Ab or Cry1Fa.

28. The system of claim 27, wherein the reference nucleotide sequence is SEQ ID NO:30.

29. The system of claim 27, wherein the reference nucleotide sequence is SEQ ID NO:31.

30. A transgenic soybean plant comprising a synthetic polynucleotide comprising:
 a nucleotide sequence encoding a polypeptide of interest, wherein the nucleotide sequence has been codon-optimized from a reference nucleotide sequence encoding the polypeptide of interest from the genome of an organism other than soybean to remove all codons selected from the group consisting of TTA, CTA, TCG, CCG, ACG, GCG, CGA, and CGG,
 wherein the synthetic polynucleotide nucleotide sequence encoding the polypeptide of interest comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, present in the same number and in the same location as in the reference nucleotide sequence,
 wherein the synthetic polynucleotide nucleotide sequence encoding the polypeptide of interest does not comprise any polyadenylation sequence selected from the group consisting of AATAAT, AACCAA, ATATAA, ATACTA, ATAAAA, ATGAAA, AAGCAT, ATTAAT, ATACAT, AAAATA, ATTAAA, AATTAA, AATACA, and CATAAA in a different number or location than in the reference polynucleotide, and
 wherein the sequence of the synthetic polynucleotide does not comprise a polyadenylation sequence selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTT-TAT, ATATTT, TATTAT, GTTTTG, TTATAT, TGTAAT, AAATAA, AATTTT, TTTTTA, TAATTT, TTAATT, AAATTT, TTTGTT, ATTATT, ATTTTA, TTTAAT, and TTTTAA.

31. The transgenic soybean plant of claim 30, wherein the polypeptide of interest is a protein selected from the group consisting of insecticidal proteins, herbicide tolerance proteins, stress tolerance-related proteins, and oil profile modification proteins.

32. The transgenic soybean plant of claim 30, wherein the polypeptide of interest is an insecticidal protein.

33. The transgenic soybean plant of claim 32, wherein the polypeptide of interest is Cry1Ab or Cry1Fa.

34. The transgenic soybean plant of claim 33, wherein the reference nucleotide sequence is SEQ ID NO:30.

35. The transgenic soybean plant of claim 33, wherein the reference nucleotide sequence is SEQ ID NO:31.

36. A composition derived from the transgenic soybean plant of claim 30, wherein the composition is a commodity product selected from the group consisting of meal, flour, protein concentrate, and oil.

37. A transgenic soybean plant cell comprising a synthetic polynucleotide comprising:
 a nucleotide sequence encoding a polypeptide of interest, wherein the nucleotide sequence has been codon-optimized from a reference nucleotide sequence encoding the polypeptide of interest from the genome of an organism other than soybean to remove all codons selected from the group consisting of TTA, CTA, TCG, CCG, ACG, GCG, CGA, and CGG,
 wherein the synthetic polynucleotide nucleotide sequence encoding the polypeptide of interest comprises at least one polyadenylation sequence selected from the group consisting of AATAAA, AATAAT, AACCAA, ATATAA, AATCAA, ATACTA, ATAAAA, ATGAAA, AAGCAT, ATTAAT, ATACAT, AAAATA, ATTAAA, AATTAA, AATACA, and CATAAA, present in the same number and in the same location as in the reference nucleotide sequence, wherein the synthetic polynucleotide nucleotide sequence encoding the polypeptide of interest does not comprise any polyadenylation sequence selected from the group consisting of AATAAT, AACCAA, ATATAA, ATACTA, ATAAAA, ATGAAA, AAGCAT, ATTAAT, ATACAT, AAAATA, ATTAAA, AATTAA, AATACA, and CATAAA in a different number or location than in the reference nucleotide sequence, and wherein the synthetic polynucleotide nucleotide sequence encoding the polypeptide of interest does not comprise a polyadenylation sequence selected from the group consisting of ATATAT, TTGTTT, TTTTGT, TGTTTT, TATATA, TATTTT, TTTTTT, ATTTTT, TTATTT, TTTATT, TAATAA, ATTTAT, TATATT, TTTTAT, ATATTT, TATTAT, TGTTTG, TTATAT, TGTAAT, AAATAA, AATTTT, TTTTTA, TAATTT, TTAATT, AAATTT, TTTGTT, ATTATT, ATTTTA, TTTAAT, and TTTTAA.

38. The transgenic soybean plant cell of claim 37, wherein the polypeptide of interest is a protein selected from the group consisting of insecticidal proteins, herbicide tolerance proteins, stress tolerance-related proteins, and oil profile modification proteins.

39. The transgenic soybean plant cell of claim 37, wherein the polypeptide of interest is an insecticidal protein.

40. The transgenic soybean plant cell of claim 39, wherein the polypeptide of interest is Cry1Ab or Cry1Fa.

41. The transgenic soybean plant cell of claim 40, wherein the reference nucleotide sequence is SEQ ID NO:30.

42. The transgenic maize plant cell of claim 40, wherein the reference nucleotide sequence is SEQ ID NO:31.

43. A plant material comprising the transgenic soybean plant cell of claim 37, wherein the plant material comprises a detectable level of the synthetic polynucleotide.

* * * * *

SEQUENCE LISTING

<160> NUMBER OF SEQ ID NOS: 31

<210> SEQ ID NO 1
<211> LENGTH: 1860
<212> TYPE: DNA

<213> ORGANISM: Artificial Sequence
<220> FEATURE:
<223> OTHER INFORMATION: IRDIG.1471.2

<400> SEQUENCE: 1

```
atggataaca acccgaacat caacgagtgc atcccgtaca actgcctgag caacccggag    60
gtggaggtgc tgggcggcga gaggatcgag accggctaca ccccgatcga catcagcctg   120
tccctgaccc agttcctgct gtccgagttc gtgcctggcg ctggcttcgt gctgggactc   180
gtggatataa tctggggaat ctttggcccg tcccagtggg acgccttcct ggtgcagatc   240
gagcagctaa ttaaccaaag gatcgaggag ttcgcgagga accaagccat ttcgaggctg   300
gagggcctgt ccaacctgta ccaaatctac gcggagagct ccgcgagtg ggaggcggac   360
ccgaccaacc cggccctgag ggaggagatg aggatacagt tcaacgacat gaactccgcg   420
ctgaccaccg ccatcccgct gttcgccgtg cagaactacc aagtgccgct gctgtccgtg   480
tacgtgcaag ccgcgaacct gcacctgagc gtgctgaggg acgtgagcgt ctttggccag   540
aggtggggct tcgacgcggc gaccatcaac agcagataca acgacctgac cagactgatc   600
ggcaactaca ccgactacgc cgtgaggtgg tacaacaccg gcctggagag ggtgtggggc   660
ccggactcaa gggactgggt gagatacaat caattcagaa gggaattaac cctgaccgtg   720
ctggacatcg tggccctgtt cccgaactac gactcaagga gatacccgat cagaaccgtg   780
tcccaattaa ccagagaaat ctacaccaac ccggtgctgg agaacttcga cggcagcttc   840
agaggcagcg cccaaggcat cgagaggagc atcagatccc cgcacctgat ggacatcctg   900
aactccatca ccatctacac cgacgcgcac agaggctact actactggag cggccaccaa   960
ataatggcct ccccggtggg cttctccggc ccggagttca ccttcccgct gtacggcaca  1020
atgggcaacg cggccccgca gcagaggatc gtggcgcagc tgggccaagg cgtgtacaga  1080
accctcagct ccaccctgta cagaaggccg ttcaacatcg gcatcaataa tcaacagctg  1140
agcgtgctgg acggcaccga gttcgcatac ggcacctcct ccaacctgcc gagcgccgtg  1200
tacagaaagt ccggcaccgt ggactccctg gatgaaatcc cgccgcagaa caacaacgtg  1260
ccgccgaggc aaggcttcag ccacagactg agccacgtga gcatgttcag atccggcttc  1320
tcaaactcca gcgtgagcat catcagagcg ccgatgttca gctggataca taggagcgcg  1380
gagttcaata atataatccc cagctctcag atcacccaga tcccgctgac caagtccacc  1440
aacctgggct ccggcaccag cgtggtgaag ggaccgggct ttaccggcgg cgacatcctg  1500
aggaggacct ccccgggcca aatctccacc ctgagggtga acatcaccgc ccgctgagc  1560
cagagataca gagtgaggat cagatacgcg tccaccacca accttcagtt ccatacatcc  1620
atcgacggga ggccgattaa tcaaggcaac ttctccgcga ccatgtccag cggctccaac  1680
ctccagagcg gcagcttcag aaccgtgggc ttcaccaccc cgttcaactt ctcaaacggc  1740
agcagcgtgt tcaccctgag cgcccacgtg ttcaactccg gcaacgaggt gtacatcgac  1800
agaatcgagt tcgtgccggc agaagtgacc ttcgaggccg agtacgacct ggagaggtga  1860
```

<210> SEQ ID NO 2
<211> LENGTH: 1860
<212> TYPE: DNA
<213> ORGANISM: Artificial Sequence
<220> FEATURE:
<223> OTHER INFORMATION: IRDIG.1471.3

<400> SEQUENCE: 2

```
atggacaaca accctaacat caatgagtgc ataccataca actgtcttag caacccagaa    60
```

```
gttgaggttc tgggtgggga gaggatagag actggataca ctccaataga catttcgctg    120
tcactgacgc aattccttct gtctgagttc gttcctggtg ctggattcgt gctgggcttg    180
gtggatataa tttggggaat ctttggaccg tcccagtggg atgcctttct tgttcagatt    240
gagcagctaa ttaaccaaag aattgaggag tttgcacgca accaagccat atccagactt    300
gaaggccttt cgaacttgta tcaaatctac gcagagagct tcagagagtg ggaggcagac    360
ccgacgaatc cagccctcag agaggagatg aggattcagt tcaacgacat gaactcagca    420
ctgactactg ccattcccct ctttgccgtc cagaactatc aagtgccact gctgtccgtc    480
tacgttcaag cagcgaatct gcacctcagc gtcttgagag acgtctcggt ctttggccag    540
cgctggggtt ttgatgcagc gacgatcaat agcagataca atgacctcac aaggctgatt    600
ggaaactaca ccgattacgc agttcgctgg tacaatacgg gtctcgaacg ggtctgggga    660
cccgactcac gcgactgggt cagatacaat caattcagac gcgaattaac tttgaccgtt    720
ctggacatag tcgcactctt tccgaactac gacagcagaa gatatccgat taggacggtt    780
tcccaattaa ccagagaaat ctataccaat cccgtgctcg aaaactttga cggcagcttt    840
aggggaagcg ctcaaggcat tgagaggagc atcagatccc cacatctcat ggacattctg    900
aactcaatca cgatctacac tgatgcacat aggggttact actattggag cggtcatcaa    960
ataatggcct cgccagtggg gttttcgggt ccggagttta cattcccact gtacgggaca   1020
atgggaaatg cagcaccgca acagcggatc gttgctcagc tgggtcaagg ggtgtacaga   1080
acgctctcat cgacgctgta tcggagaccc ttcaacatag gcatcaataa tcaacaactc   1140
tcagtcttgg acggcaccga gttcgcgtat gggacatcct ccaacctccc gtctgccgtg   1200
tatcgcaagt ccggaacagt cgattcgctg gatgaaattc ctccacagaa caacaacgtg   1260
cctccaagac aaggcttctc tcacagattg agccatgtga gcatgttccg ctctggcttc   1320
tccaactcct cagtgtcgat cattagggca ccgatgttct cttggataca tcggagcgca   1380
gagttcaata atataatccc gtcaagccag atcacgcaga tcccactgac caagtccacc   1440
aatctcggct ctgggacaag cgttgtgaag ggtcctggct tcactggtgg ggatatcctg   1500
cggaggactt ctcctggcca gatttcaacc ctcagagtca acatcaccgc accccttca    1560 cagcgctatc gggttcgcat acgctacgct tccacgacca atctgcaatt ccatacatcc   1620
atcgacggga ggcctattaa tcaaggcaac ttctcagcga ctatgtcctc gggttctaac   1680
cttcagtctg gcagcttcag aacggtgggg ttcaccactc cattcaactt ctcgaacggg   1740
tcaagcgtgt tcaccttgag cgctcacgtg ttcaattccg gaaacgaagt gtacatcgac   1800
cgcatagagt tcgtgccagc agaagttaca ttcgaagccg agtacgatct tgagaggtga   1860
```

<210> SEQ ID NO 3
<211> LENGTH: 1860
<212> TYPE: DNA
<213> ORGANISM: Artificial Sequence
<220> FEATURE:
<223> OTHER INFORMATION: IRDIG.1471.4

<400> SEQUENCE: 3

```
atggataaca acccgaacat caatgagtgc atcccgtata actgtctcag taaccctgaa     60
gtggaggtct taggtggcga acgcatcgaa actggttaca ccccaatcga cattagcttg    120
tcgttgacgc agttcctctt gtccgagttc gtgcccggtg cgggtttcgt gctgggcta     180 gttgatataa tctggggaat ctttggtccc tctcagtggg acgcctttct tgtgcaaatt    240
```

-continued

```
gagcagctaa ttaaccaaag aatagaagag ttcgcgagga accaagccat ttccagactg    300
gagggactaa gcaaccttta tcaaatctac gcggagtctt ttagggagtg ggaggcagat    360
cctacgaacc cggcactgcg cgaagagatg cgtattcagt tcaacgacat gaacagtgcc    420
cttacaaccg ctattcccct tttcgcagtt caaaattacc aagttcccct tctctcagtg    480
tacgttcaag ccgcaaattt acacctaagc gttctccgcg atgtgtcagt gttcggccag    540
aggtggggat ttgatgccgc cactatcaat agtcgttata atgatctgac gaggcttatc    600
ggcaactata ccgactatgc tgtccgctgg tacaatacgg gattagagcg ggtctggggt    660
ccggattccc gagactgggt gcgctacaat caattccgcc gcgaattaac cctcactgtc    720
ctcgacatcg tggcgctgtt cccgaactac gacagtagga gatacccaat ccgcacagtt    780
tcccaattaa cgcgggaaat ttacaccaac ccagtcctgg agaattttga cgggagcttc    840
cgaggctcgg ctcaaggcat agaacgcagc attaggtcgc cacacttgat ggatatcctt    900
aacagcatca ccatctacac ggatgcccat agggggttact actactgtc ggggcatcaa    960 ataatggctt ctcctgtcgg gttttcgggg ccagagttca ccttcccgct ctacggcact   1020
atgggaaatg ccgcgccaca caacgtatc gtcgctcaac taggtcaagg cgtgtaccgg   1080
acactgtcgt ccactctcta tcggcggcct ttcaatatag ggatcaataa tcaacagttg   1140
tctgtgctgg acgggacaga gtttgcttac ggaacctcaa gcaacttgcc atccgctgta   1200
tacagaaaaa gcggcacggt ggactcgctg gatgaaatcc cgccccagaa taacaacgtg   1260
ccccctcggc aaggcttcag tcatcgactg agccacgtta gcatgttccg ttcgggcttc   1320
agcaactcct ccgtaagtat cataagagca cctatgttca gctggataca tcgttccgcc   1380
gagttcaata atataattcc ctcctctcaa atcacacaga tccctctgac aaagtctact   1440
aatcttggct ctgggacttc tgtcgttaag gggcctggct ttacgggcgg cgatattctg   1500
cggagaactt cacctggcca gatttccacc ctgcgcgtga atatcaccgc gccattgtca   1560
caacgttacc gcgtgcggat tcgctacgct tctaccacaa acctccagtt ccatacatct   1620
attgacggca gacccattaa tcaagggaat ttctccgcca cgatgtcgtc cggctccaat   1680
ctccagtccg gaagtttccg caccgtaggt tttactaccc cgttcaactt ttcaaacggc   1740
tcaagtgtgt ttacgctgtc cgctcatgtg ttcaactctg gcaatgaggt ttacatcgac   1800
cggattgagt tcgtcccggc agaagtcacc ttcgaagccg agtacgatct tgagaggtga   1860
```

<210> SEQ ID NO 4
<211> LENGTH: 1818
<212> TYPE: DNA
<213> ORGANISM: Artificial Sequence
<220> FEATURE:
<223> OTHER INFORMATION: IRDIG.586.34

<400> SEQUENCE: 4

```
atggagaata atatccagaa tcaatgcgtg ccgtacaact gcctgaataa tccggaggtg     60
gagatattaa acgaggagag gagcaccggg aggctgccgc tggacatctc cctgtccctg    120
acccgcttcc tgctgtccga gttcgtcccg ggcgtgggcg tggcgttcgg cctgttcgac    180
ctgatctggg gcttcatcac cccgagcgac tggagcctgt tcctgcttca gatcgagcag    240
ctgatcgagc agaggatcga gaccctggag aggaaccgcg cgatcaccac cctgagggc    300 ctggcggaca gctatgaaat ctacatcgag gcgctgaggg agtgggaggc caacccgaat    360
aatgctcaat taagggagga cgtgaggata cgcttcgcga atacagacga cgcgctgatc    420
accgcaatca ataatttcac cctgacctcc ttcgagatcc cgctgctgag cgtgtacgtc    480
```

```
caagcggcga acctgcacct gtccctgctg agggacgccg tgagctttgg ccaaggctgg      540
ggcctggaca tcgcgaccgt gaataatcac tacaacagat taatcaacct gatccaccgc      600
tacaccaagc actgcctgga cacctacaat caaggcctgg agaacctgag gggcaccaac      660
acccgccagt gggcgaggtt caaccagttt aggagggacc tgaccctgac cgtgctggac      720
atcgtggccc tgttcccgaa ctacgacgtg aggacctacc cgatccagac cagctcccaa      780
ttaacccgcg aaatctacac ctccagcgtg atcgaggaca gcccggtgtc cgcgaacatc      840
ccgaacggct tcaaccgcgc ggagttcggc gtgaggccgc cgcacctgat ggacttcatg      900
aacagcctgt tcgtgaccgc cgagaccgtg aggtcccaga ccgtgtgggg aggccacctg      960
gtgtcctcac gcaacaccgc cggcaaccgc atcaacttcc cgtcctacgg cgtgttcaac     1020
ccgggcggcg ccatctggat cgccgacgag gacccgaggc cgttctaccg caccctgagc     1080
gacccggtgt tcgtgagggg cggctttggc aacccgcact acgtgctggg cctgaggggc     1140
gtggccttcc agcagaccgg caccaaccac acccgcacct tccgcaacag cggcaccatc     1200
gacagcctgg atgaaatccc gccgcaagac aactccggcg ccccgtggaa cgactacagc     1260
cacgtattaa accacgtgac cttcgtgagg tggccggggcg aaatctccgg cagcgacagc     1320
tggagggcac cgatgttctc ctggacccat cggtccgcga ccccgaccaa tacaatcgac     1380
ccggagagga tcacccagat cccgctggtg aaggcgcaca cccttcagag cggcaccacc     1440
gtggtgaggg gaccgggctt caccggaggc gacatcctga ggaggacctc gggaggaccg     1500
ttcgcgtata ctatcgtgaa tataaacggc cagctgccgc agcgctaccg ggcacgcatc     1560
cgctacgcca gcaccaccaa cctgaggatc tacgtgaccg tggcggggga gaggatcttc     1620
gcgggccagt tcaacaagac aatggacacc ggagacccgc tgaccttcca gagcttctcc     1680
tacgccacca ttaatacagc gttcaccttc ccgatgagcc agtcctcatt caccgtgggc     1740
gccgacacct tctccagcgg caacgaggtg tacatcgacc gcttcgagct gatcccagtg     1800
accgccaccc tcgagtga                                                   1818
```

<210> SEQ ID NO 5
<211> LENGTH: 1818
<212> TYPE: DNA
<213> ORGANISM: Artificial Sequence
<220> FEATURE:
<223> OTHER INFORMATION: IRDIG.586.35

<400> SEQUENCE: 5

```
atggagaata tatccagaa tcaatgcgtg ccgtacaact gcctgaataa tccggaggtg       60
gagatattaa cgaggagag gagcaccggg aggctgccgc tggacatctc cctgtccctg      120
acccgcttcc tgctgtccga gttcgtccct ggcgtgggcg tggcgttcgg cctgttcgac      180
ctgatctggg gcttcatcac cccgagcgac tggagcctgt tcctgcttca gatcgagcag      240
ctgatcgagc agaggatcga gaccctggag aggaacagag cgatcaccac cctgagaggc      300
ctggcggaca gctatgaaat ctacatcgag gcgctgaggg agtgggaggc caacccgaat      360
aatgctcaat aagggagga cgtgaggata cgcttcgcga atacagacga cgcgctgatc      420
accgcaatca ataatttcac cctgacctcc ttcgagatcc cgctgctgag cgtgtacgtc      480
caagctgcga acctgcacct gtccctgctg agggacgccg tgagctttgg ccaaggctgg      540
ggtctggaca tcgcgaccgt gaataatcac tacaacagat taatcaacct gatccaccgc      600
tacaccaagc actgcctgga cacctacaat caaggcctgg agaacctgag gggcaccaac      660
```

-continued

```
acaaggcagt gggcgaggtt caaccagttt aggagggacc tgaccctgac cgtgctggac      720
atcgtggccc tgttcccgaa ctacgacgtg aggacctacc cgatccagac cagctcccaa      780
ttaacacgcg aaatctacac ctccagcgtg atcgaggact ctccggtgtc cgcgaacatc      840
ccgaacggct tcaacagagc ggagttcggc gtgaggccac cgcacctgat ggacttcatg      900
aacagcctgt tcgtgactgc cgagaccgtg aggtcccaga ccgtgtgggg aggccacctg      960
gtgtcctcac gcaacaccgc tggcaaccgc atcaacttcc cgtcctacgg cgtgttcaac     1020
cctggtggag ccatctggat cgccgacgag gacccgaggc cgttctaccg caccctgagc     1080
gacccggtgt tcgtgagggg tggctttggc aacccgcact acgtgctggg cctgagaggc     1140
gtggccttcc agcagaccgg caccaaccac acccgcacct ccgcaacag cggcaccatc      1200 gacagcctgg atgaaatccc accgcaagac aactccggtg ctccgtggaa cgactacagc     1260
cacgtattaa accacgtgac cttcgtgagg tggcctggcg aaatctccgg cagcgacagc     1320
tggagggcac cgatgttctc ctggacccat cggtccgcga ccccgaccaa tacaatcgac     1380
ccggagagga tcacccagat cccgctggtg aaggcgcaca cccttcagag cggcaccacc     1440
gtggtgaggg gacctggctt caccggaggc gacatcctga ggaggacctc gggaggaccg     1500
ttcgcgtata ctatcgtgaa tataaacggc cagctgccgc agcgctacag agcacgcatc     1560
cgctacgcca gcaccaccaa cctgaggatc tacgtgaccg tggctgggga gaggatcttc     1620
gctggccagt caacaagac aatggacacc ggagacccgc tgaccttcca gagcttctcc     1680
tacgccacca ttaatacagc gttcaccttc ccgatgagcc agtcctcatt caccgtgggt     1740
gccgacacct tctccagcgg caacgaggtg tacatcgacc gcttcgagct gatcccagtg     1800
accgccaccc tcgagtga                                                  1818
```

<210> SEQ ID NO 6
<211> LENGTH: 1818
<212> TYPE: DNA
<213> ORGANISM: Artificial Sequence
<220> FEATURE:
<223> OTHER INFORMATION: IRDIG586.36

<400> SEQUENCE: 6

```
atggagaata atatccagaa tcaatgcgtg ccgtacaact gcctcaataa tccggaggtg       60
gagatattaa acgaggagcg cagcaccggc cgcctcccgc tcgacatctc cctctcccctc     120 acccgcttcc tcctctccga gttcgtgccg ggcgtgggcg tggccttcgg cctcttcgac      180
ctcatctggg gcttcatcac cccgtccgac tggtccctct cctcctcca gatcgagcag      240 ctcatcgagc agcgcatcga gaccctcgag cgcaaccgcg ccatcaccac cctccgcggc      300
ctcgccgact cctatgaaat ctacatcgag gccctccgcg agtgggaggc caacccgaat      360 aatgccaat taagggagga cgtgcgcatc cgcttcgcca atacagacga cgccctcatc      420
accgcaatca ataatttcac cctcacctcc ttcgagatcc cgctcctctc cgtgtacgtg      480
caggccgcca acctccacct ctccctcctc cgcgacgccg tgtccttcgg ccagggctgg      540
ggcctcgaca tcgccaccgt gaataatcac tacaacagat taatcaacct catccaccgc      600
tacaccaagc actgcctcga cacctacaat caaggcctcg agaacctccg cggcaccaac      660
acccgccagt gggcccgctt caaccagttc cgccgcgacc tcaccctcac cgtgctcgac      720
atcgtggccc tcttcccgaa ctacgacgtg cgcacctacc cgatccagac ctcctcccaa      780
ttaacccgcg agatctacac ctcctccgtg atcgaggact cccccggtgtc cgccaacatc     840 ccgaacggct tcaaccgcgc cgagttcggc gtgcgcccgc cgcacctcat ggacttcatg      900
```

```
aactccctct tcgtgaccgc cgagaccgtg cgctcccaga ccgtgtgggg cggccacctc    960
gtgtcctccc gcaacaccgc cggcaaccgc atcaacttcc cgtcctacgg cgtgttcaac   1020
ccgggcggcg ccatctggat cgccgacgag gacccgcgcc cgttctaccg caccctctcc   1080
gacccggtgt tcgtgcgcgg cggcttcggc aacccgcact acgtgctcgg cctccgcggc   1140
gtggccttcc agcagaccgg caccaaccac acccgcacct tccgcaactc cggcaccatc   1200
gactccctcg atgaaatccc gccgcaggac aactccggcg ccccgtggaa cgactactcc   1260
cacgtattaa accacgtgac cttcgtgcgc tggccgggcg agatctccgg ctccgactcc   1320
tggcgcgcgc cgatgttctc ctggacccac cgctccgcca ccccgaccaa tacaatcgac   1380
ccggagcgca tcacccagat cccgctcgtg aaggcccaca ccctccagtc cggcaccacc   1440
gtggtgcgcg gccgggcttc accggcggc gacatcctcc gccgcacctc cggcggcccg   1500
ttcgcctata ctatcgtgaa tataaacggc cagctcccgc agaggtacag ggcccgcatc   1560
cgctacgcct ccaccaccaa cctccgcatc tacgtgaccg tggccggcga gcgcatcttc   1620
gccggccagt tcaacaagac gatggacacc ggcgacccgc tcaccttcca gtccttctcc   1680
tacgccacca ttaatacagc cttcaccttc ccgatgtccc agtcctcctt caccgtgggc   1740
gccgacacct tctcctcagg caacgaggtc tacatcgacc gcttcgagct gatcccgtg    1800 accgccaccc tcgagtga                                                 1818

<210> SEQ ID NO 7
<211> LENGTH: 1818
<212> TYPE: DNA
<213> ORGANISM: Artificial Sequence
<220> FEATURE:
<223> OTHER INFORMATION: IRDIG.586.37

<400> SEQUENCE: 7
atggagaata atatccagaa tcaatgcgtg ccgtacaact gcctcaataa tccggaggtg     60
gagatattaa acgaggagcg cagcaccgga cgcctcccgc tcgacatctc cctctccctc    120
acccgcttcc tcctctccga gttcgtgcct ggcgtgggcg tggctttcgg cctcttcgac    180
ctcatctggg gcttcatcac cccgtccgac tggtccctct tcctcctcca gatcgagcag    240
ctcatcgagc agcgcatcga gaccctggag cgcaacagag ccatcaccac cctcagaggc    300
ctcgccgact cctatgaaat ctacatcgag gccctccgcg agtgggaggc caacccgaat    360
aatgcccaat aagggagga cgtccgcatc cgcttcgcca atacagacga cgccctcatc    420
accgcaatca ataatttcac cctcaccctcc ttcgagatcc cgctcctctc cgtgtacgtg    480
caagcagcca acctccacct ctccctcctc cgcgacgccg tgtcgttcgg ccaaggctgg    540
ggtctcgaca tcgccaccgt gaataatcac tacaacagat taatcaacct catccaccgc    600
tacaccaagc actgcctcga cacctacaat caaggcctgg agaacctcag aggcaccaac    660
acacgccagt gggcacgctt caaccagttc cgcagagacc tcaccctcac cgtgctcgac    720
atcgtggccc tcttcccgaa ctacgacgtc cgcacctacc cgatccagac ctcctcccaa    780
ttaacacgcg aaatctacac ctcctccgtg atcgaggact ctccggtgtc cgccaacatc    840
ccgaacggct tcaacagagc cgagttcggc gtgaggccac cgcacctcat ggacttcatg    900
aactccctct tcgtgacagc cgagaccgtg cgctcccaga ccgtgtgggg tggccacctc    960
gtgtcctcca gaaacaccgc tggcaaccgc atcaacttcc cgtcctacgg cgtgttcaac   1020
cctggcggag ccatctggat cgccgacgag gacccgaggc cgttctaccg cacgctctcc   1080
```

```
gacccggtgt tcgtgagggg agggttcggc aacccgcact acgtgctcgg cctcagaggc   1140
gtggccttcc agcagaccgg caccaaccac acccgcacct tccgcaactc cggcaccatc   1200
gactccctcg atgaaatccc accgcaagac aactccggag caccgtggaa cgactactcc   1260
cacgtattaa accacgtgac cttcgtgcgc tggcctggcg aaatctccgg ctccgactcc   1320
tggagggcac cgatgttctc ctggacccac cgctccgcca ccccgaccaa tacaatcgac   1380
ccggagcgca tcacccagat cccgctcgtg aaggcccaca ccctccagtc cggcaccacc   1440
gtggtgagag ccctggctt cactggtggc gacatcctca gacgcacctc tggcggaccg      1500
ttcgcctata ctatcgtgaa atataaacgg cagctcccgc agagatacag agcacgcatc   1560
cgctacgcct ccaccaccaa cctccgcatc tacgtgaccg tggctgggga gcgcatcttc   1620
gctggccagt tcaacaagac gatggacact ggcgacccgc tcaccttcca gtccttctcc   1680
tacgccacca ttaatacagc cttcaccttc ccgatgtccc agtcctcctt caccgtggga   1740
gccgacacct tctcatccgg caacgaggtc tacatcgacc gcttcgagct gatccccgtg   1800
accgccaccc tcgagtga                                                  1818

<210> SEQ ID NO 8
<211> LENGTH: 1818
<212> TYPE: DNA
<213> ORGANISM: Artificial Sequence
<220> FEATURE:
<223> OTHER INFORMATION: IRDIG.586.38

<400> SEQUENCE: 8
atggagaata tatacagaa tcaatgcgtc ccctacaact gcctcaataa tcctgaagta      60
gagatattaa acgaagagag gtcgactggc agattgccgt tagacatctc cctgtccctt    120
acacgtttcc tgttgtctga gtttgttcca ggtgtgggag ttgcgtttgg cctcttcgac    180
ctcatctggg gcttcatcac tccatctgat ggagcctct tcttctcca gattgaacag      240 ttgattgaac aaaggattga gaccttggaa aggaatcggg ccatcactac ccttcgtggc    300
ttagcagaca gctatgaaat ctacattgaa gcactaagag agtgggaagc caatcctaat    360
aatgcccaat taagaagaa tgtgcgtata cgctttgcta atacagatga tgcttttgatc    420 acagcaatca ataatttcac ccttaccagc ttcgagatcc ctcttctctc ggtctatgtt    480
caagctgcta acctgcactt gtcactactg cgcgacgctg tgtcgtttgg gcaaggttgg    540
ggactggaca tagctactgt caataatcac tacaacagat taatcaatct gattcatcga    600
tacacgaaac attgtttgga tacctacaat caaggattgg agaacctgag aggtactaac    660
actcgccaat gggccaggtt caatcagttc aggagagacc ttacacttac tgtgttagac    720
atagttgctc tctttccgaa ctacgatgtt cgtacctatc cgattcaaac gtcatcccaa    780
ttaacaaggg agatctacac cagttcagtc attgaagact ctccagtttc tgcgaacata    840
cccaatggtt tcaacagggc tgagtttgga gtcagaccac cccatctcat ggacttcatg    900 aactcttttgt ttgtgactgc agagactgtt agatcccaaa ctgtgtgggg aggacactta    960
gttagctcac gcaacacggc tggcaatcgt atcaactttc ctagttacgg ggtcttcaat   1020 cccggggggcg ccatctggat tgcagatgaa gatccacgtc cttctatcg gaccttgtca   1080 gatcctgtct tcgtccgagg aggctttggc aatcctcact atgtactcgg tcttagggga   1140 gtggccttc aacaaactgg tacgaatcac acccgcacat tcaggaactc cgggaccatt    1200
gactctctag atgaaatacc acctcaagac aacagcggcg cacctgga tgactactcc   1260 catgtattaa atcatgttac ctttgtgcgc tggccaggtg agatctcagg ttccgactca   1320
```

```
tggagagcac caatgttctc ttggacgcat cgtagcgcta cccccacaaa tacaattgat    1380
ccagagagaa tcactcagat tcccttggtg aaggcacaca cacttcagtc aggaactaca    1440
gttgtaagag ggccggggtt cacgggagga gacattcttc gacgcactag tggaggacca    1500
ttcgcgtata ctattgtcaa tataaatggg caacttcccc aaaggtatcg tgccaggata    1560
cgctatgcct ctactaccaa tctaagaatc tacgttacgg ttgcaggtga acggatcttt    1620
gctggtcagt tcaacaagac aatggatacc ggtgatccac ttacattcca atctttctcc    1680
tacgccacga ttaatacagc gttcaccttt ccaatgagcc agagcagttt cacagtaggt    1740
gctgatacct tcagttcagg caacgaagtg tacattgaca ggtttgagtt gattccagtt    1800
actgccacac tcgagtga                                                  1818
```

<210> SEQ ID NO 9
<211> LENGTH: 1818
<212> TYPE: DNA
<213> ORGANISM: Artificial Sequence
<220> FEATURE:
<223> OTHER INFORMATION: IRDIG.586.39

<400> SEQUENCE: 9

```
atggagaata atatacagaa tcaatgcgtc ccctacaact gcctcaataa tcctgaagtc      60
gagatattaa acgaagagag gtccactggc agattgccgt tggacatctc cctgtccctt     120
acacgcttcc tgttgtctga gtttgttcct ggtgtgggag ttgcgtttgg cctcttcgac     180
ctcatctggg gattcatcac tccatctgat tggagcctct tcttctccca gattgaacag     240
ttgattgaac aaaggattga gaccttggaa aggaatagac catcactac ccttagaggc     300 ctcgcagaca gctatgaaat ctacattgaa gcactcagag agtgggaagc caatcccaat     360
aatgcccaat taagagaaga tgtgcggata cgctttgcta atacagatga tgctttgatc     420
acagcaatca ataatttcac ccttaccagc ttcgagatcc ctcttctctc ggtctatgtt     480
caagctgcta acctgcactt gtcactcctg cgcgacgctg tgtcgtttgg gcaaggttgg     540
ggactggaca tagctactgt caataatcac tacaacagat taatcaatct gattcatcgc     600
tacacgaaac actgcttgga tacctacaat caaggattgg agaacctgag aggcactaac     660
actcgccaat gggcgaggtt caatcagttt aggagagacc ttacacttac tgtgctcgac     720
atagttgctc tctttccgaa ctacgatgtt cgcacctatc cgattcaaac gtcatcccaa     780
ttaacaaggg agatttacac cagctcagtc attgaggact ctccagtttc tgcgaacata     840
cccaatggtt tcaacagagc tgagtttgga gtcagaccac cccatctcat ggacttcatg     900
aactctctct tgtgactgc cgagactgtt agatcccaaa ctgtgtgggg aggacacctc     960
gttagctcac gcaacacggc tggcaatcgc atcaacttc cttcctacgg ggtgttcaat    1020
cctggaggtg ccatctggat tgcagatgaa gatccacgcc ctttctatcg gaccttgtca    1080
gatcctgtgt tcgtcagagg aggctttggc aatcctcact atgtcctcgg tcttagggga    1140
gtggcctttc aacaaactgg cacgaatcac acccgcacat tccgcaactc cgggaccatt    1200
gactcccttg atgaaatacc acctcaagac aactccggtg cgccttggaa tgactactcc    1260
catgtattaa atcatgttac ctttgtgcgc tggcctggtg aaatctccgg ttccgactca    1320
tggagagcac caatgttctc ttggacgcat cgcagcgcta cccccacaaa tacaatcgat    1380
ccagagagaa tcactcagat tcccttggtg aaggcacaca cacttcagtc gggaactaca    1440
gttgtcagag gacctgggtt cacgggagga gacattctta ggcgcaccag cggaggacca    1500
```

| | |
|---|---|
| ttcgcgtata ctattgtcaa tataaatggg caacttcccc aacgctatag agcgaggata | 1560 |
| cgctatgcct ctactaccaa tcttagaatc tacgttacgg tcgctggtga acggatcttt | 1620 |
| gctggtcagt tcaacaagac aatggatact ggtgatccac ttacattcca atctttctcc | 1680 |
| tacgccacga ttaatacagc gttcaccttt ccaatgagcc agagcagctt cacagtcggt | 1740 |
| gctgatacct tctcatctgg caacgaagtg tacattgacc gctttgagtt gattccagtt | 1800 |
| actgccacac tggagtaa | 1818 |

<210> SEQ ID NO 10
<211> LENGTH: 1818
<212> TYPE: DNA
<213> ORGANISM: Artificial Sequence
<220> FEATURE:
<223> OTHER INFORMATION: IRDIG.586.40

<400> SEQUENCE: 10

| | |
|---|---|
| atggagaata atatccagaa tcaatgcgtg ccttacaatt gtctcaataa tcccgaggtg | 60 |
| gagatattaa acgaggagag atccactggc agactgccac tcgacatatc cttgtccctt | 120 |
| acccgttttcc ttttgagcga atttgttcct ggtgtgggag tggctttcgg actgttcgat | 180 |
| ctgatatggg gctttatcac tccttctgat tggagcctct tccttctcca gattgagcaa | 240 |
| ttgattgagc agagaataga aaccttggaa aggaaccgtg caatcacgac cttgcgcggt | 300 |
| ctcgccgata gctatgaaat ctacattgaa gcactgaggg agtgggaggc caaccccaat | 360 |
| aatgctcaat taagggaaga tgtgcgtatt cgttttgcta atacagacga cgctctcatc | 420 |
| acagcaatca ataatttcac acttacatcc tttgaaatcc cgcttttgag cgtgtacgtt | 480 |
| caagccgcca atctccacct ctcacttctg agggacgctg tctcctttgg gcaaggttgg | 540 |
| ggactggata tcgctactgt gaataatcac tacaatagat taatcaacct gattcataga | 600 |
| tatacgaagc actgcttgga cacatacaat caaggactgg agaaccttag gggaactaac | 660 |
| actaggcagt gggcaaggtt caaccagttc agacgtgatc tcacacttac tgtgctggat | 720 |
| atcgttgctc tctttccgaa ctacgatgtt cgcacctacc caatccagac gtcatcccaa | 780 |
| ttaacaaggg aaatctacac ctcctcagtg attgaggact ctcccgtttc tgctaacata | 840 |
| cctaacggct tcaaccgcgc cgagttcgga gttagaccgc cccaccttat ggactttatg | 900 |
| aatagcttgt tcgtgactgc tgagactgtt agaagccaaa ctgtgtgggg cggccacttg | 960 |
| gtcagctcac gcaacacggc tggcaaccgt atcaacttcc cgtcttacgg ggtctttaac | 1020 |
| cctggtggcg ccatttggat tgcagacgag gacccacgtc ttttttaccg caccctgtca | 1080 |
| gatccggttt tcgtcagagg cggatttggg aatcctcatt atgtcctggg ccttagggga | 1140 |
| gtggcttttcc aacagactgg caccaaccac accgtacgt tcgcaatag cgggaccata | 1200 |
| gattctcttg atgaaatccc acctcaagat aacagcggcg caccttggaa cgattattcc | 1260 |
| cacgtattaa atcacgttac gttcgtccgc tggccgggtg agatcagcgg cagcgattca | 1320 |
| tggagagcac caatgttctc ttggacgcac cgttcagcca ccctacaaa tacaattgac | 1380 |
| ccggagagga ttactcaaat cccattggtc aaagcacata cacttcagtc tgggaccacc | 1440 |
| gtggtcagag ggcctgggtt cacgggagga gacattctta gcgcacatc cggaggaccc | 1500 |
| ttcgcttata ctatcgttaa tataaatggg cagctccccc agcgctatcg tgccagaatc | 1560 |
| cgttacgcct ctactacaaa tctcagaatc tacgtgacgg ttgccggtga gcgcatcttt | 1620 |
| gctggtcagt ttaacaagac gatggatact ggcgacccac tgacattcca atctttctca | 1680 |
| tacgcaacta ttaatacagc tttcacattc ccaatgagcc agtcatcttt caccgtcggt | 1740 |

```
gctgataacct tcagctctgg caacgaagtc tatatcgaca gatttgagtt gattccagtt    1800
actgcaacgc tcgagtga                                                    1818

<210> SEQ ID NO 11
<211> LENGTH: 1818
<212> TYPE: DNA
<213> ORGANISM: Artificial Sequence
<220> FEATURE:
<223> OTHER INFORMATION: IRDIG.586.41

<400> SEQUENCE: 11
atggagaata tatccagaa tcaatgcgtg ccttacaact gtctcaataa tcccgaggtg      60
gagatattaa acgaggagag atccactggc agactgccac tcgacatatc cttgtccctt    120
acccgcttcc ttttgagcga atttgttcct ggtgtgggag tggctttcgg actgttcgat    180
ctgatatggg gctttatcac tccttctgat ggagcctct tccttctcca gattgagcag    240
ttgattgagc agagaataga aaccttggaa aggaatcggg caatcacgac cttgaggggt    300
ctcgccgata gctatgaaat ctacattgaa gcactgaggg agtgggaggc caaccccaat    360
aatgctcaat taagggaaga tgtgcggatt cgctttgcta atacagacga cgctctcatc    420
acagcaatca ataatttcac acttacatcc tttgaaatcc cgcttttgag cgtgtacgtt    480
caagcagcca atctccacct ctcacttctg agggacgctg tctcctttgg gcaaggttgg    540
ggactggata tcgctactgt gaataatcac tacaatagat taatcaacct gattcataga    600
tatacgaagc actgcttgga cacatacaat caaggactgg agaaccttag ggaactaac     660 actaggcagt gggcaaggtt caaccagttc agacgcgatc tcacacttac tgtgctggat    720
atcgttgctc tctttccgaa ctacgatgtt cgcacctacc caatccagac gtcatcccaa    780
ttaacaaggg aaatctacac ctcctcagtg attgaggact ctcccgtttc tgctaacata    840
cctaacggct tcaacagagc cgagttcgga gttagaccac cccaccttat ggactttatg    900
aatagcttgt tcgtgactgc tgagactgtt agaagccaaa ctgtgtgggg tggccacttg    960
gtcagctcac gcaacacggc tggcaaccgc atcaacttcc cgtcttacgg ggtctttaac   1020
cctggtggag ccatttggat tgcagacgag gacccacgcc cttttttaccg caccctgtca   1080 gatccggttt tcgtcagagg cggatttggg aatcctcatt atgtcctggg ccttagggga   1140 gtggcttttcc aacagactgg caccaaccac acccgcacgt ttcgcaatag cgggaccata   1200
gattctcttg atgaaatccc acctcaagat aacagcggag caccttggaa cgattattcc   1260
cacgtattaa atcacgttac gttcgtccgc tggcctggtg agatcagcgg cagcgattca   1320
tggagagcac caatgttctc ttggacgcac cgctcagcca cccctacaaa tacaatcgac   1380
ccggagagga ttactcaaat cccattggtc aaagcacata cacttcagtc tgggaccacc   1440
gtggtcagag ggcctgggtt cacgggagga gacattctta ggcgcacatc cggaggaccc   1500
ttcgcttata ctatcgttaa tataaatggg cagctccccc agcgctatag agccagaatc   1560
cgctacgcct ctactacaaa tctcagaatc tacgtgacgg ttgccggtga gcgcatcttt   1620
gctggtcagt ttaacaagac gatggatact ggcgacccac tgacattcca atctttctca   1680
tacgcaacta ttaatacagc tttcacattc ccaatgagcc agtcatcttt caccgtcggt   1740 gctgataacct tcagctctgg caacgaagtc tatatcgaca gatttgagtt gattccagtt   1800
actgcaacgc tcgagtga                                                   1818

<210> SEQ ID NO 12
```

<211> LENGTH: 1818
<212> TYPE: DNA
<213> ORGANISM: Artificial Sequence
<220> FEATURE:
<223> OTHER INFORMATION: IRDIG.586.42

<400> SEQUENCE: 12

| | | | | | |
|---|---|---|---|---|---|
| atggagaata | atatccagaa | tcaatgtgtc | ccatacaact | gcctcaataa | tcctgaagtt | 60 |
| gagatattaa | acgaagagag | gagcactgga | cgccttcccc | ttgacatctc | cctctccctc | 120 |
| acaaggttcc | tcttgtctga | gtttgttcct | ggtgtgggtg | tggcctttgg | cctctttgac | 180 |
| ctcatctggg | gattcatcac | cccatctgat | tggagcctct | tccttctcca | gattgaacag | 240 |
| ttgattgagc | agaggattga | gacccttgaa | aggaacagag | ccatcaccac | acttagaggc | 300 |
| cttgctgaca | gctatgaaat | ctacattgaa | gcactgaggg | agtgggaagc | caatcccaat | 360 |
| aatgctcaat | aagggaaga | tgtgaggatt | cgctttgcca | atacagatga | cgctttgatc | 420 |
| acagcaatca | ataatttcac | cctcaccagc | tttgagatcc | cttttgctctc | agtctatgtt | 480 |
| caagctgcaa | acctccactt | gagcttgctt | agggatgctg | tgtcgttcgg | acaaggttgg | 540 |
| ggacttgaca | tagccactgt | caataatcac | tacaacagat | taatcaactt | gattcatcgc | 600 |
| tacaccaaac | attgcttgga | cacctacaat | caaggattgg | agaacctcag | aggcaccaac | 660 |
| actcgccaat | gggcaaggtt | caaccagttt | agaagggatc | tcacactcac | tgtgcttgac | 720 |
| atagttgctc | tcttccccaa | ctatgatgtt | cgcacctacc | caattcaaac | cagctcccaa | 780 |
| ttaacaaggg | aaatctacac | ctcctcagtc | attgaggaca | gcccagtttc | tgccaacata | 840 |
| cccaatggtt | tcaatagggc | tgagtttggt | gtcagaccac | cccatctcat | ggacttcatg | 900 |
| aactccttgt | tcgtgactgc | cgagactgtt | aggtcccaaa | ctgtgtgggg | aggccaccct | 960 |
| gttagctccc | gcaacaccgc | tggcaaccgc | atcaacttcc | catcctatgg | ggtttttcaat | 1020 |
| cctggtggag | ccatctggat | tgcagatgag | gacccaaggc | cttctacag | aaccttgtca | 1080 |
| gatcctgtct | ttgtcagagg | aggctttggc | aatccacact | atgttcttgg | tttgagggga | 1140 |
| gtggcttttc | agcagactgg | caccaatcac | acccgcacat | tcagaaacag | cggcaccatt | 1200 |
| gacagccttg | atgaaatccc | acctcaagac | aacagcggag | caccctggaa | cgactactcc | 1260 |
| catgtattaa | atcatgtcac | cttttgtgcgc | tggcctggtg | agatcagcgg | ttcagattct | 1320 |
| tggagagcac | caatgttctc | atggacccat | cgctctgcca | cacccacaaa | tacaatagat | 1380 |
| ccagagagaa | tcacccagat | tcccttggtg | aaggcacaca | cacttcagtc | tggaaccaca | 1440 |
| gttgtcagag | ggcctgggtt | cactggtgga | gacattctca | gacgcacctc | tggagggcca | 1500 |
| tttgcttata | ctattgtcaa | tataaatggg | caacttcccc | aacgctacag | agccagaatc | 1560 |
| cgctatgctt | ccaccactaa | cttgagaatc | tatgtcacag | ttgctggtga | aaggatcttt | 1620 |
| gctggtcagt | tcaacaagac | aatggacact | ggtgatccat | tgacattcca | gtcattctcc | 1680 |
| tatgccacca | ttaatacagc | cttcacccttt | ccaatgagcc | agtccagctt | cacagtgggt | 1740 |
| gcagatacct | tcagctccgg | caatgaggtg | tacattgacc | gctttgagtt | gattccagtg | 1800 |
| actgccacac | tcgagtga | | | | | 1818 |

<210> SEQ ID NO 13
<211> LENGTH: 1818
<212> TYPE: DNA
<213> ORGANISM: Artificial Sequence
<220> FEATURE:
<223> OTHER INFORMATION: IRDIG.586.43

<400> SEQUENCE: 13

```
atggagaata atatccagaa tcaatgcgtg ccctacaact gtctgaataa tccggaggtg      60
gagatattaa acgaagagcg ctcaacgggg aggctcccgc tggacatatc cctgtcgctt     120
acccggttcc tcttgtccga gttcgttccg ggtgtgggcg tggcgttcgg actctttgat     180
ctcatctggg gcttcataac cccctctgat tggagcctgt tcctcctcca gatcgagcag     240
ctgatcgagc agaggataga gacattggag aggaaccggg caatcaccac gcttagggga     300
ctcgcagata gctatgaaat ctacattgaa gccctgcgcg agtgggaagc caacccgaat     360
aatgcacaat taagggagga tgtgaggatt cgctttgcca atacagacga cgctctgata     420
acggcaatca ataatttcac acttaccagc tttgagatcc cccttctgtc ggtctatgtt     480
caagctgcga acctgcacct gtcactgctc agagacgctg tctcgttcgg ccaaggctgg     540
ggactggaca tcgctaccgt gaataatcat acaacagat taatcaacct tattcacaga     600
tacacgaaac attgcttgga cacatacaat caagggctgg aaaacctgag gggcactaac     660
actcgccagt gggccagatt caaccagttt cggagggatc tcacccttac tgtgcttgat     720
atcgtcgccc ttttcccgaa ctacgatgtt cggacctacc caattcagac gtcatcccaa     780
ttaacaaggg aaatctacac cagctccgtc attgaagatt ctccagtttc cgctaacatc     840
cctaacggtt tcaaccgcgc agagttcggc gtgaggccac cccatctcat ggacttcatg     900
aactctttgt tcgtcactgc cgagaccgtt agaagccaga cggtgtgggg cggacacctc     960
gtgtcctcac gcaacactgc tggcaaccgg atcaacttcc cctcctacgg ggttttcaac    1020
cctggtggag ccatctggat tgcggacgag gacccacgcc cttttctaccg gaccttgtca   1080
gaccctgtct ttgtcagagg agggttcggc aacccgcatt atgtcctggg cctcagaggc    1140
gtcgcgtttc agcagaccgg cacgaaccac accggacgt tccggaacag cgggaccatc     1200
gactccctgg atgaaatccc accgcaagac aacagcggcg ctccctggaa cgactacagc    1260
catgtattaa accacgtgac ctttgtccgc tggcctggtg agatttcggg cagcgactca    1320
tggagggcac ccatgttctc ttggacgcac cgctcggcca cccctaccaa tacaatcgat    1380
ccggagagga ttactcagat cccgctcgtg aaggcccaca cccttcagtc cggaactact    1440
gttgtgaggg gtcctgggtt tacgggtggc gatattctta ggcgcacctc cggcggacca    1500
ttcgcctata ctattgtcaa tataaacggg caactgcccc agagatatag agcacgcatc    1560
cgctacgcct ctactacaaa cctgaggatc tacgtgacgg ttgccggtga gcggatcttc    1620
gctggccagt tcaacaagac aatggacact ggcgacccac tcacattcca atcattctcc    1680
tacgcgacca ttaatacagc gtttacattc ccaatgagcc agtctagctt caccgtgggt    1740
gcggacacgt tttcgtctgg gaacgaggtc tacatcgacc gctttgagtt gatcccagtg    1800
accgcgacac tcgagtga                                                  1818
```

<210> SEQ ID NO 14
<211> LENGTH: 1818
<212> TYPE: DNA
<213> ORGANISM: Artificial Sequence
<220> FEATURE:
<223> OTHER INFORMATION: Cry1F trunc Hx

<400> SEQUENCE: 14

```
atggagaaca acatacagaa tcagtgcgtc ccctacaact gcctcaacaa tcctgaagta      60
gagattctca cgaagagag gtcgactgga gattgccgt tagacatctc cctgtccctt      120
acacgtttcc tgttgtctga gtttgttcca ggtgtgggag ttgcgtttgg cctcttcgac     180
```

```
ctcatctggg gcttcatcac tccatctgat tggagcctct ttcttctcca gattgaacag    240
ttgattgaac aaaggattga gaccttggaa aggaatcggg ccatcactac ccttcgtggc    300
ttagcagaca gctatgagat ctacattgaa gcactaagag agtgggaagc caatcctaac    360
aatgcccaac tgagagaaga tgtgcgtata cgctttgcta acacagatga tgctttgatc    420
acagccatca acaacttcac ccttaccagc ttcgagatcc ctcttctctc ggtctatgtt    480
caagctgcta acctgcactt gtcactactg cgcgacgctg tgtcgtttgg gcaaggttgg    540
ggactggaca tagctactgt caacaatcac tacaacagac tcatcaatct gattcatcga    600
tacacgaaac attgtttgga tacctacaat cagggattgg agaacctgag aggtactaac    660
actcgccaat gggccaggtt caatcagttc aggagagacc ttacacttac tgtgttagac    720
atagttgctc tctttccgaa ctacgatgtt cgtacctatc cgattcaaac gtcatcccaa    780
cttacaaggg agatctacac cagttcagtc attgaagact ctccagtttc tgcgaacata    840
cccaatggtt tcaacagggc tgagtttgga gtcagaccac cccatctcat ggacttcatg    900
aactctttgt ttgtgactgc agagactgtt agatcccaaa ctgtgtgggg aggacactta    960
gttagctcac gcaacacggc tggcaatcgt atcaactttc tagttacgg ggtcttcaat   1020 cccggggggcg ccatctggat tgcagatgaa gatccacgtc ctttctatcg gaccttgtca   1080
gatcctgtct tcgtccgagg aggctttggc aatcctcact atgtactcgg tcttagggga   1140
gtggcctttc aacaaactgg tacgaatcac acccgcacat tcaggaactc cgggaccatt   1200
gactctctag atgagatacc acctcaagac aacagcggcg caccttggaa tgactactcc   1260
catgtgctga atcatgttac ctttgtgcgc tggccaggtg agatctcagg ttccgactca   1320
tggagagcac caatgttctc ttggacgcat cgtagcgcta ccccacaaaa caccattgat   1380
ccagagagaa tcactcagat tcccttggtg aaggcacaca cacttcagtc aggaactaca   1440
gttgtaagag ggccgggggtt cacgggagga gacattcttc gacgcactag tggaggacca   1500
ttcgcgtaca ccattgtcaa catcaatggg caacttcccc aaaggtatcg tgccaggata   1560
cgctatgcct ctactaccaa tctaagaatc tacgttacgg ttgcaggtga acggatcttt   1620
gctggtcagt tcaacaagac aatggatacc ggtgatccac ttacattcca atctttctcc   1680
tacgccacta tcaacaccgc gttcaccttt ccaatgagcc agagcagttt cacagtaggt   1740
gctgatacct tcagttcagg caacgaagtg tacattgaca ggtttgagtt gattccagtt   1800
actgccacac tcgagtaa                                                 1818
```

<210> SEQ ID NO 15
<211> LENGTH: 21
<212> TYPE: DNA
<213> ORGANISM: Artificial Sequence
<220> FEATURE:
<223> OTHER INFORMATION: Primer zmUbiLNK F

<400> SEQUENCE: 15
tgcagcagct atatgtggat t                                                21

<210> SEQ ID NO 16
<211> LENGTH: 17
<212> TYPE: DNA
<213> ORGANISM: Artificial Sequence
<220> FEATURE:
<223> OTHER INFORMATION: Primer ZmUbiLNK R

<400> SEQUENCE: 16
tccatggtgt cgtgtgg                                                     17

<210> SEQ ID NO 17
<211> LENGTH: 21
<212> TYPE: DNA
<213> ORGANISM: Artificial Sequence
<220> FEATURE:
<223> OTHER INFORMATION: Probe zmUbiLNK-Probe

<400> SEQUENCE: 17
aacaacaggg tgagcatcga c                                        21

<210> SEQ ID NO 18
<211> LENGTH: 20
<212> TYPE: DNA
<213> ORGANISM: Artificial Sequence
<220> FEATURE:
<223> OTHER INFORMATION: Primer GAAD1 F

<400> SEQUENCE: 18
tgttcggttc cctctaccaa                                          20

<210> SEQ ID NO 19
<211> LENGTH: 22
<212> TYPE: DNA
<213> ORGANISM: Artificial Sequence
<220> FEATURE:
<223> OTHER INFORMATION: Primer GAAD1 R

<400> SEQUENCE: 19
caacatccat caccttgact ga                                       22

<210> SEQ ID NO 20
<211> LENGTH: 24
<212> TYPE: DNA
<213> ORGANISM: Artificial Sequence
<220> FEATURE:
<223> OTHER INFORMATION: Probe GAAD1-Probe

<400> SEQUENCE: 20
cacagaaccg tcgcttcagc aaca                                     24

<210> SEQ ID NO 21
<211> LENGTH: 18
<212> TYPE: DNA
<213> ORGANISM: Artificial Sequence
<220> FEATURE:
<223> OTHER INFORMATION: Primer IVF-Taq

<400> SEQUENCE: 21
tggcggacga cgacttgt                                            18

<210> SEQ ID NO 22
<211> LENGTH: 19
<212> TYPE: DNA
<213> ORGANISM: Artificial Sequence
<220> FEATURE:
<223> OTHER INFORMATION: Primer IVR-Taq

<400> SEQUENCE: 22
aaagtttgga ggctgccgt                                           19

<210> SEQ ID NO 23
<211> LENGTH: 26
<212> TYPE: DNA
<213> ORGANISM: Artificial Sequence
<220> FEATURE:

<223> OTHER INFORMATION: Probe IV-Probe

<400> SEQUENCE: 23
cgagcagacc gccgtgtact tctacc                                        26

<210> SEQ ID NO 24
<211> LENGTH: 19
<212> TYPE: DNA
<213> ORGANISM: Artificial Sequence
<220> FEATURE:
<223> OTHER INFORMATION: Primer SPC1S

<400> SEQUENCE: 24
gaccgtaagg cttgatgaa                                                19

<210> SEQ ID NO 25
<211> LENGTH: 19
<212> TYPE: DNA
<213> ORGANISM: Artificial Sequence
<220> FEATURE:
<223> OTHER INFORMATION: Primer SPC1A

<400> SEQUENCE: 25
cttagctgga taacgccac                                                19

<210> SEQ ID NO 26
<211> LENGTH: 21
<212> TYPE: DNA
<213> ORGANISM: Artificial Sequence
<220> FEATURE:
<223> OTHER INFORMATION: Probe TQSPC-Probe

<400> SEQUENCE: 26
cgagattctc cgcgctgtag a                                             21

<210> SEQ ID NO 27
<211> LENGTH: 22
<212> TYPE: DNA
<213> ORGANISM: Artificial Sequence
<220> FEATURE:
<223> OTHER INFORMATION: Primer zmUbiv5LNK R

<400> SEQUENCE: 27
tccattgttg gatcctctag ag                                            22

<210> SEQ ID NO 28
<211> LENGTH: 36
<212> TYPE: DNA
<213> ORGANISM: Artificial Sequence
<220> FEATURE:
<223> OTHER INFORMATION: Primer pMYC2405 F

<400> SEQUENCE: 28
gatcatacca tggagaacaa catacagaat cagtgc                             36

<210> SEQ ID NO 29
<211> LENGTH: 25
<212> TYPE: DNA
<213> ORGANISM: Artificial Sequence
<220> FEATURE:
<223> OTHER INFORMATION: Primer pMYC2405 R

<400> SEQUENCE: 29
gatctcgagc tcgcgaaagc ttggc                                         25

<210> SEQ ID NO 30
<211> LENGTH: 1830
<212> TYPE: DNA
<213> ORGANISM: Bacillus thuringiensis

<400> SEQUENCE: 30

```
atggataaca atccgaacat caatgaatgc attccttata attgtttaag taaccctgaa      60
gtagaagtat taggtggaga aagaatagaa actggttaca ccccaatcga tatttccttg     120
tcgctaacgc aatttctttt gagtgaattt gttcccggtg ctggatttgt gttaggacta     180
gttgatataa tatggggaat ttttggtccc tctcaatggg acgcatttct tgtacaaatt     240
gaacagttaa ttaaccaaag aatagaagaa ttcgctagga accaagccat ttctagatta     300
gaaggactaa gcaatcttta tcaaatttac gcagaatctt ttagagagtg gaagcagat      360
cctactaatc cagcattaag agaagagatg cgtattcaat tcaatgacat gaacagtgcc     420
cttacaaccg ctattcctct ttttgcagtt caaaattatc aagttcctct tttatcagta     480
tatgttcaag ctgcaaattt acatttatca gttttgagag atgtttcagt gtttggacaa     540
aggtggggat tgatgccgc gactatcaat agtcgttata atgatttaac taggcttatt     600
ggcaactata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgaacagtt     780
tcccaattaa caagagaaat ttatacaaac ccagtattag aaaattttga tggtagtttt     840
cgaggctcgg ctcagggcat agaaagaagt attaggagtc cacatttgat ggatatactt     900
aacagtataa ccatctatac ggatgctcat aggggttatt attattggtc agggcatcaa     960
ataatggctt ctcctgtagg gttttcgggg ccagaattca cttttccgct atatggaact    1020
atgggaaatg cagctccaca acaacgtatt gttgctcaac taggtcaggg cgtgtataga    1080
acattatcgt ccactttata tagaagacct tttaatatag gataaataa tcaacaacta    1140
tctgttcttg acgggacaga atttgcttat ggaacctcct caaatttgcc atccgctgta    1200
tacagaaaaa gcggaacggt agattcgctg gatgaaatac cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaatttaata atataattcc ttcatcacaa attcacaaa tacctttaac aaaatctact    1440
aatcttggct ctggaacttc tgtcgttaaa ggaccaggat ttacaggagg agatattctt    1500
cgaagaactt cacctggcca gatttcaacc ttaagagtaa atattactgc accattatca    1560
caaagatatc gggtaagaat tcgctacgct tctaccacaa atttacaatt ccatacatca    1620
attgacggaa gacctattaa tcaggggaat ttttcagcaa ctatgagtag tgggagtaat    1680
ttacagtccg gaagctttag gactgtaggt tttactactc cgtttaactt ttcaaatgga    1740
tcaagtgtat ttacgttaag tgctcatgtc ttcaattcag gcaatgaagt ttatatagat    1800
cgaattgaat ttgttccggc agaagtaacc                                     1830
```

<210> SEQ ID NO 31
<211> LENGTH: 1818
<212> TYPE: DNA
<213> ORGANISM: Bacillus thuringiensis

<400> SEQUENCE: 31

```
atggagaata atattcaaaa tcaatgcgta ccttacaatt gtttaaataa tcctgaagta      60
```

-continued

```
gaaatattaa atgaagaaag aagtactggc agattaccgt tagatatatc cttatcgctt    120
acacgtttcc ttttgagtga atttgttcca ggtgtgggag ttgcgtttgg attatttgat    180
ttaatatggg gttttataac tccttctgat tggagcttat ttcttttaca gattgaacaa    240
ttgattgagc aaagaataga aacattggaa aggaaccggg caattactac attacgaggg    300
ttagcagata gctatgaaat ttatattgaa gcactaagag agtgggaagc aaatcctaat    360
aatgcacaat taagggaaga tgtgcgtatt cgatttgcta atacagacga cgctttaata    420
acagcaataa ataattttac acttacaagt tttgaaatcc ctcttttatc ggtctatgtt    480
caagcggcga atttacattt atcactatta agagacgctg tatcgtttgg gcagggttgg    540
ggactggata tagctactgt taataatcat tataatagat taataaatct tattcataga    600
tatacgaaac attgtttgga cacatacaat caaggattag aaaacttaag aggtactaat    660
actcgacaat gggcaagatt caatcagttt aggagagatt taacacttac tgtattagat    720
atcgttgctc tttttccgaa ctacgatgtt agaacatatc caattcaaac gtcatcccaa    780
ttaacaaggg aaatttatac aagttcagta attgaggatt ctccagtttc tgctaatata    840
cctaatggtt ttaatagggc ggaatttgga gttagaccgc cccatcttat ggactttatg    900
aattctttgt ttgtaactgc agagactgtt agaagtcaaa ctgtgtgggg aggacactta    960
gttagttcac gaaatacggc tggtaaccgt ataaatttcc ctagttacgg ggtcttcaat   1020
cctggtggcg ccatttggat tgcagatgag gatccacgtc ctttttatcg gacattatca   1080
gatcctgttt ttgtccgagg aggatttggg aatcctcatt atgtactggg gcttagggga   1140
gtagcatttc aacaaactgg tacgaaccac acccgaacat ttagaaatag tgggaccata   1200
gattctctag atgaaatccc acctcaggat aatagtgggg caccttggaa tgattatagt   1260
catgtattaa atcatgttac atttgtacga tggccaggtg agatttcagg aagtgattca   1320
tggagagctc caatgttttc ttggacgcac cgtagtgcaa cccctacaaa tacaattgat   1380
ccggagagga ttactcaaat accattggta aaagcacata cacttcagtc aggtactact   1440
gttgtaagag ggcccgggtt tacgggagga gatattcttc gacgaacaag tggaggacca   1500
tttgcttata ctattgttaa tataaatggg caattacccc aaaggtatcg tgcaagaata   1560
cgctatgcct ctactacaaa tctaagaatt tacgtaacgg ttgcaggtga acggattttt   1620
gctggtcaat ttaacaaaac aatggatacc ggtgacccat taacattcca atctttagt   1680 tacgcaacta ttaatacagc ttttacattc ccaatgagcc agagtagttt cacagtaggt   1740
gctgatactt ttagttcagg gaatgaagtt tatatagaca gatttgaatt gattccagtt   1800
actgcaacat ttgaatag                                                 1818
```